(12) United States Patent
Snapp et al.

(10) Patent No.: US 9,920,102 B2
(45) Date of Patent: Mar. 20, 2018

(54) FUSION TAGS FOR PROTEIN EXPRESSION

(71) Applicant: Albert Einstein College of Medicine, Inc., Bronx, NY (US)

(72) Inventors: Erik Lee Snapp, Bronx, NY (US); Lindsey M. Costantini, Durham, NC (US)

(73) Assignee: ALBERT EINSTEIN COLLEGE OF MEDICINE, INC., Bronx, NY (US)

( * ) Notice: Subject to any disclaimer, the term of this patent is extended or adjusted under 35 U.S.C. 154(b) by 12 days.

(21) Appl. No.: 15/152,908

(22) Filed: May 12, 2016

(65) Prior Publication Data

US 2016/0333061 A1 Nov. 17, 2016

Related U.S. Application Data

(60) Provisional application No. 62/162,329, filed on May 15, 2015.

(51) Int. Cl.
| | | |
|---|---|---|
| *C12N 15/62* | (2006.01) | |
| *C07K 14/435* | (2006.01) | |
| *C07K 14/005* | (2006.01) | |
| *C07K 14/72* | (2006.01) | |

(52) U.S. Cl.
CPC ...... *C07K 14/43595* (2013.01); *C07K 14/005* (2013.01); *C07K 14/723* (2013.01); *C12N 15/62* (2013.01); *C07K 2319/055* (2013.01); *C07K 2319/095* (2013.01); *C07K 2319/21* (2013.01); *C07K 2319/35* (2013.01); *C07K 2319/50* (2013.01); *C07K 2319/60* (2013.01); *C07K 2319/91* (2013.01)

(58) Field of Classification Search
CPC . C07K 2319/60; C07K 2319/35; C12N 15/62
See application file for complete search history.

(56) References Cited

U.S. PATENT DOCUMENTS

| | | | |
|---|---|---|---|
| 4,837,148 A | 6/1989 | Cregg | |
| 4,929,555 A | 5/1990 | Cregg et al. | |
| 5,625,048 A | 4/1997 | Tsien et al. | |
| 5,679,543 A | 10/1997 | Lawlis | |
| 5,777,079 A | 7/1998 | Tsien et al. | |
| 5,795,737 A | 8/1998 | Seed et al. | |
| 5,804,387 A | 9/1998 | Cormack et al. | |
| 5,874,304 A | 2/1999 | Zolotukhin et al. | |
| 5,968,750 A | 10/1999 | Zolotukhin et al. | |
| 6,020,192 A | 2/2000 | Muzyczka et al. | |
| 6,066,476 A | 5/2000 | Tsien et al. | |
| 6,090,919 A | 7/2000 | Cormack et al. | |
| 6,172,188 B1 | 1/2001 | Thastrup et al. | |
| 6,319,669 B1 | 11/2001 | Tsien et al. | |
| 6,818,443 B2 | 11/2004 | Thastrup et al. | |
| 6,852,849 B2 | 2/2005 | Tsien et al. | |
| 7,015,310 B2 | 3/2006 | Remington et al. | |
| 7,022,826 B2 | 4/2006 | Tsien et al. | |
| 7,271,241 B2 | 9/2007 | Waldo | |
| 7,314,736 B2 | 1/2008 | Remington et al. | |
| 7,314,915 B2 | 1/2008 | Thastrup et al. | |
| 7,332,598 B2 | 2/2008 | Tsien et al. | |
| 7,452,973 B2 | 11/2008 | Raines et al. | |
| 7,868,138 B2 | 1/2011 | Stemmer et al. | |

FOREIGN PATENT DOCUMENTS

| | | |
|---|---|---|
| EP | 0238023 A2 | 9/1987 |
| NZ | 330957 | 5/2000 |
| WO | WO 96/00787 A1 | 1/1996 |
| WO | WO 96/23810 A1 | 8/1996 |
| WO | WO 97/11086 A1 | 3/1997 |
| WO | WO 97/11094 A1 | 3/1997 |
| WO | WO 97/20078 A1 | 6/1997 |
| WO | WO 97/26333 A1 | 7/1997 |
| WO | WO 99/03997 A1 | 1/1999 |
| WO | WO 01/04331 A2 | 1/2001 |
| WO | WO 02/068605 A2 | 9/2002 |
| WO | WO 2013/142859 A2 | 9/2013 |

OTHER PUBLICATIONS

T7 Tag Peptide. 2017. www.apexbt.com/t7-tag.html.*
Suzuki et al. 2004; Protease-sensitive signalling by chemically engineered intramolecular fluorescent resonance energy transfer mutants of green fluorescent protein. Biochimica et Biophyica Acta. 1679:222-229.*
Ito et al. 1999; A novel mutant of green fluorescent protein with enhanced sensitivity for microanalysis at 488 nm excitation. Biochemical and Biophysical Research Communications. 264: 556-560.*
Grailhe et al. 2006; Monitoring protein interactions in the living cell through the fluorescence decays of cyan fluorescent protein. ChemPhysChem. 7:1442-1454.*
Bell et al., (2013) To fuse or not to fuse: what is your purpose? *Protein science : a publication of the Protein Society* 22: 1466-77.
Benali-Furet et al., (2005) Hepatitis C virus core triggers apoptosis in liver cells by inducing ER stress and ER calcium depletion. *Oncogene* 24: 4921-33.
Bevis et al., Rapidly maturing variants of the Discosoma red fluorescent protein (DsRed). *Nat. Biotechnol.* 20, 83-7 (2002).
Brandizzi et al., A greener world: the revolution in plant bioimaging. *Nat Rev Mol Cell Biol.* Jul. 2002;3(7):520-30.

(Continued)

*Primary Examiner* — Karen Cochrane Carlson
(74) *Attorney, Agent, or Firm* — Daniel A. Blasiole; Joseph T. Leone; DeWitt Ross & Stevens S.C.

(57) ABSTRACT

Fluorescent and non-fluorescent fusion tags derived from green fluorescent protein (GFP). The fusion tags harbor substitutions with respect to GFP that increase expression of target proteins to which the fusion tags are fused; increase solubility; prevent dimerization and oligomerization, particularly in oxidizing environments such as the endoplasmic reticulum (ER); and, in some cases, enhance fluorescence of the fusion tag itself. The substitutions include various combinations of substitutions at select cysteine residues in GFP, substitutions in or near the GFP chromophore, and/or other substitutions. The fusion tags can be used for increasing expression of target proteins for mass production thereof or as a fluorescent tag.

28 Claims, 15 Drawing Sheets

(56) References Cited

OTHER PUBLICATIONS

Breitling et al., N-linked protein glycosylation in the endoplasmic reticulum. *Cold Spring Harb. Perspect. Biol.* 5, a013359 (2013).
Bulbarelli et al., (2002) Trafficking of tail-anchored proteins: transport from the endoplasmic reticulum to the plasma membrane and sorting between surface domains in polarised epithelial cells. *Journal of cell science* 115: 1689-702.
Butt et al., (2005) SUMO fusion technology for difficult-to-express proteins. *Protein expression and purification* 43: 1-9.
Chang et al., High frequency transformation of Bacillus subtilis protoplasts by plasmid DNA, Molecular General Genetics, 168:111-115.
Chen et al., Identification of two lysosomal membrane glycoproteins. *J. Cell Biol.* 101, 85-95 (1985).
Chen et al., A membrane metalloprotease participates in the sequential degradation of a Caulobacter polarity determinant. *Mol. Microbiol.* 55, 1085-103 (2005).
Cherezov et al., (2007) High-resolution crystal structure of an engineered human beta2-adrenergic G protein-coupled receptor. *Science* 318: 1258-65 2583103.
Chun et al., (2012) Fusion partner toolchest for the stabilization and crystallization of G protein-coupled receptors. *Structure* 20: 967-76. 3375611.
Coffman et al., Every laboratory with a fluorescence microscope should consider counting molecules. *Mol. Biol. Cell* 25, 1545-8 (2014).
Cole et al., Diffusional mobility of Golgi proteins in membranes of living cells. *Science* 273, 797-801 (1996).
Costantini et al., A palette of fluorescent proteins optimized for diverse cellular environments. *Nat Commun.* Jul. 9, 2015;6:7670.
Costantini et al., (2012) Assessing the tendency of fluorescent proteins to oligomerize under physiologic conditions. *Traffic* 13: 643-9.
Costantini et al., Engineering and exploitation of a fluorescent HIV-1 gp120 for live cell CD4 binding assays. *Virology.* Feb. 2015;476:240-8.
Costantini et al., Fluorescent proteins in cellular organelles: serious pitfalls and some solutions. *DNA Cell Biol.* 32, 622-7 (2013).
Costantini et al., Cysteineless non-glycosylated monomeric blue fluorescent protein, secBFP2, for studies in the eukaryotic secretory pathway. *Biochem. Biophys. Res. Commun.* 430, 1114-9 (2013).
Couturier et al., A fluorescent tagging approach in *Drosophila* reveals late endosomal trafficking of Notch and Sanpodo. *J. Cell Biol.* 207, 351-63 (2014).
Crameri et al., Improved green fluorescent protein by molecular evolution using DNA shuffling. *Nat. Biotechnol.* 14, 315-319 (1996).
Cregg et al., (1985) Pichia pastoris as a host system for transformations, *Mol. Cell. Biol.* 5:3376.
Dalton et al., Over-expression of secreed proteins from mammalian cell lines, *Protein Science* 23, 517-525 (2014).
Das et al., (1984) Transformation of Kluyveromyces fragilis, *J. Bacteriol.* 158:1165.
De Louvencourt et al., (1983) Transformation of Kluyveromyces lactis by killer plasmid DNA, *J. Bactriol.* 154 :737.
Donnelly et al., (2001) Analysis of the aphthovirus 2A/2B polyprotein 'cleavage' mechanism indicates not a proteolytic reaction, but a novel translational effect: a putative ribosomal 'skip'. *J Gen Virol* 82: 1013-25.
Fisher et al., Laboratory Evolution of Fast-Folding Green Fluorescent Protein Using Secretory Pathway Quality Control, PLoS One, vol. 3, Issue 6 (2008).
Giordano et al., $pi(4,5)P_2$-Dependent and $Ca^{2+}$-Regulated Er-PM Interactions Mediated by the Extended Synaptotagmins, Cell 153, 1494-1509 (2013).
Gleeson et al., (1986), Tranformation of the Methylotrophic yeast Hansenula polymorpha, *J. Gen. Microbiol* 132:3459.
Glick et al., Factors affecting the expression of foreign proteins in *Escherichia coli*, J. Ind. Microbiol. 1:277.

Griesbeck et al., Reducing the Environmental Sensitivity of Yellow Fluorescent Protein, *The Journal of Biological Chemistry*, vol. 276, No. 31, pp. 29188-29194 (2001).
Grotzke et al., Deglycosylation-dependent fluorescent proteins provide unique tools for the study of ER-associated degradation. *Proc. Natl. Acad. Sci. U. S. A.* 110,3393-8 (2013).
Haas et al., Codon usage limitation in the expression of HIV-1 envelope glycoprotein, *Current Biology*, vol. 6, No. 3:315-324 (1996).
Hamer et al., (1982) Regulation in vivo of a cloned mammalian gene: cadmium induces the transcription of a mouse metallothionein gene in SV40 vectors, J. Mol. Appl. Genet. 1:273.
Haseloff et al., (1999) GFP variants for multispectral imaging of living cells. *Methods Cell Biol.* 58, 139-151.
Hattori et al., (2012) A fluorescence-detection size-exclusion chromatography-based thermostability assay for membrane protein precrystallization screening. *Structure* 20: 1293-9, 3441139.
Heim et al., (1994) Wavelength mutations and posttranslational autoxidation of green fluorescent protein. *Proc. Natl Acad. Sci. USA* 91, 12501-12504.
Henikoff & Henikoff (1989) Amino acid substitution matrices from protein blocks, *Proc. Natl. Acad. Sci. USA* 89:10915.
Hinnen et al., (1978) Transformation of yeast, *Proc. Natl. Acad. Sci. USA*, 75:1929.
Huang et al., Potential pitfalls and solutions for use of fluorescent fusion proteins to study the lysosome. *PLoS One* 9, e88893 (2014).
Ito et al., 1983) Transformation of intact yeast cells treated with alkali cations, *J. Bacteriol*, 153:163.
Jain et al., Oligomerization of green fluorescent protein in the secretory pathway of endocrine cells. *Biochem. J.* 360, 645-9 (2001).
Johnston et al., (1982) Isolation of the yeast regulatory gene GAL4 and analysis of its dosage effects on the galactose/melibiose regulon, *PNAS* (USA) 79:6971.
Julien et al., (2013) Broadly neutralizing antibody PGT121 allosterically modulates CD4 binding via recognition of the HIV-1 gp120 V3 base and multiple surrounding glycans. *PLoS pathogens* 9: e1003342.
Karlin et al., Applications and statistics for multiple high-scoring segments in molecular dequences, *Proc. Natl. Acad. Sci. USA* 90:5873-5787 (1993).
Katayama et al., GFP-like proteins stably accumulate in lysosomes. *Cell Struct. Funct.* 33, 1-12 (2008).
Kawate et al., (2006) Fluorescence-detection size-exclusion chromatography for precrystallization screening of integral membrane proteins. *Structure* 14: 673-81.
Kimura et al., Dissection of the autophagosome maturation process by a novel reporter protein, tandem fluorescent-tagged LC3. *Autophagy* 3, 452-60 (2007).
Koehler and Thorne (1987) Bacillus subtilis (natto) plasmid pLS20 mediates interspecies plasmid transfer, *Journal of Bacteriology*, 169:5771-5278.
Kredel et al., Mruby a bright monomeric red fluorescent protein for labeling of subcellular structures. *PLoS One* 4, e4391 (2009).
Kremers et al., Improved green and blue fluorescent proteins for expression in bacteria and mammalian cells. *Biochemistry.* Mar. 27, 2007;46(12):3775-83.
Kurtz et al., (1986) Integrative transformation of Candida albicans, using a cloned Candida ADE2 gene, *Mol. Cell Biol.* 6:142).
Lam et al., Improving FRET dynamic range with bright green and red fluorescent proteins. *Nat. Methods* 9, 1005-12 (2012).
Landgraf et al., Segregation of molecules at cell division reveals native protein localization. *Nat. Methods* 9, 480-2 (2012).
Larkin et al., (2007). Clustal W and Clustal X version 2.0. Bioinformatics, 23, 2947-2948.
Lippincott-Schwartz et al., Kinesin is the motor for microtubule-mediated Golgi-to-ER membrane traffic. *J. Cell Biol.* 128, 293-306 (1995).
Manivasakam and Schiestl (1993) High efficiency transformation of *Saccharomyes cerevisiae* by electroporation, Nucleic Acids Research 21(18):4414-5.

(56) References Cited

OTHER PUBLICATIONS

Marblestone et al., (2006) Comparison of SUMO fusion technology with traditional gene fusion systems: enhanced expression and solubility with SUMO. *Protein science : a publication of the Protein Society* 15: 182-9.2242369.

Markwardt et al., An Improved Cerulean Fluorescent Protein with Enhanced Brightness and Reduced Reversible Photoswitching. *PLoS One* 6, e17896 (2011).

Matz et al., Fluorescent proteins from nonbioluminescent *Anthozoa* species. *Nat. Biotechnol.* 17, 969-73 (1999).

McCusker et al., (2007) Heterologous GPCR expression: a bottleneck to obtaining crystal structures. *Biotechnology progress* 23: 540-7.

Miyawaki et al., (1997) Fluorescent indicators for $Ca^{2+}$ based on green fluorescent proteins and calmodulin. *Nature* 388, 882-887.

Miyawaki et al., Red fluorescent proteins: chromophore formation and cellular applications. *Curr. Opin. Struct. Biol.* 22, 679-88 (2012).

Morozova et al., Far-red fluorescent protein excitable with red lasers for flow cytometry and superresolution STED nanoscopy. *Biophys. J.* 99, L13-5 (2010).

Moyer et al., (1998) Membrane trafficking of the cystic fibrosis gene product, cystic fibrosis transmembrane conductance regulator, tagged with green fluorescent protein in madin-darby canine kidney cells. *The Journal of biological chemistry* 273: 21759-68.

Nagai et al., A variant of yellow fluorescent protein with fast and efficient maturation for cell-biological applications. *Nat. Biotechnol.* 20, 87-90 (2002).

Needleman & Wunsch, A general method applicable to the search for similarities in the amino acid seqence of two proteins, *J. Mol. Biol.* 48:443 (1970).

Orlandi et al., (1989) Cloning immuniglobulin variable domains for expression by the polymerase chain reaction, *PNAS* (USA) 86:3833.

Ormö, et al., Crystal structure of the Aequorea victoria green fluorescent protein. *Science* (80-. ). 273, 1392-5 (1996).

Paroutis et al., The pH of the secretory pathway: measurement, determinants, and regulation. *Physiology* (Bethesda). 19, 207-15 (2004).

Patterson, G. H., Knobel, S. M., Sharif, W. D., Kain, S. R. & Piston, D. W. Use of the green fluorescent protein and its mutants in quantitative fluorescence microscopy. *Biophys. J.* 73, 2782-90 (1997).

Pedelacq et al., (2006) Engineering and characterization of a superfolder green fluorescent protein. *Nature Biotechnology* 24: 79-88.

Pedrazzini et al., (1996) A mutant cytochrome b5 with a lengthened membrane anchor escapes from the endoplasmic reticulum and reaches the plasma membrane. *Proceedings of the National Academy of Sciences of the United States of America* 93: 4207-12.

Pearson & Lipman, Improved tools for biological sequene comparison, *Proc. Nat'l. Acad. Sci. USA* 85:2444 (1988).

Reed et al., (2001) High-level expression of a synthetic red-shifted GFP coding region incorporated into transgenic chloroplasts. *Plant J.* 27, 257-265.

Rizzo et al., Fluorescent protein tracking and detection: fluorescent protein structure and color variants. *Cold Spring Harb. Protoc.* 2009, pdb.top63 (2009).

Rizzo et al., An improved cyan fluorescent protein variant useful for FRET. *Nat. Biotechnol.* 22, 445-9 (2004).

Roggenkamp et al., In: Molecular Cloning: A Laboratory Manual, 3$^{rd}$ Ed., Cold Spring Harbor Laboratory Press (2001).

Rosenbaum et al., (2007) GPCR engineering yields high-resolution structural insights into beta2-adrenergic receptor function. *Science* 318: 1266-73.

Schröder et al., ER stress and the unfolded protein response. *Mutat. Res.* 569, 29-63 (2005).

Serrano-Vega et al., (2008) Conformational thermostabilization of the beta1-adrenergic receptor in a detergent-resistant form. *Proceedings of the National Academy of Sciences of the United States of America* 105: 877-82. 2242685.

Shaner et al., Advances in fluorescent protein technology. *J Cell Sci.* Dec. 15, 2007;120(Pt 24):4247-60.

Shaner et al., Improved monomeric red, orange and yellow fluorescent proteins derived from *Discosoma* sp. red fluorescent protein. *Nature Biotechnology* 22, 1567-1572 (2004).

Shaner et al., A bright monomeric green fluorescent protein derived from Branchiostoma lanceolatum. *Nat. Methods* 10, 407-9 (2013).

Shcherbakova et al., Red fluorescent proteins: advanced imaging applications and future design. *Angew. Chem. Int. Ed. Engl.* 51, 10724-38 (2012).

Shigekawa et al., (1988), Electroporation of eukaryotes and prokaryotes: a general approach to the introduction of macromolecules into cells, Bio/Technology 8:135.

Shemiakina et al., A monomeric red fluorescent protein with low cytotoxicity. *Nat. Commun.* 3, 1204 (2012).

Siegel et al., Strengths and weaknesses of recently engineered red fluorescent proteins evaluated in live cells using fluorescence correlation spectroscopy. *Int. J. Mol. Sci.* 14, 20340-58 (2013).

Siemering et al., (1996) Mutations that suppress the thermosensitivity of green fluorescent protein. *Curr. Biol.* 6, 1653-1663.

Silver et al., (1984), Amino terminus of the yeast GAL4 gene product is sufficient for nuclear localization, *PNAS* (USA) 81:5951.

Smith & Waterman, Comparison of biosequenes, *Adv. Appl. Math.* 2:482 (1981).

Snapp et al., (2003) Formation of stacked ER cisternae by low affinity protein interactions. *The Journal of cell biology* 163: 257-69.

Snapp et al., Monitoring chaperone engagement of substrates in the endoplasmic reticulum of live cells. *Proc. Natl. Acad. Sci.* 103, 6536-41 (2006).

Snapp et al., Design and use of fluorescent fusion proteins in cell biology. *Curr. Protoc. Cell Biol.* Chapter 21, Unit 21.4 (2005).

Su et al., (2002) Japanese encephalitis virus infection initiates endoplasmic reticulum stress and an unfolded protein response. *Journal of virology* 76: 4162-71.

Subach et al., Conversion of red fluorescent protein into a bright blue probe. *Chem. Biol.* 15, 1116-24 (2008).

Suzuki et al., Development of Cysteine-Free Fluorescent Proteins for the Oxidative Environment. *PLoS One* 7, e37551 (2012).

Thomas et al., (2014) Quality control in eukaryotic membrane protein overproduction. *Journal of molecular biology* 426: 4139-54.

Tsien et al., (1998) The green fluorescent protein. *Annu Rev Biochem.* 67:509-44.

Van Den Berg et al., Kluyveromyces as a host for heterologous gene expression: expression and secretion of prochymosin, (1990) Bio/Technology 8:145.

Wang et al., Characterization and development of photoactivatable fluorescent proteins for single-molecule-based superresolution imaging. *Proc. Natl. Acad. Sci. U. S. A.* 111, 8452-7 (2014).

Warne et al., (2008) Structure of a beta1-adrenergic G-protein-coupled receptor. *Nature* 454: 486-91.2923055.

Wei et al., Ubiquitous autofragmentation of fluorescent proteins creates abundant defective ribosomal products (DRiPs) for immunosurveillance, *The American Society for Biochemistry and Molecular Biology*, Inc. (2015).

Wu et al., (2009) A novel method for high-level production of TEV protease by Superfolder GFP tag, *Jour. Biomed. and Biotech.*, vol. 2009, Article ID 591923 8 pages.

XP-002760079 (Mar. 12, 2015), Calcitonin gene-related peptide, Database Geneseq [Online].

XP-002760080 (Jul. 9, 2003), Enhanced green Fluorescent protein, Database Geneseq [Online].

Xu et al., (2011) Development of an Automated High Throughput LCP-FRAP Assay to Guide Membrane Protein Crystallization in Lipid Mesophases. *Crystal growth & design* 11: 1193-201.

Yang et al., (1998) Improved fluorescence and dual color detection with enhanced blue and green variants of the green fluorescent protein. *J. Biol. Chem.* 273, 8212-8216.

Yang et al., One-step generation of mice carrying reporter and conditional alleles by CRISPR/Cas-mediated genome engineering. *Cell* 154, 1370-9 (2013).

Yang et al., The molecular structure of green fluorescent protein. *Nat. Biotechnol.* 14, 1246-1251 (1996).

(56) References Cited

OTHER PUBLICATIONS

Yanushevich et al., A strategy for the generation of non-aggregating mutants of Anthozoa fluorescent proteins. *FEBS Lett.* 511, 11-4 (2002).
Young et al., (2012) Recombinant protein expression and purification: a comprehensive review of affinity tags and microbial applications. *Biotechnology journal* 7: 620-34.
Young and Spizizen (1961), Physiologcal and genetic factors affecting transformation of *Bacillus subtilis*, *Journal of Bacteriology*, 81:823-829.
Zhang et al., (2015) Two disparate ligand-binding sites in the human P2Y receptor. *Nature*.
Zhong et al., Live cell imaging of protein dislocation from the endoplasmic reticulum. *J. Biol. Chem.* 287, 28057-66 (2012).
Ai et al., Exploration of new chromophore structures leads to the identification of improved blue fluorescent proteins. *Biochemistry* 46, 5904-10 (2007).
Almo et al., (2014) Better and faster: improvements and optimization for mammalian recombinant protein production. *Current opinion in structural. biology* 26: 39-43.
Altschul et al., Basic local alignment search tool, *J. Mol. Biol.* 215:403-410 (1990).
Aronson et al., Superfolder GFP is fluorescent in oxidizing environments when targeted via the Sec translocon. *Traffic* Copenhagen Denmark 12, 543-548 (2011).
Auldridge et al., (2015) LucY: a versatile new fluorescent reporter protein. *PLOS One* 10(4):e0124272.
Barak et al., (1997) Internal trafficking and surface mobility of a functionally intact beta2-adrenergic receptor-green fluorescent protein conjugate. *Molecular pharmacology* 51: 177-84.
Gleeson et al., (1986), Tranformation of the Methylotrophic yeast Hansenula polymorpha, *J. Gen. Microbiol.* 132:3459.
Grotzke et al., Deglycosylation-dependent fluorescent proteins provide unique tools for the study of ER-associated degradation. *Proc. Natl. Acad. Sci. U. S. A.* 110, 3393-8 (2013).
Manivasakam and Schiestl (1993) High efficiency transformation of *Saccharomyes cerevisiae* by electroporation, Nucleic Acids Research 2/(18):4414-5.
Miyawaki et al., Red fluorescent proteins: chromophore formation and cellular applications. *Curr. Opin. Struct. Biol.* 22, 679-88 (2012).
Siegel et al., Strengths and weaknesses of recently engineered red fluorescent proteins evaluated in live cells using fluorescence correlation spectroscopy. *Int. J. Mol. Sci* 14, 20340-58 (2013).

\* cited by examiner

SEQUENCE LISTING

<160> NUMBER OF SEQ ID NOS: 54

<210> SEQ ID NO 1
<211> LENGTH: 720
<212> TYPE: DNA
<213> ORGANISM: Artificial Sequence
<220> FEATURE:
<223> OTHER INFORMATION: FT2: Non-natural green fluorescent protein
      (GFP) variant.

<400> SEQUENCE: 1

```
atggtgagca agggcgagga gctgttcacc ggggtggtgc ccatcctggt cgagctggac    60
```

```
ggcgacgtaa acggccacaa gttcagcgtg cgcggcgagg gcgagggcga tgccaccaac     120
ggcaagctga ccctgaagtt catcagcacc accggcaagc tgcccgtgcc ctggcccacc     180
ctcgtgacca ccctgaccac aggcgtgcag agcttcagcc gctaccccga ccacatgaag     240
cgccacgact tcttcaagtc cgccatgccc gaaggctacg tccaggagcg caccatcagc     300
ttcaaggacg acggcaccta caagacccgc gccgaggtga agttcgaggg cgacaccctg     360
gtgaaccgca tcgagctgaa gggcatcgac ttcaaggagg acggcaacat cctggggcac     420
aagctggagt acaacttcaa cagccacaac gtctatatca ccgccgacaa gcagaagaac     480
ggcatcaagg ccaacttcaa gatccgccac aacgtggagg acggcagcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actcacggca tggacgagct gtacaagtaa     720
```

<210> SEQ ID NO 2
<211> LENGTH: 239
<212> TYPE: PRT
<213> ORGANISM: Artificial Sequence
<220> FEATURE:
<223> OTHER INFORMATION: FT2: Non-natural green fluorescent protein
      (GFP) variant.

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Ser Thr Thr Gly Lys Leu Pro Val Pro Trp Pro Thr Leu Val Thr Thr
    50                  55                  60

Leu Thr Thr Gly Val Gln Ser Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235
```

```
<210> SEQ ID NO 3
<211> LENGTH: 239
<212> TYPE: PRT
<213> ORGANISM: Artificial Sequence
<220> FEATURE:
<223> OTHER INFORMATION: sfGFP: Non-natural green fluorescent protein
      (GFP) variant.

<400> SEQUENCE: 3

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Val Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235

<210> SEQ ID NO 4
<211> LENGTH: 239
<212> TYPE: PRT
<213> ORGANISM: Artificial Sequence
<220> FEATURE:
<223> OTHER INFORMATION: mCerulean: Non-natural green fluorescent
      protein (GFP) variant.

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
```

```
                65                  70                  75                  80
Arg His Asp Phe Phe Lys Ser Ala Met Pro Glu Gly Tyr Val Gln Glu
                    85                  90                  95

Arg Thr Ile Ser Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Ile Ser Asp Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 5
<211> LENGTH: 239
<212> TYPE: PRT
<213> ORGANISM: Artificial Sequence
<220> FEATURE:
<223> OTHER INFORMATION: mVenus: Non-natural green fluorescent protein
      (GFP) variant.

<400> SEQUENCE: 5

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                    85                  90                  95

Arg Thr Ile Ser Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190
```

Pro Val Leu Leu Pro Asp Asn His Tyr Leu Ser Tyr Gln Ser Ala Leu
            195                 200                 205

Ser Lys Asp Pro Asn Glu Lys Arg Asp His Met Val Leu Leu Glu Arg
    210                 215                 220

Val Thr Ala Ala Gly Ile Thr Leu Gly Met Asp Glu Leu Tyr Lys
225                 230                 235

<210> SEQ ID NO 6
<211> LENGTH: 239
<212> TYPE: PRT
<213> ORGANISM: Artificial Sequence
<220> FEATURE:
<223> OTHER INFORMATION: EBFP2: Non-natural green fluorescent protein
      (GFP) variant.

<400> SEQUENCE: 6

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Ser His Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Val Asp Phe Lys Glu Asp Gly Asn Ile Leu Gly His Lys Leu Glu Tyr
130                 135                 140

Asn Phe Asn Ser His Asn Ile Tyr Ile Met Ala Val Lys Gln Lys Asn
145                 150                 155                 160

Gly Ile Lys Val Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Ser His Tyr Leu Ser Thr Gln Ser Val Leu
        195                 200                 205

Ser Lys Asp Pro Asn Glu Lys Arg Asp His Met Val Leu Leu Glu Phe
210                 215                 220

Arg Thr Ala Ala Gly Ile Thr Leu Gly Met Asp Glu Leu Tyr Lys
225                 230                 235

<210> SEQ ID NO 7
<211> LENGTH: 720
<212> TYPE: DNA
<213> ORGANISM: Artificial Sequence
<220> FEATURE:
<223> OTHER INFORMATION: moxGFP: Non-natural green fluorescent protein
      (GFP) variant.

<400> SEQUENCE: 7
atggtgtcca agggcgagga gctgttcacc ggggtggtgc ccatcctggt cgagctggac     60
ggcgacgtaa acggccacaa gttctccgtg cggggcgagg gcgagggcga tgccaccaac    120

```
ggcaagctga ccctgaagtt catcagcacc accggcaagc tgcccgtgcc ctggcccacc    180
ctcgtgacca ccctgaccta cggcgtgcag agcttctccc gctaccccga ccacatgaag    240
cgccacgact tcttcaagag cgccatgccc gaaggctacg tccaggagcg caccatctcc    300
ttcaaggacg acggcaccta caagacccgc gccgaggtga agttcgaggg cgacaccctg    360
gtgaaccgca tcgagctgaa gggcatcgac ttcaaggagg acggcaacat cctggggcac    420
aagctggagt acaacttcaa ctcccacaac gtctatatca ccgccgacaa gcagaagaac    480
ggcatcaagg ccaacttcaa gatccgccac aacgtggagg acggctccgt gcagctcgcc    540
gaccactacc agcagaacac ccccatcggc gacggccccg tgctgctgcc cgacaaccac    600
tacctgtcca cccagtccaa gctgtccaaa gaccccaacg agaagcgcga tcacatggtc    660
cttctggaat tcgtgaccgc cgccgggatc actcacggca tggacgagct gtacaagtaa    720
```

<210> SEQ ID NO 8
<211> LENGTH: 239
<212> TYPE: PRT
<213> ORGANISM: Artificial Sequence
<220> FEATURE:
<223> OTHER INFORMATION: moxGFP: Non-natural green fluorescent protein
      (GFP) variant.

<400> SEQUENCE: 8

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Ser Thr Thr Gly Lys Leu Pro Val Pro Trp Pro Thr Leu Val Thr Thr
    50                  55                  60

Leu Thr Tyr Gly Val Gln Ser Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235
```

<210> SEQ ID NO 9

<211> LENGTH: 720
<212> TYPE: DNA
<213> ORGANISM: Artificial Sequence
<220> FEATURE:
<223> OTHER INFORMATION: moxCerulean: Non-natural green fluorescent
      protein (GFP) variant.

<400> SEQUENCE: 9

```
atggtgtcaa agggcgaaga gctgtttact ggagtcgtcc caattctggt ggagctggat      60
ggagatgtca acgggcataa gttttcagtg cgaggagagg gagaaggaga cgctaccaac     120
ggcaagctga cactgaaatt catcagcacc acagggaagc tgcccgtgcc ttggccaacc     180
ctggtcacta ccctgagttg gggcgtccag tcatttgccc gataccaga ccacatgaag      240
cagcatgatt tctttaaatc cgctatgccc gagggctacg tgcaggaacg dacaatttc     300
tttaaggacg atggaacata caaaactaga gcagaggtga agttcgaagg agacactctg     360
gtcaacagga tcgagctgaa gggcattgac tttaagaag atggaaatat cctgggccac     420
aaactggagt acaacgccat ccatggcaac gtgtacatta cagctgataa gcagaaaaac     480
gggattaagg caaatttcgg actgaactgc aatgtggaag acgggagtgt ccagctggcc     540
gatcactacc agcagaacac tcctatcggc gacgggcccg tgctgctgcc tgataatcat     600
tatctgagca cccagtccaa gctgtctaag gaccccaatg agaaaagaga tcacatggtg     660
ctgctggagt ttgtgaccgc tgctggcatt accctgggga tggacgagct gtacaagtaa     720
```

<210> SEQ ID NO 10
<211> LENGTH: 239
<212> TYPE: PRT
<213> ORGANISM: Artificial Sequence
<220> FEATURE:
<223> OTHER INFORMATION: moxCerulean: Non-natural green fluorescent
      protein (GFP) variant.

<400> SEQUENCE: 10

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
                20                  25                  30

Glu Gly Glu Gly Asp Ala Thr Asn Gly Lys Leu Thr Leu Lys Phe Ile
            35                  40                  45

Ser Thr Thr Gly Lys Leu Pro Val Pro Trp Pro Thr Leu Val Thr Thr
    50                  55                  60

Leu Ser Trp Gly Val Gln Ser Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Ala Ile His Gly Asn Val Tyr Ile Thr Ala Asp Lys Gln Lys Asn
145                 150                 155                 160

Gly Ile Lys Ala Asn Phe Gly Leu Asn Cys Asn Val Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 11
<211> LENGTH: 720
<212> TYPE: DNA
<213> ORGANISM: Artificial Sequence
<220> FEATURE:
<223> OTHER INFORMATION: moxVenus: Non-natural green fluorescent protein
      (GFP) variant.

<400> SEQUENCE: 11
atggtgtcta aaggcgagga actgttcact ggggtggtgc ccatcctggt ggagctggac    60
ggcgatgtga atgggcacaa gtttagcgtg cgcggagagg gagaagggga cgctaccaac   120
ggaaagctga cactgaaact gatttccacc acaggcaagc tgcccgtgcc ttggccaaca   180
ctggtgacta ccctgggata cggcctccag agcttcgccc ggtatccaga ccacatgaag   240
cagcatgatt tctttaaatc agctatgccc gagggctacg tgcaggaacg acaatcttc    300 tttaaggacg atgggacata taaaactaga gccgaggtga agtttgaagg ggacactctg   360
gtgaacagga tcgagctgaa gggaattgac ttcaaagaag atggaaatat cctgggccac   420
aagctggagt acaacttcaa cagccataac gtgtatatca ccgccgataa gcagaaaaac   480
ggcatcaagg ctaatttcaa aattaggcac aatgtggaag acggcggggt gcagctggct   540
gatcattacc agcagaacac acctatcggg gacggacccg tgctgctgcc tgataatcac   600
tacctgagct atcagtccaa gctgtctaag gacccaaacg agaaacggga tcatatggtg   660
ctgaaagaat tgtgactgc cgctgggatt accctgggaa tggatgagct gtataagtga    720

<210> SEQ ID NO 12
<211> LENGTH: 239
<212> TYPE: PRT
<213> ORGANISM: Artificial Sequence
<220> FEATURE:
<223> OTHER INFORMATION: moxVenus: Non-natural green fluorescent protein
      (GFP) variant.

<400> SEQUENCE: 12

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
                20                  25                  30

Glu Gly Glu Gly Asp Ala Thr Asn Gly Lys Leu Thr Leu Lys Leu Ile
            35                  40                  45

Ser Thr Thr Gly Lys Leu Pro Val Pro Trp Pro Thr Leu Val Thr Thr
        50                  55                  60

Leu Gly Tyr Gly Leu Gln Ser Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125
```

Ile Asp Phe Lys Glu Asp Gly Asn Ile Leu Gly His Lys Leu Glu Tyr
130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Gly
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
        195                 200                 205

Ser Lys Asp Pro Asn Glu Lys Arg Asp His Met Val Leu Lys Glu Phe
        210                 215                 220

Val Thr Ala Ala Gly Ile Thr Leu Gly Met Asp Glu Leu Tyr Lys
225                 230                 235

<210> SEQ ID NO 13
<211> LENGTH: 717
<212> TYPE: DNA
<213> ORGANISM: Artificial Sequence
<220> FEATURE:
<223> OTHER INFORMATION: moxBFP: Non-natural green fluorescent protein
      (GFP) variant.

<400> SEQUENCE: 13
atggtgagca agggcgagga gctgttcacc ggggtggtgc ccatcctggt cgagctggac      60
ggcgacgtaa acggccacaa gttcagcgtg aggggcgagg cgagggcga tgccaccaac     120 ggcaagctga ccctgaagtt catcagtact accggcaagc tgcccgtgcc ctggcccacc     180
ctcgtgacca ccctgagcca cggcgtgcag gtgttcgccc gctacccga ccacatgaag     240 cagcacgact tcttcaagtc cgccatgccc gaaggctacg tccaggagcg caccatcttc     300
ttcaaggacg acggcaccta caagacccgc gccgaggtga agttcgaggg cgacaccctg     360
gtgaaccgca tcgagctgaa gggcgtcgac ttcaaggagg acggcaacat cctggggcac     420
aagctggagt acaacttcaa cagccacaac atctatatca tggccgtcaa gcagaagaac     480
ggcatcaagg ccaacttcaa gatccgccac aacgtggagg acggcagcgt gcagctcgcc     540
gaccactacc agcagaacac ccccatcggc gacggccccg tgctgctgcc cgacagccac     600
tacctgagca cccagtccaa gcttagcaaa gaccccaacg agaagcgcga tcacatggtc     660
ctgctggagt tccgcaccgc cgccgggatc actctcggca tggacgagct gtacaag      717

<210> SEQ ID NO 14
<211> LENGTH: 239
<212> TYPE: PRT
<213> ORGANISM: Artificial Sequence
<220> FEATURE:
<223> OTHER INFORMATION: moxBFP: Non-natural green fluorescent protein
      (GFP) variant.

<400> SEQUENCE: 14

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Ser Thr Thr Gly Lys Leu Pro Val Pro Trp Pro Thr Leu Val Thr Thr
    50                  55                  60

```
Leu Ser His Gly Val Gln Val Phe Ala Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Thr Tyr Lys Thr Arg Ala Glu
                100                 105                 110

Val Lys Phe Glu Gly Asp Thr Leu Val Asn Arg Ile Glu Leu Lys Gly
            115                 120                 125

Val Asp Phe Lys Glu Asp Gly Asn Ile Leu Gly His Lys Leu Glu Tyr
            130                 135                 140

Asn Phe Asn Ser His Asn Ile Tyr Ile Met Ala Val Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Ser His Tyr Leu Ser Thr Gln Ser Lys Leu
            195                 200                 205

Ser Lys Asp Pro Asn Glu Lys Arg Asp His Met Val Leu Leu Glu Phe
    210                 215                 220

Arg Thr Ala Ala Gly Ile Thr Leu Gly Met Asp Glu Leu Tyr Lys
225                 230                 235

<210> SEQ ID NO 15
<211> LENGTH: 36
<212> TYPE: PRT
<213> ORGANISM: Artificial Sequence
<220> FEATURE:
<223> OTHER INFORMATION: Prolactin signal sequence.

<400> SEQUENCE: 15

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser Thr Gly
            20                  25                  30

Pro Val Ala Thr
        35

<210> SEQ ID NO 16
<211> LENGTH: 17
<212> TYPE: DNA
<213> ORGANISM: Artificial Sequence
<220> FEATURE:
<223> OTHER INFORMATION: Primer.

<400> SEQUENCE: 16
gcaatgggcg gtaggcg                                                    17

<210> SEQ ID NO 17
<211> LENGTH: 43
<212> TYPE: DNA
<213> ORGANISM: Artificial Sequence
<220> FEATURE:
<223> OTHER INFORMATION: Primer.

<400> SEQUENCE: 17
gatcgcggcc gcgttacaat tcatccttat taagtttgtg ccc                       43

<210> SEQ ID NO 18
```

```
<211> LENGTH: 35
<212> TYPE: DNA
<213> ORGANISM: Artificial Sequence
<220> FEATURE:
<223> OTHER INFORMATION: Primer.

<400> SEQUENCE: 18
gatcaccggt cgtgagcaaa ggagaggaac tgttc                          35

<210> SEQ ID NO 19
<211> LENGTH: 48
<212> TYPE: DNA
<213> ORGANISM: Artificial Sequence
<220> FEATURE:
<223> OTHER INFORMATION: Primer.

<400> SEQUENCE: 19
gatcgcggcc gcttacagct cgtccttctt atacagctcg tccatccc            48

<210> SEQ ID NO 20
<211> LENGTH: 35
<212> TYPE: DNA
<213> ORGANISM: Artificial Sequence
<220> FEATURE:
<223> OTHER INFORMATION: Primer.

<400> SEQUENCE: 20
gatcaccggt cgccaccatg gtgtctaaag gcgag                          35

<210> SEQ ID NO 21
<211> LENGTH: 48
<212> TYPE: DNA
<213> ORGANISM: Artificial Sequence
<220> FEATURE:
<223> OTHER INFORMATION: Primer.

<400> SEQUENCE: 21
gatcgcggcc gcttacagct cgtccttctt atacagctca tccattcc            48

<210> SEQ ID NO 22
<211> LENGTH: 17
<212> TYPE: DNA
<213> ORGANISM: Artificial Sequence
<220> FEATURE:
<223> OTHER INFORMATION: Primer.

<400> SEQUENCE: 22
gcaatgggcg gtaggcg                                              17

<210> SEQ ID NO 23
<211> LENGTH: 30
<212> TYPE: DNA
<213> ORGANISM: Artificial Sequence
<220> FEATURE:
<223> OTHER INFORMATION: Primer.

<400> SEQUENCE: 23
gatcgcggcc gcttaattaa gcttgtgccc                                30

<210> SEQ ID NO 24
<211> LENGTH: 39
<212> TYPE: DNA
<213> ORGANISM: Artificial Sequence
<220> FEATURE:
<223> OTHER INFORMATION: Primer.

<400> SEQUENCE: 24
```

```
gatcaccggt cgccaccatg gtgagcaaag gagaggaac                                    39
```

<210> SEQ ID NO 25
<211> LENGTH: 27
<212> TYPE: DNA
<213> ORGANISM: Artificial Sequence
<220> FEATURE:
<223> OTHER INFORMATION: Primer.

<400> SEQUENCE: 25

```
gatcgcggcc gcttacttgt acagctc                                                27
```

<210> SEQ ID NO 26
<211> LENGTH: 29
<212> TYPE: DNA
<213> ORGANISM: Artificial Sequence
<220> FEATURE:
<223> OTHER INFORMATION: Primer.

<400> SEQUENCE: 26

```
gatcaccggt catggtgtct aaaggcgag                                              29
```

<210> SEQ ID NO 27
<211> LENGTH: 30
<212> TYPE: DNA
<213> ORGANISM: Artificial Sequence
<220> FEATURE:
<223> OTHER INFORMATION: Primer.

<400> SEQUENCE: 27

```
gatcgcggcc gctcacttat acagctcatc                                             30
```

<210> SEQ ID NO 28
<211> LENGTH: 45
<212> TYPE: DNA
<213> ORGANISM: Artificial Sequence
<220> FEATURE:
<223> OTHER INFORMATION: Primer.

<400> SEQUENCE: 28

```
atccgctagc gctaccggtc gccaccatgg tgagcaaggg cgagg                            45
```

<210> SEQ ID NO 29
<211> LENGTH: 41
<212> TYPE: DNA
<213> ORGANISM: Artificial Sequence
<220> FEATURE:
<223> OTHER INFORMATION: Primer

<400> SEQUENCE: 29

```
ctcgagatct gagtccggac ttgtacagct cgtccatgcc g                                41
```

<210> SEQ ID NO 30
<211> LENGTH: 48
<212> TYPE: DNA
<213> ORGANISM: Artificial Sequence
<220> FEATURE:
<223> OTHER INFORMATION: Primer.

<400> SEQUENCE: 30

```
atccgctagc gctaccggtc gccaccatgg tgtcaaaggg cgaagagc                         48
```

<210> SEQ ID NO 31
<211> LENGTH: 43
<212> TYPE: DNA

```
<213> ORGANISM: Artificial Sequence
<220> FEATURE:
<223> OTHER INFORMATION: Primer.

<400> SEQUENCE: 31
ctcgagatct gagtccggac ttatacagct cgtccatccc cag        43

<210> SEQ ID NO 32
<211> LENGTH: 50
<212> TYPE: DNA
<213> ORGANISM: Artificial Sequence
<220> FEATURE:
<223> OTHER INFORMATION: Primer.

<400> SEQUENCE: 32
atccgctagc gctaccggtc gccaccatgg tgtctaaagg cgaggaactg        50

<210> SEQ ID NO 33
<211> LENGTH: 45
<212> TYPE: DNA
<213> ORGANISM: Artificial Sequence
<220> FEATURE:
<223> OTHER INFORMATION: Primer.

<400> SEQUENCE: 33
ctcgagatct gagtccggac ttatacagct catccattcc caggg        45

<210> SEQ ID NO 34
<211> LENGTH: 53
<212> TYPE: DNA
<213> ORGANISM: Artificial Sequence
<220> FEATURE:
<223> OTHER INFORMATION: Primer.

<400> SEQUENCE: 34
atccgctagc gctaccggtc gccaccatgt cctcaaaggg agaagaagac aac        53

<210> SEQ ID NO 35
<211> LENGTH: 46
<212> TYPE: DNA
<213> ORGANISM: Artificial Sequence
<220> FEATURE:
<223> OTHER INFORMATION: CTCGAGATCTGAGTCCGGACTTATACAGTTCGTCCATCCCCATCAC

<400> SEQUENCE: 35
ctcgagatct gagtccggac ttatacagtt cgtccatccc catcac        46

<210> SEQ ID NO 36
<211> LENGTH: 26
<212> TYPE: DNA
<213> ORGANISM: Artificial Sequence
<220> FEATURE:
<223> OTHER INFORMATION: Primer.

<400> SEQUENCE: 36
gatcaccggt ctacccatac gacgtc        26

<210> SEQ ID NO 37
<211> LENGTH: 25
<212> TYPE: DNA
<213> ORGANISM: Artificial Sequence
<220> FEATURE:
<223> OTHER INFORMATION: Primer.

<400> SEQUENCE: 37
gatcaccggt agcgtagtct gggac        25
```

<210> SEQ ID NO 38
<211> LENGTH: 39
<212> TYPE: DNA
<213> ORGANISM: Artificial Sequence
<220> FEATURE:
<223> OTHER INFORMATION: Primer.

<400> SEQUENCE: 38
gatcgcggcc gcttacagct cgtccttctg cttgtcggc                    39

<210> SEQ ID NO 39
<211> LENGTH: 25
<212> TYPE: DNA
<213> ORGANISM: Artificial Sequence
<220> FEATURE:
<223> OTHER INFORMATION: Primer.

<400> SEQUENCE: 39
cggcgtgcag tcgttcgccc gctac                                   25

<210> SEQ ID NO 40
<211> LENGTH: 34
<212> TYPE: DNA
<213> ORGANISM: Artificial Sequence
<220> FEATURE:
<223> OTHER INFORMATION: Primer.

<400> SEQUENCE: 40
gagccacggc gtgcaggcct cgcccgcta cccc                          34

<210> SEQ ID NO 41
<211> LENGTH: 34
<212> TYPE: DNA
<213> ORGANISM: Artificial Sequence
<220> FEATURE:
<223> OTHER INFORMATION: Primer.

<400> SEQUENCE: 41
gagccacggc gtgcaggcct cgcccgcta cccc                          34

<210> SEQ ID NO 42
<211> LENGTH: 33
<212> TYPE: DNA
<213> ORGANISM: Artificial Sequence
<220> FEATURE:
<223> OTHER INFORMATION: Primer.

<400> SEQUENCE: 42
caggagcgca ccatctcctt caaggacgac ggc                          33

<210> SEQ ID NO 43
<211> LENGTH: 31
<212> TYPE: DNA
<213> ORGANISM: Artificial Sequence
<220> FEATURE:
<223> OTHER INFORMATION: Primer.

<400> SEQUENCE: 43
gaacggcatc aaggccaact tcaagatccg c                            31

<210> SEQ ID NO 44
<211> LENGTH: 35
<212> TYPE: DNA
<213> ORGANISM: Artificial Sequence
<220> FEATURE:

<223> OTHER INFORMATION: Primer.

<400> SEQUENCE: 44
ccctgaagtt catcagtact accggcaagc tgccc                          35

<210> SEQ ID NO 45
<211> LENGTH: 25
<212> TYPE: DNA
<213> ORGANISM: Artificial Sequence
<220> FEATURE:
<223> OTHER INFORMATION: Primer.

<400> SEQUENCE: 45
cggcgtgcag tcgttcagcc gctac                                     25

<210> SEQ ID NO 46
<211> LENGTH: 26
<212> TYPE: DNA
<213> ORGANISM: Artificial Sequence
<220> FEATURE:
<223> OTHER INFORMATION: Primer.

<400> SEQUENCE: 46
cttttgctaa gcctatggct gcaaac                                    26

<210> SEQ ID NO 47
<211> LENGTH: 28
<212> TYPE: DNA
<213> ORGANISM: Artificial Sequence
<220> FEATURE:
<223> OTHER INFORMATION: Primer.

<400> SEQUENCE: 47
gagcacccag tccaagctga gcaaagac                                  28

<210> SEQ ID NO 48
<211> LENGTH: 28
<212> TYPE: DNA
<213> ORGANISM: Artificial Sequence
<220> FEATURE:
<223> OTHER INFORMATION: Primer.

<400> SEQUENCE: 48
gtccttagac agcctggact gatagctc                                  28

<210> SEQ ID NO 49
<211> LENGTH: 28
<212> TYPE: DNA
<213> ORGANISM: Artificial Sequence
<220> FEATURE:
<223> OTHER INFORMATION: Primer.

<400> SEQUENCE: 49
gagctatcag tccaagctgt ctaaggac                                  28

<210> SEQ ID NO 50
<211> LENGTH: 33
<212> TYPE: DNA
<213> ORGANISM: Artificial Sequence
<220> FEATURE:
<223> OTHER INFORMATION: Primer.

<400> SEQUENCE: 50
gatcccatgg gtatggtgag caagggcgag gag                            33

```
<210> SEQ ID NO 51
<211> LENGTH: 26
<212> TYPE: DNA
<213> ORGANISM: Artificial Sequence
<220> FEATURE:
<223> OTHER INFORMATION: Primer.

<400> SEQUENCE: 51
gatcccatgg gtatggtgag caaagg                                          26

<210> SEQ ID NO 52
<211> LENGTH: 27
<212> TYPE: DNA
<213> ORGANISM: Artificial Sequence
<220> FEATURE:
<223> OTHER INFORMATION: Primer.

<400> SEQUENCE: 52
gatcccatgg gtatggtgtc taaaggc                                         27

<210> SEQ ID NO 53
<211> LENGTH: 26
<212> TYPE: DNA
<213> ORGANISM: Artificial Sequence
<220> FEATURE:
<223> OTHER INFORMATION: Primer.

<400> SEQUENCE: 53
gatcccatgg gtatgtcctc aaaggg                                          26

<210> SEQ ID NO 54
<211> LENGTH: 4
<212> TYPE: PRT
<213> ORGANISM: Artificial Sequence
<220> FEATURE:
<223> OTHER INFORMATION: Endoplasmic reticulum retention sequence.

<400> SEQUENCE: 54

Lys Asp Glu Leu
1
```

FUSION TAGS FOR PROTEIN EXPRESSION

FIELD OF THE INVENTION

The invention is directed to fusion tags for detecting and/or enhancing expression, solubility, or expression and solubility of a target protein.

BACKGROUND

Fusion tags for proteins are used for a variety of purposes, such as improved protein solubility, detection, purification, expression, and localization.

Common fusion tags used for protein detection include green fluorescent protein (GFP) and its many variants (Tsien 1998). However, a problem with GFP and its variants is that they are not particularly suitable for all cellular compartments. In oxidizing environments such as the eukaryotic secretory pathway, the mitochondrial inner membrane space, and the periplasm of gram-negative bacteria, for example, GFP and its variants have a tendency to oligomerize, misfold, cause misfolding of fused target proteins, or cause abnormal trafficking of fused target proteins. Fluorescent fusion tags suitable for oxidizing environments and other cellular compartments are needed.

Common fusion tags for use in increasing expression and solubility of proteins in bacteria include maltose binding protein (MBP), small ubiquitin-like modifier (SUMO), and glutathione S-transferase (GST), among others (Bell et al. 2013, Butt et al. 2005). However, few comparable tools are available for mammalian protein expression. Two commercially available mammalian tags are SUMO and Fc. Unfortunately, SUMO is restricted to N-terminal fusions (Marblestone et al. 2006), which limits its utility, especially for membrane proteins. Fc fusion can improve solubility of proteins, but is not reported to enhance expression levels. Fusion tags that significantly increase protein yield, particularly in mammalian cells, are needed.

SUMMARY OF THE INVENTION

The present invention provides fusion tags and associated materials and methods that address the aforementioned needs. Specifically, the present invention provides fluorescent or non-fluorescent fusion tags that enhance expression, solubility, or expression and solubility of a target protein, as well as corresponding biological reagents and methods associated therewith.

In one aspect, the invention provides a polynucleotide comprising a fusion tag-encoding sequence. The fusion tag-encoding sequence encodes a polypeptide sequence at least about 80% identical to SEQ ID NO:2, wherein the fusion tag-encoding sequence encodes a residue other than cysteine at a position corresponding to position 49 of SEQ ID NO:2 and a residue other than cysteine at a position corresponding to position 71 of SEQ ID NO:2. The fusion tag-encoding sequence in some versions encodes a residue other than cysteine and methionine at a position corresponding to position 71 of SEQ ID NO:2. The fusion tag-encoding sequence in some versions encodes a serine or a conservative variant of serine at a position corresponding to position 49 of SEQ ID NO:2 and a serine or a conservative variant of serine at a position corresponding to position 71 of SEQ ID NO:2.

The fusion tag-encoding sequence in some versions encodes one or more residues selected from the group consisting of a residue other than serine and threonine at a position corresponding to position 66 of SEQ ID NO:2 and a residue other than tyrosine, tryptophan, histidine, and phenylalanine at a position corresponding to position 67 of SEQ ID NO:2. The fusion tag-encoding sequence in some versions encodes one or more residues selected from the group consisting of a residue other than serine, threonine, and glycine at a position corresponding to position 66 of SEQ ID NO:2 and a residue other than tyrosine, tryptophan, histidine, and phenylalanine at a position corresponding to position 67 of SEQ ID NO:2, wherein the position corresponding to position 66 of SEQ ID NO:2 is a residue other than glycine when the position corresponding to position 67 of SEQ ID NO:2 is serine or threonine. The fusion tag-encoding sequence in some versions encodes a threonine or a conservative variant of threonine at a position corresponding to position 67 of SEQ ID NO:2 and, optionally, further encodes a residue other than glycine at a position corresponding to position 66 of SEQ ID NO:2, preferably a threonine or a conservative variant of threonine at a position corresponding to position 66 of SEQ ID NO:2.

The fusion tag-encoding sequence in some versions encodes a serine or a conservative variant of serine at a position corresponding to position 49 of SEQ ID NO:2, a valine or a conservative variant of valine at a position corresponding to position 71 of SEQ ID NO:2, and a histidine at a position corresponding to position 67 of SEQ ID NO:2.

The fusion tag-encoding sequence in some versions encodes a residue other than alanine and valine at a position corresponding to position 207 of SEQ ID NO:2, preferably, a lysine or a conservative variant of lysine at a position corresponding to position 207 of SEQ ID NO:2.

The fusion tag-encoding sequence in some versions encodes at least one, at least two, at least three, at least four, at least five, at least six, at least seven, at least eight, at least nine, at least ten, or all of: a residue other than serine at a position corresponding to position 31 of SEQ ID NO:2; a residue other than tyrosine at a position corresponding to position 40 of SEQ ID NO:2; a residue other than phenylalanine at a position corresponding to position 65 of SEQ ID NO:2; a residue other than serine at a position corresponding to position 66 of SEQ ID NO:2; a residue other than phenylalanine at a position corresponding to position 100 of SEQ ID NO:2; a residue other than asparagine at a position corresponding to position 106 of SEQ ID NO:2; a residue other than tyrosine at a position corresponding to position 146 of SEQ ID NO:2; a residue other than methionine at a position corresponding to position 154 of SEQ ID NO:2; a residue other than valine at a position corresponding to position 164 of SEQ ID NO:2; a residue other than isoleucine at a position corresponding to position 172 of SEQ ID NO:2; and a residue other than alanine and valine at a position corresponding to position 207 of SEQ ID NO:2.

The fusion tag-encoding sequence in some versions encodes at least one, at least two, at least three, at least four, or all of: arginine or a conservative variant of arginine at a position corresponding to position 31 of SEQ ID NO:2; asparagine or a conservative variant of asparagine at a position corresponding to position 40 of SEQ ID NO:2; threonine or a conservative variant of threonine at a position corresponding to position 106 of SEQ ID NO:2; valine or a conservative variant of valine at a position corresponding to position 172 of SEQ ID NO:2; and lysine or a conservative variant of lysine at a position corresponding to position 207 of SEQ ID NO:2.

The fusion tag-encoding sequence in some versions encodes at least one, at least two, at least three, at least four, at least five, or all of: leucine or a conservative variant of leucine at a position corresponding to position 65 of SEQ ID NO:2; threonine or a conservative variant of threonine at a position corresponding to position 66 of SEQ ID NO:2; serine or a conservative variant of serine at a position corresponding to position 100 of SEQ ID NO:2; phenylalanine or a conservative variant of phenylalanine at a position corresponding to position 146 of SEQ ID NO:2; threonine or a conservative variant of threonine at a position corresponding to position 154 of SEQ ID NO:2; and alanine or a conservative variant of alanine at a position corresponding to position 164 of SEQ ID NO:2.

The polynucleotide in some versions further comprises one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence.

The polynucleotide in some versions further comprises one or more cloning sites upstream, downstream, or both upstream and downstream of the fusion tag-encoding sequence. The fusion tag-encoding sequence in such versions preferably does not comprise a subsequence identical to at least one of the one or more cloning sites.

The polynucleotide in some versions further comprises: one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence; and one or more cloning sites upstream, downstream, or both upstream and downstream of the fusion tag-encoding sequence, wherein at least one of the one or more peptide cleavage-encoding sequences is disposed between at least one of the one or more cloning sites and the fusion tag-encoding sequence. The fusion The polynucleotide in some versions further comprises one or more affinity tag-encoding sequences upstream, downstream, or both upstream and downstream of the fusion tag-encoding sequence, each affinity tag-encoding sequence encoding an affinity tag in frame with the fusion tag-encoding sequence. The polynucleotide in such versions optionally further comprises one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence, wherein at least one of the one or more peptide cleavage-encoding sequences is disposed upstream or downstream of both the fusion tag-encoding sequence and at least one of the one or more affinity tag-encoding sequences.

The polynucleotide in some versions further comprises one or more target protein-encoding sequences upstream, downstream, or both upstream and downstream of the fusion tag-encoding sequence, each target protein-encoding sequence encoding a target protein in frame with the fusion tag-encoding sequence. The one or more target protein-encoding sequences in such versions optionally encode at least one secretory protein. The polynucleotide in such versions optionally further comprises one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence, wherein the one or more target protein-encoding sequences is further in frame with at least one of the one or more peptide cleavage-encoding sequences. The one or more target protein-encoding sequences in such versions preferably does not comprise a subsequence identical or substantially identical to at least one of the one or more peptide cleavage-encoding sequences. At least one of the one or more peptide cleavage-encoding sequences is preferably disposed between at least one of the one or more target protein-encoding sequences and the fusion tag-encoding sequence.

The polynucleotide in some versions comprises: one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence; one or more cloning sites upstream, downstream, or both upstream and downstream of the fusion tag-encoding sequence, wherein the fusion tag-encoding sequence does not comprise a subsequence identical or substantially identical to at least one of the one or more cloning sites, and wherein at least one of the one or more peptide cleavage-encoding sequences is disposed between the one or more cloning sites and the fusion tag-encoding sequence; and one or more affinity tag-encoding sequences upstream, downstream, or both upstream and downstream of the fusion tag-encoding sequence, each affinity tag-encoding sequence encoding an affinity tag in frame with the fusion tag-encoding sequence, wherein the at least one of the one or more peptide cleavage-encoding sequences is disposed between the at least one of the one or more cloning sites and at least one of the one or more affinity tag-encoding sequences.

The polynucleotide in some versions comprises: one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence; one or more target protein-encoding sequences upstream, downstream, or both upstream and downstream of the fusion tag-encoding sequence, each target protein-encoding sequence encoding a target protein in frame with the fusion tag-encoding sequence and further in frame with at least one of the one or more peptide cleavage-encoding sequences, wherein the at least one of the one or more peptide cleavage-encoding sequences is disposed between at least one of the one or more target protein-encoding sequences and the fusion tag-encoding sequence, and wherein the at least one or more target protein-encoding sequences does not comprise a subsequence identical with the at least one of the one or more peptide cleavage-encoding sequences; and one or more affinity tag-encoding sequences upstream, downstream, or both upstream and downstream of the fusion tag-encoding sequence, each affinity tag-encoding sequence encoding an affinity tag in frame with the fusion tag-encoding sequence, wherein the at least one of the one or more peptide cleavage-encoding sequences is disposed between the at least one of the one or more target protein-encoding sequences and at least one of the one or more affinity tag-encoding sequences.

In another aspect, the invention provides a polypeptide encoded by a polynucleotide as described above or anywhere herein.

In another aspect, the invention provides a method of tagging a target protein. The method comprises generating a polynucleotide encoding a target protein as described above or anywhere herein and expressing a polypeptide from the polynucleotide. The tagging of the method preferably enhances expression, solubility, or expression and solubility of the target protein.

The objects and advantages of the invention will appear more fully from the following detailed description of the preferred embodiment of the invention made in conjunction with the accompanying drawings.

DETAILED DESCRIPTION OF THE INVENTION

Figure 1:
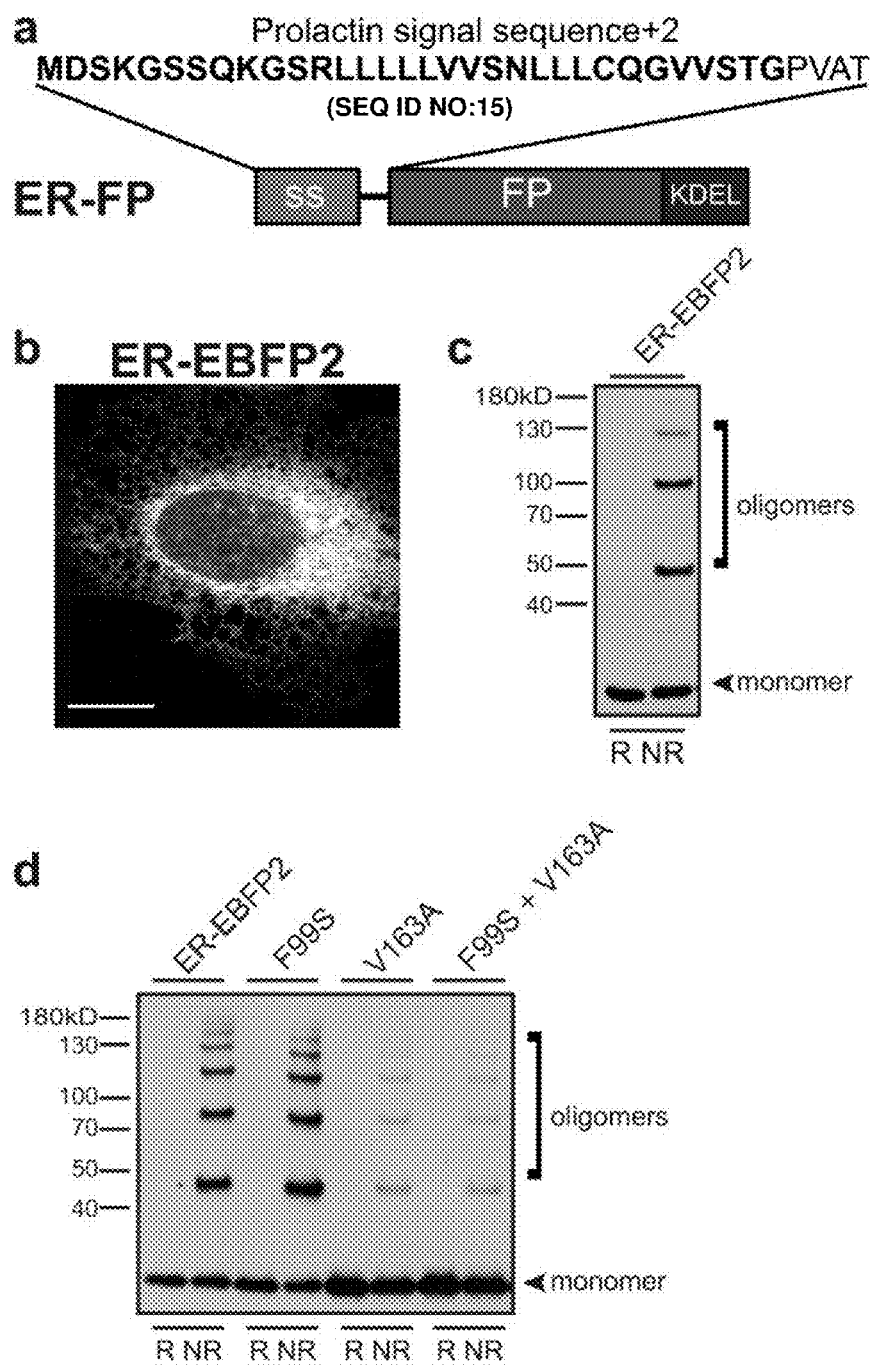
FIG. 1. ER-localized EBFP2 forms non-native disulfide bonds. (a) Schematic of ER-localization FP (ER-FP), containing prolactin signal sequence (SS) and KDEL retrieval motif. (b) Representative image of transiently transfected U-2 OS cells expressing ER-EBFP2, scale bar is 10 µm. (c) Immunoblot with reducing (R, +DTT) and non-reducing (NR, −DTT) conditions illustrate the tendency of ER-EBFP2 to oligomerize under NR conditions. The lower molecular weight band denotes expected molecular weight of monomeric EBFP2 (~25 kD). (d) Superfolder and cycle-3 mutations do not protect EBFP2 cysteine residues from inappropriate disulfide bond formation. Immunoblot of ER-EBFP2, with superfolder mutations (S30R, Y39N, N105T, Y145F, I171V (numbering of wild-type GFP)) and FP versions including cycle-3 GFP mutations (F99S, V163A (number of wild-type GFP)) forms higher molecular weight oligomers under NR conditions.

The fusion tags of the present invention have an amino acid sequence that is at least about 80% identical to SEQ ID NO:2:

(SEQ ID NO: 2)
MVSKGEELFTGVVPILVELDGDVNGHKFSVRGEGEGDATNGKLTLKFI

STTGKLPVPWPTLVTTLTTGVQSFSRYPDHMKRHDFFKSAMPEGYVQE

RTISFKDDGTYKTRAEVKFEGDTLVNRIELKGIDFKEDGNILGHKLEY

NFNSHNVYITADKQKNGIKANFKIRHNVEDGSVQLADHYQQNTPIGDG

PVLLPDNHYLSTQSKLSKDPNEKRDHMVLLEFVTAAGITHGMDELYK*

An exemplary coding sequence encoding SEQ ID NO:2 is SEQ ID NO:1:

(SEQ ID NO: 1)
ATGGTGAGCAAGGGCGAGGAGCTGTTCACCGGGGTGGTGCCCATCCTGG

TCGAGCTGGACGGCGACGTAAACGGCCACAAGTTCAGCGTGCGCGGCGA

GGGCGAGGGCGATGCCACCAACGGCAAGCTGACCCTGAAGTTCATCAGC

ACCACCGGCAAGCTGCCCGTGCCCTGGCCCACCCTCGTGACCACCCTGA

CCACAGGCGTGCAGAGCTTCAGCCGCTACCCCGACCACATGAAGCGCCA

CGACTTCTTCAAGTCCGCCATGCCCGAAGGCTACGTCCAGGAGCGCACC

ATCAGCTTCAAGGACGACGGCACCTACAAGACCCGCGCCGAGGTGAAGT

TCGAGGGCGACACCCTGGTGAACCGCATCGAGCTGAAGGGCATCGACTT

CAAGGAGGACGGCAACATCCTGGGGCACAAGCTGGAGTACAACTTCAAC

AGCCACAACGTCTATATCACCGCCGACAAGCAGAAGAACGGCATCAAGG

CCAACTTCAAGATCCGCCACAACGTGGAGGACGGCAGCGTGCAGCTCGC

CGACCACTACCAGCAGAACACCCCCATCGGCGACGGCCCCGTGCTGCTG

CCCGACAACCACTACCTGAGCACCCAGTCCAAGCTGAGCAAAGACCCCA

ACGAGAAGCGCGATCACATGGTCCTGCTGGAGTTCGTGACCGCCGCCGG

GATCACTCACGGCATGGACGAGCTGTACAAGTAA

Unless explicitly stated otherwise, all references herein to position numbers refer to residue positions in sequences at least 80% identical to SEQ ID NO:2 that correspond to residue positions in SEQ ID NO:2. Such correspondence of positions is obtained through alignment of the sequences at least 80% identical to SEQ ID NO:2 with SEQ ID NO:2 itself. A number of sequence alignment algorithms are known in the art. Exemplary sequence alignment algorithms are Clustal W and other Clustal programs (Larkin et al. 2007). Other algorithms and programs are discussed in further detail below.

SEQ ID NO:2 is alignable to GFP. It is common in the art to refer to residue positions in proteins alignable to GFP with the corresponding residue position numbers in GFP. With the exception of Example 1, the present disclosure departs from this practice by referring to the actual positions of SEQ ID NO:2 instead of the corresponding position in GFP. As SEQ ID NO:2 has an insertion of a valine at position 2, many of the position numbers discussed in the art for GFP or proteins alignable thereto will be lower by 1 than the position numbers discussed herein for SEQ ID NO:2.

Exemplary sequences that are at least 80% identical to SEQ ID NO:2 include SEQ ID NOS: 3, 4, 5, 6, 8, 10, 12, and 14.

In some versions, the fusion tags of the invention have an amino acid sequence that is at least about 85%, at least about 90%, at least about 95%, at least about 97%, or at least about 99% identical to SEQ ID NO:2.

In preferred versions, the fusion tags of the invention include a residue other than cysteine at position 49, a residue other than cysteine at position 71, or a residue other than cysteine at position 49 and a residue other than cysteine at position 71. Exclusion of cysteine at one or both of positions 49 and 71 reduces or prevents covalent oligomerization of fusion proteins containing the fusion tags in oxidizing environments and enhances expression of correctly folded fusions. In some versions of the invention, methionine is also excluded from position 71. In certain versions of the invention, each of positions 49 and 71 contain a serine or a conservative variant of serine. For blue fluorescent proteins, position 49 preferably contains a serine or a conservative variant of serine, and position 71 preferably contains a valine or a conservative variant of valine. See Table 1-2 below.

In some versions, the fusion tags of the invention are completely devoid of cysteines. Such exclusion of cysteines in the fusion tag does not preclude the presence of cysteines in target proteins fused to the fusion tag.

Some fusion tags of the invention comprise tyrosine, tryptophan, histidine, or phenylalanine at position 67. The particular residue at this position has the capacity to drastically affect the spectral properties of the fusion tag. Each of tyrosine, tryptophan, histidine, and phenylalanine, for example, can permit fluorescence of the fusion tag at different colors. Tyrosine can permit green fluorescence, tryptophan can permit cyan fluorescence, histidine can permit blue fluorescence, and phenylalanine can permit fluorescence at very short wavelengths (~442 nm) of light (Tsien 1998). Accordingly, fusion tags of the invention including tyrosine, tryptophan, histidine, or phenylalanine at position 67 are useful when fluorescence is desired.

Some fusion tags of the invention comprise a serine or a conservative variant of serine at a position corresponding to position 49 of SEQ ID NO:2, a valine or a conservative variant of valine at a position corresponding to position 71 of SEQ ID NO:2, and a histidine at a position corresponding to position 67 of SEQ ID NO:2. Such fusion tags may optionally also comprise any other residues or conservative variants of any other residues in SEQ ID NO:14 that differ with respect to SEQ ID NO:2 at corresponding positions thereof. These may include a residue other than valine at a position corresponding to position 164 of SEQ ID NO:2, such as alanine or a conservative variant of alanine that is not valine. It was unexpectedly found that, for blue fluorescent proteins, a valine or a conservative variant of valine at a position corresponding to position 71 of SEQ ID NO:2 yielded brighter fluorescence intensity compared to serine at this same position. This was particularly the case when combined with a residue other than valine at a position corresponding to position 164 of SEQ ID NO:2, such as alanine or a conservative variant of alanine that is not valine. See Table 1-2 below.

Other fusion tags of the invention have a residue other than tyrosine, tryptophan, histidine, and phenylalanine at position 67. Such fusion tags may include any one of alanine, arginine, asparagine, aspartic acid, cysteine, glutamine, glutamic acid, glycine, isoleucine, leucine, lysine, methionine, proline, serine, threonine, and valine at position 67. In some versions, the fusion tag may include threonine or a conservative variant of threonine at position 67. Although residues other than tyrosine, tryptophan, histidine, and phenylalanine at position 67 result in a non-fluorescent fusion tag, it was unexpectedly found that residues such as threonine at position 67 enhance expression of the fusion proteins comprising the fusion tag. See Example 2. Accordingly, fusion tags of the invention that exclude tyrosine, tryptophan, histidine, and phenylalanine at position 67 are useful when enhanced expression is desired but fluorescence is not. Any other mutation that inhibits chromophore formation in the fusion tag is also useful when enhanced expression is desired but fluorescence is not.

At least some fusion tags of the invention that have a residue other than tyrosine, tryptophan, histidine, and phenylalanine at position 67, such as fusion tags that have any one of alanine, arginine, asparagine, aspartic acid, cysteine, glutamine, glutamic acid, glycine, isoleucine, leucine, lysine, methionine, proline, serine, threonine, and valine at position 67, or fusion tags that have threonine or a conservative variant of threonine at position 67, also have a residue other than glycine at position 66.

At least some fusion tags of the invention that have a residue other than tyrosine, tryptophan, histidine, and phenylalanine at position 67, such as fusion tags that have any one of alanine, arginine, asparagine, aspartic acid, cysteine, glutamine, glutamic acid, glycine, isoleucine, leucine, lysine, methionine, proline, serine, threonine, and valine at position 67, or fusion tags that have threonine or a conservative variant of threonine at position 67, have a threonine or a conservative variant of threonine at position 66, have a threonine or a serine at position 66, or have a threonine at position 66.

Some fusion tags of the invention have a residue other than serine and threonine at position 66. Such fusion tags may include any one of alanine, arginine, asparagine, aspartic acid, cysteine, glutamine, glutamic acid, glycine, histidine, isoleucine, leucine, lysine, methionine, phenylalanine, proline, tryptophan, tyrosine, and valine at position 66. In some versions, the fusion tag may include glycine or a conservative variant of threonine at position 66. Although residues other than serine or threonine at position 66 result in a non-fluorescent tag, residues other than serine or threonine at position 66 enhance expression of fusion proteins comprising the fusion tag.

Some fusion tags of the invention have a residue other than serine, threonine, and glycine at position 66. Such fusion tags may include any one of alanine, arginine, asparagine, aspartic acid, cysteine, glutamine, glutamic acid, histidine, isoleucine, leucine, lysine, methionine, phenylalanine, proline, tryptophan, tyrosine, and valine at position 66.

Some fusion tags of the invention have a residue other than valine at position 69. Such fusion tags may include any one of alanine, arginine, asparagine, aspartic acid, cysteine, glutamine, glutamic acid, glycine, histidine, isoleucine, leucine, lysine, methionine, phenylalanine, proline, serine, threonine, tryptophan, and tyrosine at position 69. In some versions, the fusion tag may include glycine or a conservative variant of threonine at position 69. Residues other than valine at position 69, such as glycine or conservative variants thereof, enhance expression of fusion proteins comprising the fusion tag.

In some fusion tags, position 66 is a residue other than glycine when position 67 is serine. In some fusion tags, position 67 is a residue other than serine when position 66 is glycine. In some fusion tags, position 66 is a residue other than glycine when position 67 is threonine. In some fusion tags, position 67 is a residue other than threonine when position 66 is glycine. In some fusion tags, position 66 is a residue other than glycine when position 69 is glycine or valine. In some fusion tags, position 69 is a residue other than glycine or valine when position 66 is glycine.

Some fusion tags of the invention have a residue other than alanine and valine at a position corresponding to position 207 of SEQ ID NO:2. The residue other than alanine and valine in some cases may comprise lysine or a conservative variant of lysine. A residue other than alanine and valine at a position corresponding to position 207 of SEQ ID NO:2, such as lysine or a conservative variant of lysine, helps to prevent noncovalent dimer/oligomer formation.

Some fusion tags of the invention have one, some, or all of a residue other than serine at position 31, a residue other than tyrosine at position 40, a residue other than phenylalanine at position 65, a residue other than serine at position 66, a residue other than phenylalanine at position 100, a residue other than asparagine at position 106, a residue other than tyrosine at position 146, a residue other than methionine at position 154, a residue other than valine at position 164, a residue other than isoleucine at position 172, and a residue other than alanine and valine at position 207. The fusion tags may have an arginine or a conservative variant of arginine at position 31, asparagine or a conservative variant of asparagine at position 40, leucine or a conservative variant of leucine at position 65, threonine or a conservative variant of threonine at position 66, serine or a conservative variant of serine at position 100, threonine or a conservative variant of threonine at position 106, phenylalanine or a conservative variant of phenylalanine at position 146, threonine or a conservative variant of threonine at position 154, alanine or a conservative variant of alanine at position 164, valine or a conservative variant of valine at position 172, and/or lysine or a conservative variant of lysine at position 207. Fusion tags with these residues have increased rates of folding and, in tags having tyrosine, tryptophan, histidine, or phenylalanine at position 67, enhanced fluorescence.

"Conservative variant" refers to residues that are functionally similar to a given residue such that one or more of the functionally similar residues may substitute for the given residue. Conservative variants of the standard amino acids are well known in the art. In some versions, aliphatic, non-polar amino acids (G, A, I, L, and V) are conservative variants of one another. In some versions, aliphatic, polar amino acids (C, S, T, M, N, Y and Q) are conservative variants of one another. In some versions, aromatic amino acids (F, Y, W, and H) are conservative variants of one another. In some versions, basic amino acids (K, R, and H) are conservative variants of one another. In some versions, acidic amino acids (D and E) are conservative variants of one another. In some versions, an amino acid with an acidic side chain, E or D, is a conservative variant of its uncharged counterpart, Q or N, respectively; or vice versa. In some versions, each of the following groups contains other exemplary amino acids that are conservative variants of one another: A and G; D and E; N and Q; R and K; I, L, and M, and V; F, Y, and W; S and T; and C and M.

In addition to having at least one of the characteristics described above, such as the exclusion of cysteines at positions 49 and 71 and, optionally, a residue other than tyrosine, tryptophan, histidine, and phenylalanine at position 67, residues in the fusion tags of the invention may be substituted from SEQ ID NO:2 to have any one or more residues at positions corresponding to GFP or variants thereof. As described herein, a "variant" of GFP is any variant that can be aligned to GFP at a sequence identity of at least 80%. References discussing variants of GFP are cited throughout this disclosure and are incorporated herein by reference.

The fusion tags of the invention, for example, may optionally comprise any residues or conservative variants of any residues in SEQ ID NOS: 3, 4, 5, 6, 8, 10, 12, and 14 that differ with respect to SEQ ID NO:2 at corresponding positions thereof.

The fusion tags of the invention may have any one or combination of the following residues at the following positions (numbering of SEQ ID NO:2): M1, V2, S3, K4, G5, E6, E7, L8, F9, G10, T10, G11, I12, V12, V13, P14, I15, L16, V17, E18, L19, D20, E20, G21, D22, V23, N24, G25, H26, K27, R27, F28, S29, V30, R31, S31, G32, E33, G34, E35, G36, D37, A38, T39, Y40, N40, G41, K42, L43, T44, L45, K46, F47, L47, I48, L48, S49, T50, T51, G52, K53, L54, P55, V56, P57, W58, P59, T60, L61, V62, T63, T64, L65, F65, T66, S66, G66, T67, H67, Y67, W67, G68, V69, L69, Q70, S71, F72, S73, A73, R74, Y75, P76, D77, H78, M79, K80, R80, R81, Q81 H82, D83, F84, F85, K86, S87, A88, V88, M89, P90, E91, G92, Y93, V94, Q95 E96, R97, T98, I99, S100, F100, F101, K102, D103, D104, G105, T106, N106, Y107, K108, T109, R110, A111, E112, V113, K114, F115, E116, G117, D118, T119, L120, V121, N122, R123, I124, E125, L126, K127, G128, I129, V129, D130, F131, K132, E133, D134, G135, N136, I137, L138, G139, H140, K141, L142, E143, Y144, N145, F146, Y146, A146, N147, I147, S148, Y148, P148, H149, D149, N150, K150, V151, I151, Y152, I153, T154, M154, A155, D156, V156, K157, Q158, K159, N160, G161, I162, K163, A164, V164, N165, H165, F166, K167, I168, T168, R169, H170, N171, V172, I172, E173, T173, D174, G175, 5176, G176, V177, Q178, L179, A180, D181, H182, Y183, Q184, Q185, N186, T187, P188, I189, G190, D191, G192, P193, V194, L195, I195, L196, P197, D198, N199, S199, H200, Y201, L202, S203, T204, Y204, I204, Q205, S206, T206, K207, A207, V207, L208, S209, F209, K210, D211, P212, N213, K213, E214, K215, R216, D217, H218, M219, V220, L221, L222, E223, F224, V225, L225, R225, T226, A227, A228, G229, I230, T231, H232, L232 E232, G233, M234, D235, N235, E236, L237, Y238, K239, and conservative substitutions thereof. The valine at position 2 may be present, absent, or substituted with any other residue.

Various combinations of the above-mentioned residues may include S66, Y67, and/or G68, characteristic of wild-type GFP (Heim et al. 1994); A164, T168, and/or G176, characteristic of mGFP5 (Siemering et al. 1994); W67, A164, and/or G176, characteristic of mCFP (Haseloff 1999); G66, A73, A164, T168, G176, and/or Y204, characteristic of mYFP (Haseloff 1999); G66 and/or A73, characteristic of RsGFP (Reed et al. 2001); L65 and/or T66, characteristic of EGFP (Yang et al. 1998); R27, L65, T66, W67, I147, T154, A164, H165, and/or K213, characteristic of ECFP (Miyawaki et al. 1997); G66, L69, A73, and/or Y204, characteristic of EYFP (Miyawaki et al. 1997). Other individual or combinations of residues of GFP variants, all or any of which may be substituted in SEQ ID NO:2, are described elsewhere herein or described in references cited herein. See the examples below and throughout.

The fusion tags of the invention may be fused to target proteins for purposes of detecting the target protein via fluorescence, enhancing solubility of the target protein, increasing expression of the target protein, or other purposes. Fusion tags lacking cysteines at one or both of positions 49 and 71 are particularly suited for use in a wide range of cellular and non-cellular environments, including oxidizing environments such as the eukaryotic secretory pathway, the mitochondrial inner membrane space, and the periplasm of gram-negative bacteria. Fusion tags having tyrosine, tryptophan, histidine, or phenylalanine at position 67 are particularly suited for detecting target proteins in such environments via fluorescence. Fusion tags lacking a tyrosine, tryptophan, histidine, or phenylalanine at position 67 are particularly suited for enhancing expression and solubility of target proteins in such environments. Fusion tags having an arginine or a conservative variant of arginine at position 31, asparagine or a conservative variant of asparagine at position 40, leucine or a conservative variant of leucine at position 65, threonine or a conservative variant of threonine at position 66, serine or a conservative variant of serine at position 100, threonine or a conservative variant of threonine at position 106, phenylalanine or a conservative variant of phenylalanine at position 146, threonine or a conservative variant of threonine at position 154, alanine or a conservative variant of alanine at position 164, valine or a conservative variant of valine at position 172, and/or lysine or a conservative variant of lysine at position 207 have fast folding properties, which helps to increase fluorescence and/or solubility.

The fusion tags of the invention may be fused to any target protein. In some versions of the invention, the target protein is a secretory protein. As used herein "secretory protein" is any protein that is targeted, or capable of being targeted, to the cellular secretory pathway. These proteins include those that reside inside certain organelles (the endoplasmic reticulum, Golgi, or endosomes), are secreted from the cell, or are inserted into cellular membranes. A molecular signature of secretory proteins can be the presence of a signal peptide on the nascent protein in its natural state. As used herein, "signal peptide" refers to any peptide that is capable of being recognized by the signal-recognition particle (SRP). Signal peptides (sometimes referred to as signal sequences, targeting signals, localization signals, localization sequences, transit peptides, leader sequences, or leader peptides) are typically 14-60 amino acid-long peptides present at the N-terminus of the majority of newly synthesized proteins that are destined towards the secretory pathway. The core of signal peptides typically contains a 7-11 amino acid stretch of hydrophobic amino acids that has a tendency to form a single alpha helix. In addition, many signal peptides begin with a short positively charged stretch of amino acids, which may help to enforce proper topology of the polypeptide during translocation into the endoplasmic reticulum. At the end of signal peptides there is typically a 3 amino acid stretch of small polar amino acids that is recognized and cleaved by signal peptidase. However this cleavage site is absent from transmembrane-domains that serve as signal peptides, which are sometimes referred to as signal anchor sequences. Signal anchor sequences are often present in type II and multi-spanning membrane-bound proteins. The signal peptide may be cleaved either during or after completion of translocation by signal peptidase to generate a free signal peptide and a mature protein. The sequences of signal peptides are extremely heterogeneous, but can be recognized by their overall structure and functional properties, as described above. Signal peptides are well-recognized in the art. See Hegde et al. 2006. An exemplary signal peptide (SEQ ID NO:15) is shown in FIG. 1, Panel a (prolactin signal sequence).

The target protein may be a soluble protein or a membrane protein. The membrane protein may be an integral membrane protein, a peripheral membrane protein, or a membrane-associated protein. The integral membrane protein may be a type 1 integral membrane protein, a type 2 integral membrane protein, or a polytopic integral membrane protein. The polytopic integral membrane protein may comprise 2-12 or more transmembrane domains.

The target protein may have a sequence with a length of from about 3, about 10, or about 50 to about 3500, about 2000, about 2500, about 2000, about 1500, about 1000, about 500, or about 250 amino acids. The fusion protein may have a sequence with a length of from about 250 or about 300 to about 3750, about 3500, about 2000, about 2500, about 2000, about 1500, about 1000, about 500, or about 275 amino acids.

Fusion proteins of the invention may comprise a fusion tag fused to the N-terminus of a target protein, a fusion tag fused to the C-terminus of a target protein, or a fusion tag fused to each of the N-terminus and the C-terminus of a target protein. For fusion proteins targeted for the eukaryotic secretory pathway, a signal peptide should be placed on the N-terminus of fusion protein, regardless of whether the fusion tag is fused to the N-terminus or the C-terminus of a target protein. Accordingly, the signal peptide should be placed on the N-terminus of fusion tags in fusion proteins comprising the fusion tag fused to the N-terminus of the target protein. The signal peptide should be placed on the N-terminus of the target protein in fusion proteins comprising the fusion tag fused to the C-terminus of the target protein.

The fusion proteins of the invention may comprise a single target protein and a single fusion tag, a single target protein and multiple fusion tags, a single fusion tag and multiple target proteins, or multiple target proteins and multiple fusion tags linked in series. One or more of the target proteins may be disposed between at least two of the fusion tags, and/or, one or more of the fusion tags may be interspersed between at least two of the target proteins. The target proteins in fusion proteins that comprise multiple target proteins may be the same or different. The fusion tags in fusion proteins that comprise multiple fusion tags may be the same or different.

The fusion proteins of the invention may comprise a peptide cleavage sequence between the fusion tag and the target protein. This permits separation of the fusion tag from the target protein, which may be useful for certain applications. The peptide cleavage sequence may be a recognition sequence for a site-specific peptidase. A number of site-specific peptidases are known in the art. These include arg-C proteinase, asp-N endopeptidase, asp-N endopeptidase+N-terminal glu, BNPS-Skatole, caspase1, caspase2, caspase3, caspase4, caspase5, caspase6, caspase7, caspase8, caspase9, caspase10, chymotrypsin-high specificity (C-term to [FYW], not before P), chymotrypsin-low specificity (C-term to [FYWML], not before P), clostripain (clostridiopeptidase B), CNBr, enterokinase, factor Xa, formic acid, glutamyl endopeptidase, granzymeB, hydroxylamine, iodosobenzoic acid, lysC, lysN, NTCB (2-nitro-5-thiocyanobenzoic acid), neutrophil elastase, pepsin (pH1.3), pepsin (pH>2), proline-endopeptidase, proteinase K, SUMO proteases (Ulp1, Senp2, and SUMOstar), staphylococcal peptidase I, subtilisin BPN, tobacco etch virus (TEV) protease, thermolysin, thrombin, and trypsin, and variants thereof, among others. The cleavage recognition sites for these and other site-specific peptidases are well known in the art. Exemplary peptide cleavage sequences include the ExxYxQ↓(G/S) recognition sequence of TEV (and AcTEV and ProTEV), the LVPR↓G recognition sequence of thrombin, the IEGR↓x recognition sequence of factor Xa, and the DDDDK↓x recognition sequence of enterokinase. In some cases, the aphthovirus 2A/2B site (Donnelly et al. 2001) may be used as a "peptide cleavage sequence," even though the cleavage mechanism appears to be a translational effect rather than an enzymatic cleavage.

In some versions of the invention, particularly versions in which internal cleavage of the target protein is not desired during separation of the target protein from the fusion tag, the target protein does not comprise a sequence identical or substantially identical to the peptide cleavage sequence. In some versions of the invention, particularly versions in which internal cleavage of the fusion tag is not desired during separation of the target protein from the fusion tag, the fusion tag does not comprise a sequence identical or substantially identical to the peptide cleavage sequence. A "substantially identical" sequence in these contexts is a sequence that would be cleaved by the same mechanism (e.g., cleavage by the same site-specific peptidase, etc.) in which the peptide cleavage sequence would be cleaved.

The peptide cleavage sequence is preferably disposed on the fusion protein within about 35, within about 30, within about 25, within about 20, within about 15, within about 10, within about 5, within about 3, within about 2, or about 1 amino acid(s) away from the fusion tag, the target protein, or both. The target protein is preferably disposed on the fusion protein within about 45, within about 40, within about 35, within about 30, within about 25, within about 20, within about 15, within about 10, within about 5, within about 3, within about 2, or about 1 amino acid(s) away from the fusion tag.

The fusion proteins of the invention may also comprise an affinity tag. The affinity tags can be used for purification, detection with antibodies, or other uses. A number of affinity tags are known in the art. Exemplary affinity tags include the His tag, the Strep II tag, the T7 tag, the FLAG tag, the S tag, the HA tag, the c-Myc tag, the dihydrofolate reductase (DHFR) tag, the chitin binding domain tag, the calmodulin binding domain tag, and the cellulose binding domain tag. The sequences of each of these tags are well-known in the art. Preferred affinity tags are those smaller than about 20 amino acids, such as the His tag, the Strep II tag, the T7 tag, the FLAG tag, the S tag, the HA tag, the c-Myc tag.

In some versions, the affinity tag is disposed on the terminus of the fusion tag opposite the target protein. Thus, for N-terminal fusions (fusion proteins in which the fusion tag is fused to the N-terminus of the target protein), the affinity tag would be on the N-terminus of the fusion tag. For C-terminal fusions (fusion proteins in which the fusion tag is fused to the C-terminus of the target protein), the affinity tag would be on the C-terminus of the fusion tag. In other versions, the affinity tag is disposed between the fusion tag and the target protein. If a peptide cleavage sequence is present between the fusion tag and the target protein, the affinity tag may be proximal to the fusion tag with respect to the peptide cleavage sequence or may be proximal to the target protein with respect to the peptide cleavage sequence. In other versions, the affinity tag is disposed on a terminus of the target protein opposite the fusion tag. In other versions, the affinity tag may be disposed internally to the target protein and/or the fusion tag, such as on an unstructured loop. In yet other versions, each of the target protein and the fusion tag has an affinity tag associated therewith. The affinity tags may be the same or different. A peptide cleavage sequence may be disposed such that cleavage of the fusion protein yields a cleaved fusion tag and a separate cleaved target protein, each with an associated affinity tag.

In addition to the fusion tags and fusion proteins themselves, the invention provides polynucleotides configured for expressing a fusion tag alone (without any target protein fused thereto), for fusing a fusion tag to a target protein, and/or for expressing a fusion protein comprising a fusion tag fused to a target protein. The polynucleotides preferably comprise at least a fusion tag-encoding sequence that encodes a fusion tag of the invention. The polynucleotides preferably also comprise either a target protein-encoding sequence in frame with the fusion tag-encoding sequence or a cloning site suitable for inserting a target protein-encoding sequence in frame with the fusion tag-encoding sequence. The target protein-encoding sequence may encode any target protein. The fusion tag-encoding sequence preferably does not comprise a subsequence identical to the sequence of the cloning site.

The cloning site preferably comprises a sequence of about 4-250, about 4-200, about 4-150, about 4-100, about 4-75, about 4-50, about 4-25, about 4-15, about 10-250, about 10-200, about 10-150, about 10-100, about 10-75, about 10-50, about 10-25, about 10-15, about 20-250, about 20-200, about 20-150, about 20-100, about 20-75, about 20-50, or about 20-25 nucleotides that preferably does not appear in the fusion tag-encoding sequence or elsewhere in the polynucleotide. The cloning site may comprise a sequence suitable for ligase-free cloning (e.g., TOPO® cloning (Life Technologies), Gateway® cloning (Life Technologies), recombineering, etc.) and/or may comprise one or more restriction sites. The restriction sites are recognition sequences for restriction enzymes. The restriction enzyme sequences preferably do not appear in the fusion tag-encoding sequence or elsewhere in the polynucleotide.

Exemplary restriction enzyme sequences include AA/CGTT (AcII), A/AGCTT (HindIII), AAT/ATT (SspI), /AATT (MluCI, Tsp509I), A/CATGT (PciI), A/CCGGT (AgeI), ACCTGC (4/8) (BspMI, BfuAI), A/CCWGGT (SexAI), A/CGCGT (MluI), ACGGC (12/14) (BceAI), A/CGT (HpyCH4IV), ACN/GT (HpyCH4III), (10/15) ACNNNNGTAYC (12/7) (BaeI), (9/12) ACNNNNNCTCC (10/7) (BsaXI), A/CRYGT (AflIII), A/CTAGT (SpeI), ACTGG (1/−1) (BsrI), ACTGGG (5/4) (BmrI), A/GATCT (BglII), AGC/GCT (AfeI), AG/CT (AluI), AGG/CCT (StuI), AGT/ACT (ScaI), AT/CGAT (ClaI, BspDI), ATGCA/T (NsiI), AT/TAAT (AseI), ATTT/AAAT (SwaI), (11/13) CAANNNNNGTGG(12/10) (CspCI), C/AATTG (MfeI), CACGAG(−5/−1) (BssSI), CACGAG (BssSaI), CACGTC (−3/−3) (BmgBI), CAC/GTG (PmlI), CACNNN/GTG (DraIII), CACNN/NNGTG (AleI), CAGCAG(25/27) (EcoP15I), CAG/CTG (PvuII), CAGNNN/CTG (AlwNI), CAGTG(2/0) (BtsIMutI), NNCASTGNN/(TspRI), CA/TATG (NdeI), CATG/ (NlaIII), C/ATG (CviAII), /CATG (FatI), CAYNN/NNRTG (MslI), CC(12/16) (FspEI), CCANNNNN/NNNNTGG (XcmI), CCANNNNN/NTGG (BstXI), CCANNNN/NTGG (PflMI), CCATC(4/5) (BccI), C/CATGG (NcoI), CCCAGC(−5/−1) (BseYI), CCCGC(4/6) (FauI), CCC/GGG (SmaI), C/CCGGG (XmaI, TspMI), (0/−1)CCD (Nt.CviPII), CCDG(10/14) (LpnPI), CCGC(−3/−1) (AciI), CCGC/GG (SacII), CCGCTC(−3/−3) (BsrBI), C/CGG (MspI, HpaII), CC/NGG (ScrFI), /CCNGG (BssKI, StyD4I), C/CNNGG (BsaJI), CCNNNNN/NNGG (BslI), C/CRYGG (BtgI), CC/SGG (NciI), C/CTAGG (AvrII), CCTC(7/6) (MnlI), CCTCAGC(−5/−2) (BbvCI), CCTCAGC (Nb.BbvCI), CCTCAGC(−5/−7) (Nt.BbvCI), CCTGCA/GG (SbfI), CCTNAGC(−5/−2) (Bpu10I), CC/TNAGG (Bsu36I), CCTNN/NNNAGG (EcoNI), CCTTC(6/5) (HpyAV), CC/WGG (BstNI), /CCWGG (PspGI), C/CWWGG (StyI), (10/12)CGANNNNNNTGC (12/10) (BcgI), CGAT/CG (PvuI), CG/CG (BstUI), C/GGCCG (EagI), CG/GWCCG (RsrII), CGRY/CG (BsiEI), C/GTACG (BsiWI), CGTCTC(1/5) (BsmBI), CGWCG/ (Hpy99I), CMG/CKG (MspA1I), CNNR(9/13) (MspJI), CR/CCGGYG (SgrAI), C/TAG (BfaI), CTCAG(9/7) (BspCNI), C/TCGAG (XhoI PaeR7I TliI XhoI), CTCTTC(1/4) (Ead), CTGAAG(16/14) (AcuI), CTGCA/G (PstI), CTGGAG(16/14) (BpmI), C/TNAG (DdeI), C/TRYAG (SfcI), C/TTAAG (AflII), CTTGAG(16/14) (BpuEI), C/TYRAG (SmlI), C/YCGRG (AvaI BsoBI), GAAGA(8/7) (MboII), GAAGAC(2/6) (BbsI), GAANN/NNTTC (XmnI), GAATGC(1/−1) (BsmI), GAATGC (Nb.BsmI), G/AATTC (EcoRI), GACGC(5/10) (Hgalv), GACGT/C (AatII), GAC/GTC (ZraI), GACN/NNGTC (Tth111I PflFI), GACNN/NNGTC (PshAI), GACNNN/NNGTC (AhdI), GACNNNN/NNGTC (DrdI), GAG/CTC (Eco53kI), GAGCT/C (SacI), GAGGAG(10/8) (BseRI), GAGTC (4/5) (PleI), GAGTC (4/−5) (Nt.BstNBI), GAGTC (5/5) (MlyI), G/ANTC (HinfI), GAT/ATC (EcoRV), /GATC (MboI Sau3AI DpnII BfuCI), GA/TC (DpnI), GATNN/NNATC (BsaBI), G/AWTC (TfiI), GCAATG (2/0) (BsrDI), GCAATG (Nb.BsrDIv), GCAGC (8/12) (BbvI), GCAGTG (2/0) (BtsI), GCAGTG (BtsαI Nb.BtsI), GCANNNN/NTGC (BstAPI), GCATC (5/9) (SfaNI), GCATG/C (SphI), GCCGAG (21/19) (NmeAIII), GCC/GGC (NaeI), G/CCGGC (NgoMIV), GCCNNNN/NGGC (BglI), GCGAT/CGC (AsiSI), GCGATG(10/14) (BtgZI), G/CGC (HinP1I), GCG/C (HhaI), G/CGCGC (BssHII), GC/GGC-CGC (NotI), GC/NGC (Fnu4HI), GCN/NGC (Cac8I), GCNNNNN/NNGC (MwoI), G/CTAGC (NheI), GCTAG/C (BmtI), GCTCTTC(1/4) (SapI BspQI), GCTCTTC(1/−7) (Nt.BspQI), GC/TNAGC (BlpI), G/CWGC (TseI ApeKI), GDGCH/C (Bsp1286I), GGATC(4/5) (AlwI), GGATC(4/−5) (Nt.AlwI), G/GATCC (BamHI), GGATG(9/13) (FokI), GGATG(2/0) (BtsCI), GG/CC (HaeIII PhoI), GGCCGG/CC (FseI), GGCCNNNN/NGGCC (SfiI), GG/CGCC (NarI), G/GCGCC (KasI), GGC/GCC (SfoI), GGCGC/C (PluTI), GG/CGCGCC (AscI), GGCGGA(11/9) (EciI), GGGAC(10/14) (BsmFI), GGGCC/C (ApaI), G/GGCCC (PspOMI), G/GNCC (Sau96I), GGN/NCC (NlaIV), GGTAC/C (KpnI), G/GTACC (Acc65I), GGTCTC(1/5) (BsaI), GGTGA(8/7) (HphI), G/GTNACC (BstEII), G/GWCC (AvaII), G/GYRCC (BanI), GKGCM/C (BaeGI), GR/CGYC (BsaHI), GRGCY/C (BanII), GT/AC (RsaI), G/TAC (CviQI), GTA/TAC (BstZ17I), GTATCC(6/5) (BciVI), G/TCGAC (SalI), GTCTC(1/−5) (Nt.BsmAI), GTCTC(1/5) (BsmAI BcoDI), G/TGCAC (ApaLI), GTGCAG(16/14) (BsgI), GT/MKAC (AccI), GTN/NAC (Hpy166II), /GTSAC (Tsp45I), GTT/AAC (HpaI), GTTT/AAAC (PmeI), GTY/RAC (HincII), GWGCW/C (BsiHKAI), R/AATTY (ApoI), RCATG/Y (NspI), R/CCGGY (BsrFI), R/GATCY (BstYI), RGCGC/Y(HaeII), RG/CY (CviKI-1), RG/GNCCY (EcoO109I), RG/GWCCY (PpuMI), TAC/GTA (SnaBI), T/CATGA (BspHI), T/CCGGA (BspEI), TCCRAC(20/18) (MmeI), T/CGA (TaqαI), TCG/CGA (NruI), TCN/GA (Hpy188I), TC/NNGA (Hpy188III), T/CTAGA (XbaI), T/GATCA (MI), TG/CA (HpyCH4V), TGC/GCA (FspI), TGG/CCA (MscI), T/GTACA (BsrGI), T/TAA (MseI), TTAAT/TAA (PacI), TTA/TAA (PsiI), TT/CGAA (BstBI), TTT/AAA DraI), VC/TCGAGB (PspXI), W/CCGGW (BsaWI), YAC/GTR (BsaAI), and Y/GGCCR (EaeI).

The polynucleotide is preferably configured so that it is capable of generating a protein tag or fusion protein with any of the configurations as described herein. In one version, for example, the polynucleotide is configured with a peptide cleavage-encoding sequence disposed between a cloning site and a fusion tag-encoding sequence. An affinity tag-encoding sequence may be disposed on a side of the peptide cleavage-encoding sequence opposite the cloning site. In another version, the polynucleotide is configured with a peptide cleavage-encoding sequence disposed between a target protein-encoding sequence and a fusion tag-encoding sequence. An affinity tag-encoding sequence may be disposed on a side of the peptide cleavage-encoding sequence opposite the target protein-encoding sequence. Other configurations corresponding to the fusion protein configurations described herein are within the scope of the invention, wherein the placement of a target protein in the fusion protein corresponds with the placement of either a target protein-encoding sequence or a cloning site on the polynucleotide, the placement of a fusion tag on the fusion protein corresponds with the placement a fusion tag-encoding sequence on the polynucleotide, and the placement of an affinity tag on the fusion protein corresponds with the placement an affinity tag-encoding sequence on the polynucleotide.

The peptide cleavage-encoding sequence is preferably disposed on the polynucleotide within about 100, within about 90, within about 80, within about 70, within about 60, within about 50, within about 40, within about 30, within about 20, within about 10, within about 7, or within about 4 bases away from the fusion tag-encoding sequence, the cloning site, or both. The peptide cleavage-encoding sequence is preferably disposed on the polynucleotide within about 100, within about 90, within about 80, within about 70, within about 60, within about 50, within about 40, within about 30, within about 20, within about 10, within about 7, or within about 4 bases away from the fusion tag-encoding sequence, the target protein-encoding sequence, or both. The cloning site is preferably disposed on the polynucleotide within about 130, within about 120, within about 110, within about 100, within about 90, within about 80, within about 70, within about 60, within about 50, within about 40, within about 30, within about 20, within about 10, within about 7, or within about 4 bases away from the fusion tag-encoding sequence. The target protein-encoding sequence is preferably disposed on the polynucleotide within about 130, within about 120, within about 110, within about 100, within about 90, within about 80, within about 70, within about 60, within about 50, within about 40, within about 30, within about 20, within about 10, within about 7, or within about 4 bases away from the fusion tag-encoding sequence.

The target protein-encoding sequence and/or the fusion tag-encoding sequence preferably does not comprise a subsequence that encodes a peptide cleavage sequence identical or substantially identical to the peptide cleavage sequence encoded by the peptide cleavage-encoding sequence. In some cases, the fusion tag-encoding sequence may comprise a subsequence that encodes a peptide cleavage sequence identical or substantially identical to the peptide cleavage sequence encoded by the peptide cleavage-encoding sequence so long as the target protein-encoding sequence does not. A "substantially identical" sequence in these contexts is a sequence that would be cleaved by the same mechanism (e.g., cleavage by the same site-specific peptidase, etc.) in which the peptide cleavage sequence would be cleaved.

The polynucleotide may comprise more than one peptide cleavage-encoding sequence. The peptide cleavage-encoding sequences may be the same or different.

The polynucleotide preferably comprises a nucleotide sequence encoding a fusion tag that is at least about 60%, at least about 65%, at last about 70%, at least about 75%, at least about 80%, at least about 85%, at least about 90%, at least about 95%, at least about 97% identical to SEQ ID NO:1, SEQ ID NO:7, SEQ ID NO:9, SEQ ID NO:11, OR SEQ ID NO:13.

The codons in the polynucleotides encoding the following amino acid residues in the fusion tag, the target protein, or both preferably comprise or consist of gcc for alanine, cgc for arginine, aac for asparagine, gac for aspartic acid, tgc for cysteine, cag for glutamine, ggc for glycine, cac for histidine, atc for isoleucine, ctg for leucine, aag for lysine, ccc for proline, ttc for phenylalanine, agc for serine, acc for threonine, tac for tyrosine, and gtg for valine. In some cases, ggg may substitute ggc for glycine, att may substitute atc for isoleucine, ctc may substitute ctg for leucine, tcc may substitute agc for serine, and gtc may substitute gtg for valine. These codons are highly represented in native human genes and result in higher expression in mammalian cells. See U.S. Pat. No. 5,795,737.

The polynucleotides preferably comprise other elements suitable for expressing fusion proteins or isolated tags therefrom, such as promoters, enhancers, ribosome-binding sites, etc. The identity of such elements and their placement on a polynucleotide for expressing polypeptides therefrom are well known in the art.

The polynucleotides of the invention can be used in methods for making fluorescent fusion tags or fusion proteins, making fluorescent fusion tags or fusion proteins with enhanced solubility, increasing expression of a target protein, or other purposes. The methods comprise expressing a polynucleotide in a cell or a cell-free expression system. The cell may be a eukaryotic cell or a prokaryotic cell. Preferred eukaryotic cells include mammalian cells and yeast cells. Exemplary prokaryotic cells include bacterial cells.

Aspects pertaining to sequence comparison for determining sequence identity and other characteristics are as follows.

For sequence comparison, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a polynucleotide or amino acid sequence corresponding to SEQ ID NO:2.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 11, an Expect threshold (E) of 10, a cutoff of 100, M=5, N=−4, and a comparison of both strands. For amino acid sequences, the BLASTP program uses as defaults a word size (W) of 3, an Expect threshold (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a polynucleotide is considered similar to a reference sequence if the smallest sum probability in a comparison of the test polynucleotide to the reference polynucleotide is less than about 0.1, more preferably less than about 0.01, and most preferably less than about 0.001.

The terms "identical" or "percent identity", in the context of two or more polynucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill).

The phrase "substantially identical", in the context of two polynucleotides or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Terms used herein pertaining to genetic manipulation are defined as follows.

Deletion: The removal or absence of one or more nucleotides from a polynucleotide molecule or one or more amino acids from a protein with respect to a reference polynucleotide or reference protein, the regions on either side being joined together.

Derived: When used with reference to a polynucleotide or protein, "derived" means that the polynucleotide or polypeptide is isolated from a described source or is at least 70%, 80%, 90%, 95%, 99%, or more identical to a polynucleotide or polypeptide included in the described source.

Endogenous: As used herein with reference to a polynucleotide molecule and a particular cell, "endogenous" refers to a polynucleotide sequence or polypeptide that is in the cell and was not introduced into the cell using recombinant engineering techniques. For example, an endogenous gene is a gene that was present in a cell when the cell was originally isolated from nature.

Exogenous: As used herein with reference to a polynucleotide molecule or polypeptide in a particular cell, "exogenous" refers to any polynucleotide molecule or polypeptide that does not originate from that particular cell as found in nature. Thus, a non-naturally-occurring polynucleotide molecule or protein is considered to be exogenous to a cell once introduced into the cell. A polynucleotide molecule or protein that is naturally occurring also can be exogenous to a particular cell. For example, an entire coding sequence isolated from cell X is an exogenous polynucleotide with respect to cell Y once that coding sequence is introduced into cell Y, even if X and Y are the same cell type. The term "heterologous" is used herein interchangeably with "exogenous."

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Introduce: When used with reference to genetic material, such as a polynucleotide, and a cell, "introduce" refers to the delivery of the genetic material to the cell in a manner such that the genetic material is capable of being expressed within the cell. Introduction of genetic material includes both transformation and transfection. Transformation encompasses techniques by which a polynucleotide molecule can be introduced into cells such as prokaryotic cells or non-animal eukaryotic cells. Transfection encompasses techniques by which a polynucleotide molecule can be introduced into cells such as animal cells. These techniques include but are not limited to introduction of a polynucleotide via conjugation, electroporation, lipofection, infection, and particle gun acceleration.

Isolated: An "isolated" biological component (such as a polynucleotide molecule, polypeptide, or cell) has been substantially separated or purified away from other biological components in which the component naturally occurs, such as other chromosomal and extrachromosomal DNA and RNA and proteins. Polynucleotide molecules and polypeptides that have been "isolated" include polynucleotide molecules and polypeptides purified by standard purification methods. The term also includes polynucleotide molecules and polypeptides prepared by recombinant expression in a cell as well as chemically synthesized polynucleotide molecules and polypeptides. In one example, "isolated" refers to a naturally occurring polynucleotide molecule that is not immediately contiguous with both of the sequences with which it is immediately contiguous (one on the 5' end and one on the 3' end) in the naturally-occurring genome of the organism from which it is derived.

Polynucleotide: Encompasses both RNA and DNA molecules including, without limitation, cDNA, genomic DNA, and mRNA. Polynucleotides also include synthetic polynucleotide molecules, such as those that are chemically synthesized or recombinantly produced. The polynucleotide can be double-stranded or single-stranded. Where single-stranded, the polynucleotide molecule can be the sense strand, the antisense strand, or both. In addition, the polynucleotide can be circular or linear.

Operably linked: A first polynucleotide sequence is operably linked with a second polynucleotide sequence when the first polynucleotide sequence is placed in a functional relationship with the second polynucleotide sequence. For instance, a promoter is operably linked to a coding sequence if the promoter affects the transcription or expression of the coding sequence. An origin of replication is operably linked to a coding sequence if the origin of replication controls the replication or copy number of the polynucleotide in the cell. Operably linked polynucleotides may or may not be contiguous.

Operon: Configurations of separate genes that are transcribed in tandem as a single messenger RNA are denoted as operons. Thus, a set of in-frame genes in close proximity under the transcriptional regulation of a single promoter constitutes an operon. Operons may be synthetically generated using the methods described herein.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using rtPCR and protein levels can be assessed using SDS page gel analysis.

Recombinant: A recombinant polynucleotide molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of polynucleotide molecules or polypeptides, such as genetic engineering techniques. "Recombinant" is also used to describe polynucleotide molecules that have been artificially manipulated but contain the same regulatory sequences and coding regions that are found in the organism from which the polynucleotide was isolated. A recombinant cell or microorganism is one that contains an exogenous polynucleotide molecule, such as a recombinant polynucleotide molecule.

Recombinant cell: A cell that comprises a recombinant polynucleotide.

Vector or expression vector: An entity comprising a polynucleotide molecule that is capable of introducing the polynucleotide, or being introduced with the polynucleotide, into a cell for expression of the polynucleotide. A vector can include polynucleotide sequences that permit it to replicate in the cell, such as an origin of replication. A vector can also include one or more selectable marker genes and other genetic elements known in the art. Examples of suitable vectors are found below.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below.

Exogenous polynucleotides can be introduced stably or transiently into a cell using techniques well known in the art, including electroporation, calcium phosphate precipitation, DEAE-dextran mediated transfection, liposome-mediated transfection, conjugation, transduction, and the like. For stable transformation, a polynucleotide can further include a selectable marker. Suitable selectable markers include antibiotic resistance genes that confer, for example, resistance to neomycin, tetracycline, chloramphenicol, or kanamycin, genes that complement auxotrophic deficiencies, and the like. (See below for more detail.)

Various embodiments of the invention use an expression vector that includes a heterologous polynucleotide encoding a fusion tag or fusion protein described herein. Suitable expression vectors include, but are not limited to viral vectors, such as baculovirus vectors or those based on vaccinia virus, polio virus, adenovirus, adeno-associated virus, SV40, herpes simplex virus, and the like; phage vectors, such as bacteriophage vectors; plasmids; phagemids; cosmids; fosmids; bacterial artificial chromosomes; Pl-based artificial chromosomes; yeast plasmids; yeast artificial chromosomes; and any other vectors specific for cells of interest.

Useful vectors can include one or more selectable marker genes to provide a phenotypic trait for selection of transformed cells. The selectable marker gene encodes a protein necessary for the survival or growth of transformed cells grown in a selective culture medium. Cells not transformed with the vector containing the selectable marker gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. In alternative embodiments, the selectable marker gene is one that encodes dihydrofolate reductase or confers neomycin resistance (for use in eukaryotic cell culture), or one that confers tetracycline or ampicillin resistance (for use in a prokaryotic cell, such as *E. coli*).

The coding sequence in the expression vector is operably linked to an appropriate expression control sequence (promoters, enhancers, and the like) to direct synthesis of the encoded gene product. Such promoters can be derived from microbial or viral sources, including CMV and SV40. Depending on the cell/vector system utilized, any of a number of suitable transcription and translation control elements, including constitutive and inducible promoters, transcription enhancer elements, transcription terminators, etc. can be used in the expression vector (see e.g., Bitter et al. (1987) *Methods in Enzymology*, 153:516-544).

Suitable promoters for use in prokaryotic cells include but are not limited to: promoters capable of recognizing the T4, T3, Sp6, and T7 polymerases; the $P_R$ and $P_L$ promoters of bacteriophage lambda; the trp, recA, heat shock, and lacZ promoters of *E. coli*; the alpha-amylase and the sigma-specific promoters of *B. subtilis*; the promoters of the bacteriophages of *Bacillus*; *Streptomyces* promoters; the int promoter of bacteriophage lambda; the bla promoter of the beta-lactamase gene of pBR322; and the CAT promoter of the chloramphenicol acetyl transferase gene. Prokaryotic promoters are reviewed by Glick, *J. Ind. Microbiol.* 1:277 (1987); Watson et al, Molecular Biology of the Gene, 4th Ed., Benjamin Cummins (1987); and Sambrook et al., In: *Molecular Cloning: A Laboratory Manual*, 3$^{rd}$ ed., Cold Spring Harbor Laboratory Press (2001).

Non-limiting examples of suitable promoters for use within a eukaryotic cell are typically viral in origin and include the promoter of the mouse metallothionein I gene (Hamer et al. (1982) *J. Mol. Appl. Genet.* 1:273); the TK promoter of Herpes virus (McKnight (1982) *Cell* 31:355); the SV40 early promoter (Benoist et al. (1981) *Nature* (London) 290:304); the Rous sarcoma virus promoter; the cytomegalovirus promoter (Foecking et al. (1980) *Gene* 45:101); the yeast gal4 gene promoter (Johnston et al. (1982) *PNAS* (USA) 79:6971; Silver et al. (1984) *PNAS* (USA) 81:5951); and the IgG promoter (Orlandi et al. (1989) *PNAS* (USA) 86:3833).

Coding sequences can be operably linked to an inducible promoter. Inducible promoters are those wherein addition of an effector induces expression. Suitable effectors include proteins, metabolites, chemicals, or culture conditions capable of inducing expression. Suitable inducible promoters include but are not limited to the lac promoter (regulated by IPTG or analogs thereof), the lacUV5 promoter (regulated by IPTG or analogs thereof), the tac promoter (regulated by IPTG or analogs thereof), the trc promoter (regulated by IPTG or analogs thereof), the araBAD promoter (regulated by L-arabinose), the phoA promoter (regulated by phosphate starvation), the recA promoter (regulated by nalidixic acid), the proU promoter (regulated by osmolarity changes), the cst-1 promoter (regulated by glucose starvation), the tetA promoter (regulated by tetracycline), the cadA promoter (regulated by pH), the nar promoter (regulated by anaerobic conditions), the $p_L$ promoter (regulated by thermal shift), the cspA promoter (regulated by thermal shift), the T7 promoter (regulated by thermal shift), the T7-lac promoter (regulated by IPTG), the T3-lac promoter (regulated by IPTG), the T5-lac promoter (regulated by IPTG), the T4 gene 32 promoter (regulated by T4 infection), the nprM-lac promoter (regulated by IPTG), the VHb promoter (regulated by oxygen), the metallothionein promoter (regulated by heavy metals), the MMTV promoter (regulated by steroids such as dexamethasone) and variants thereof.

Alternatively, a coding sequence can be operably linked to a repressible promoter. Repressible promoters are those wherein addition of an effector represses expression. Examples of repressible promoters include but are not limited to the trp promoter (regulated by tryptophan); tetracycline-repressible promoters, such as those employed in the "TET-OFF"-brand system (Clontech, Mountain View, Calif.); and variants thereof.

In some versions, the cell is genetically modified with a heterologous polynucleotide that is operably linked to a constitutive promoter. Suitable constitutive promoters are known in the art and include constitutive adenovirus major late promoter, a constitutive MPSV promoter, and a constitutive CMV promoter.

The relative strengths of the promoters described herein are well known in the art.

In some versions, the cell is genetically modified with an exogenous polynucleotide encoding a single protein. In other embodiments, a modified cell is one that is genetically modified with exogenous polynucleotides encoding two or more proteins. Where the cell is genetically modified to express two or more proteins, those polynucleotides can each be contained in a single or in separate expression vectors. When the polynucleotides are contained in a single expression vector, the nucleotide sequences may be operably linked to a common control element (e.g., a promoter), that is, the common control element controls expression of all of the coding sequences in the single expression vector.

When the cell is genetically modified with heterologous polynucleotides encoding two or more proteins, one of the polynucleotides can be operably linked to an inducible promoter, and one or more of the polynucleotides can be operably linked to a constitutive promoter. Alternatively, all can be operably linked to inducible promoters or all can be operably linked to constitutive promoters.

Polynucleotides encoding enzymes desired to be expressed in a cell may be codon-optimized for that particular type of cell. Codon optimization can be performed for any polynucleotide by "OPTIMUMGENE"-brand gene design system by GenScript (Piscataway, N.J.).

The introduction of a vector into a bacterial cell may be performed by protoplast transformation (Chang and Cohen (1979) *Molecular General Genetics,* 168:111-115), using competent cells (Young and Spizizen (1961) *Journal of Bacteriology,* 81:823-829; Dubnau and Davidoff-Abelson (1971) *Journal of Molecular Biology,* 56: 209-221), electroporation (Shigekawa and Dower (1988) *Biotechniques,* 6:742-751), or conjugation (Koehler and Thorne (1987) *Journal of Bacteriology,* 169:5771-5278). Commercially available vectors for expressing heterologous proteins in bacterial cells include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx, in addition to those described in the following Examples.

Methods for transforming yeast cells with heterologous DNA and producing heterologous polypeptides therefrom are disclosed by Clontech Laboratories, Inc., Palo Alto, Calif., USA (in the product protocol for the "YEAST-MAKER"-brand yeast transformation system kit); Reeves et al. (1992) *FEMS Microbiology Letters* 99:193-198; Manivasakam and Schiestl (1993) *Nucleic Acids Research* 21(18): 4414-5; and Ganeva et al. (1994) *FEMS Microbiology Letters* 121:159-64. Expression and transformation vectors for transformation into many yeast strains are available. For example, expression vectors have been developed for the following yeasts: *Candida albicans* (Kurtz, et al. (1986) *Mol. Cell. Biol.* 6:142); *Candida maltosa* (Kunze et al. (1985) *J. Basic Microbiol.* 25:141); *Hansenula polymorpha* (Gleeson et al. (1986) *J. Gen. Microbiol.* 132:3459) and Roggenkamp et al. (1986) *Mol. Gen. Genet.* 202:302); *Kluyveromyces fragilis* (Das et al. (1984) *J. Bacteriol.* 158:1165); *Kluyveromyces lactis* (De Louvencourt et al. (1983) *J. Bacteriol.* 154:737) and Van den Berg et al. (1990) *Bio/Technology* 8:135); *Pichia quillerimondii* (Kunze et al. (1985) *J. Basic Microbiol.* 25:141); *Pichia pastoris* (Cregg et al. (1985) *Mol. Cell. Biol.* 5:3376; U.S. Pat. No. 4,837, 148; and U.S. Pat. No. 4,929,555); *Saccharomyces cerevisiae* (Hinnen et al. (1978) *Proc. Natl. Acad. Sci. USA* 75:1929 and Ito et al. (1983) *J. Bacteriol.* 153:163); *Schizosaccharomyces pombe* (Beach et al. (1981) *Nature* 300: 706); and *Yarrowia lipolytica* (Davidow et al. (1985) *Curr. Genet.* 10:380-471 and Gaillardin et al. (1985) *Curr. Genet.* 10:49).

Suitable procedures for transformation of *Aspergillus* cells are described in EP 238 023 and U.S. Pat. No. 5,679, 543. Suitable methods for transforming *Fusarium* species are described by Malardier et al., Gene, 1989, 78:147-56 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al. (1983) *Journal of Bacteriology,* 153: 163; and Hinnen et al. (1978) *PNAS USA,* 75:1920.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLE 1

Fluorescent Proteins for Diverse Cellular Environments

Summary

To perform quantitative live cell imaging, investigators require fluorescent reporters that accurately report protein localization and levels, while minimally perturbing the cell. Yet, within the biochemically distinct environments of cellular organelles, popular fluorescent proteins (FPs), including EGFP, can be unreliable for quantitative imaging, resulting in underestimation of protein levels and incorrect localization. Specifically, within the secretory pathway, significant populations of FPs misfold and fail to fluoresce due to non-native disulfide bond formation. Furthermore, transmembrane FP fusion constructs can disrupt organelle architecture due to oligomerizing tendencies of numerous common FPs. Here, we describe a powerful set of bright and inert FPs optimized for use in multiple cellular compartments, especially oxidizing environments and biological membranes. Also, we provide new insights into use of red FPs in the secretory pathway. Our monomeric "oxFPs" finally resolve long standing, underappreciated, and important problems of cell biology and should be useful for a number of applications.

Background

Since the cloning of green fluorescent protein (GFP) (Prasher et al. 1992), fluorescent proteins (FPs) have become standard imaging tools for cell biologists. FPs have been engineered to be brighter, faster folding, and to cover the range of the visible spectrum (Rizzo et al. 2009, Shaner et al. 2007, Miyawaki et al. 2012, Shcherbakova et al. 2012). Simultaneously, advanced microscopy techniques have pushed the boundaries of scientific questions that cell imaging techniques can be used to investigate. However, the range of subcellular environments within a cell pose a unique set of challenges for exploiting the full potential of FPs. Engineered FPs have been developed in the context of the cytoplasm of bacteria. In the absence of selective pressures, it is unsurprising that many FPs are not equally adapted to all cellular compartments. Recently, we reviewed the adverse impact of the chemically and physiologically distinct subcellular environments on FPs (Costantini et al. 2013). For example, the eukaryotic secretory pathway, mitochondrial inner membrane space, and periplasm of gram-negative bacteria are all oxidizing environments that promote disulfide bond formation. Endocytic and secretory compartments maintain acidic pH values well below that of the cytoplasm. Within the secretory pathway N-glycans are appended to asparagines. Another concern for many secretory fusion proteins is that localization of FPs to a membrane increases local effective protein concentrations and enhances FP tendencies to oligomerize. To quantitatively study fusion protein levels and behaviors (Coffman et al. 2014) within subcellular compartments, it is vital to use FPs that properly fold, fluoresce, and do not perturb the organization of the compartments.

While each cellular sub-compartment poses its own challenges for FPs, the eukaryotic secretory pathway arguably encompasses the greatest variety of challenges to FPs. Nascent secretory proteins enter the lumen of the endoplasmic reticulum (ER), where the proteins will encounter ER chaperones, which assist in protein folding, as well as the acquisition of post-translational modifications, i.e. N-linked glycosylation and disulfide bond formation. There is no general consensus sequence to identify cysteines appropriate for disulfide bond formation. As a result, a secretory pathway targeted cytoplasmic protein that contains cysteines is at risk for the formation of disulfide bonds that do not occur in the cytoplasm. Similarly, nascent proteins that contain a N—X—S/T consensus sequence, where X is any amino acid except proline, will be modified with a bulky sugar attached to the asparagines (Breitling et al. 2013). These sugars can impact protein folding, stability, function, and increase protein size, leading to potential steric problems (Grotzke et al. 2013, Zhong et al. 2012). Furthermore, nascent secretory proteins traverse the organelles that compose the secretory pathway, exiting the ER and entering the Golgi complex (GC) before continuing onward to vesicles and to the cell surface. During subcellular trafficking, membrane and soluble native secretory proteins are subject to quality control and the activities of resident proteins. The present example of optimizing FPs for the eukaryotic secretory pathway allowed us to determine the consequences of (1) the oxidizing environment, (2) non-native posttranslational modifications, and (3) intracellular trafficking on FP folding and behavior.

Most FPs contain at least one cysteine residue. Members of the family of *Aequorea victoria* GFP-derived FPs contain two highly conserved cysteine residues (C48, C70) (here and for the remainder of the present example, the numbering of amino acid residues follows that of GFP) located between the end of β-strand 3 and the end of the internal chromophore-containing α-helix, respectively. In a correctly folded FP of the GFP-like family of proteins, the internal helix is encased by an 1143 stranded barrel and the cysteine residue side chains face inward (Ormö et al. 1996, Yang et al. 1996). A FP's β-barrel must properly fold to produce the local environment required for the autocatalytic chromophore formation reaction to proceed and produce fluorescence (Ormö et al. 1996). Structurally, if either cysteine residue incorporates into a disulfide bond in the ER, it is highly unlikely the FP could achieve the required chromophore-forming structure. Therefore, when using FPs within the secretory pathway, it is preferable to select FPs that naturally lack cysteine residues, such as the family of mFruit FPs (Shaner et al. 2004) or are resistant to disulfide bond formation, such as superfolder GFP (sfGFP) (Pedelacq et al., Aronson et al. 2011). An alternative approach has been to engineer cysteine-less FP variants (Suzuki et al. 2012, Costantini et al. 2013). However, these efforts are complicated by the observation that, despite no obvious structural role for the cysteines, mutation of cysteines to most other amino acids decreases FP fluorescence brightness or results in a dark protein (Jain et al. 2001).

The currently available disulfide-resistant FP options do not cover many wavelengths and tend to be relatively dim. The mFruit FPs are relatively bright, but have been observed in aggregate-like structures (Costantini et al. 2013, Snapp 2005, Yanushevich et al. 2002). As a consequence, mCherry and other mFruits have been thought to disrupt secretory pathway organelle structures (Costantini et al. 2013). We revisit these observations and reinterpret this phenomenon in this study. More commonly, many FPs are prone to non-covalent dimerization. To engineer monomeric FPs, many FPs have been extensively mutated to disrupt native dimeric and tetrameric tendencies. In GFP-derived FPs, the A206K mutation robustly prevents dimerization at the hydrophobic interface of the β-barrel (Zacharias et al. 2002). Popular red FPs (RFPs), including DsRed, TagRFP, and tdTomato (Shaner et al. 2004, Matz et al. 1999, Merzlyak et al. 2007) were originally isolated as dimeric or tetrameric proteins from Anthozoa corals. Efforts by several research groups have sought to engineer more monomeric RFPs by disrupting the dimerizing protein interfaces (Shaner et al. 2004, Bevis et al. 2002). We, and others, have examined the monomeric characteristics of FPs in live cells and have identified circumstances where previously characterized monomeric FPs (mFPs) are prone to non-covalent interactions (Merzlyak et al. 2007, Lam et al. 2012, Costantini et al. 2012, Shemiakina et al. 2012). Furthermore, some RFPs, like mNeptune, develop significant pools of dead-end products of chromophore formation that happen to fluoresce green (Morozova et al. 2010), a highly undesirable characteristic for imaging multiple FPs.

Unfortunately, many popular FPs contain features that we hypothesized would be suboptimal for use in the distinct chemical environments of cellular organelles. In particular, many FPs contain cysteines and consensus N-linked glycosylation sequences and these may adversely impact FPs and associated reporters. In this study, we investigated these issues and sought to identify several FP color variants for use in a variety of cellular environments. To identify suitable FPs for multiple color labeling strategies to compliment sfGFP, we turned our attention to blue FPs (BFPs). In this study, we have engineered and improved blue (EBFP2), cyan (Cerulean), yellow (Venus) and green (sfGFP) (Pedelacq et al. 2006, Ai et al. 2007, Rizzo et al. 2004, Nagai et al. 2002) for diverse cellular environments to create a toolbox of inert FPs suitable for quantitative imaging of fluorescent fusion proteins in live cells.

Materials and Methods

Chemicals

Dithiothreitol (DTT; Fisher Scientific, Pittsburgh, Pa.) was diluted to the indicated concentrations from a 1 M stock solution in dH$_2$O. N-ethylmaleimide (NEM; Acros Organics, Thermo Fisher Scientific, Rockford, Ill.) was diluted to indicated concentrations from a 2 M stock in dH$_2$O.

Mammalian Plasmids

EBFP2, Cerulean, sfGFP, and Venus were previously described (Pedelacq et al. 2006, Ai et al. 2007, Rizzo et al. 2004, Nagai et al. 2002). Oxidizing-resistant EBFP2 and sfGFP contain cysteine to serine mutations using standard site directed mutagenesis procedures. Optimized oxCerulean, oxCerulean3, moxNeonGreen, and oxVenus were synthesized by GenScript (Piscataway, N.J.) and included cysteine to serine mutations, superfolder mutations, and were human codon optimized. To create cytoplasmic and ER-localized reporters, FP encoding sequences were amplified using primers listed in Table 1-1. FP fragments were cloned into the AgeI/NotI sites of the pEGFP-N1 plasmid (Clontech, Mountain View, Calif.) or pER-mRFP (Snapp et al. 2006) creating ER-FPs. To produce the GalT GC marker, cytoplasmic —N1 constructs were digested with SacI/AgeI and inserted into —N1 vector containing the GalT signal anchor (amino acids 1-61). FP fusions with actin or tubulin were generated from parental C1 pEGFP-actin (Clontech) and pEGFP-tubulin (Clontech) vectors. Vectors were digested with NheI/BglII. FP fragments were then cloned into NheI/BglII sites. To investigate specific amino acid substitution consequences on FP fluorescence, reverting mutations were reintroduced into FPs using designated primers (Table 1-1). All constructs were confirmed by sequencing.

TABLE 1-1

List of primers.

Mammalian cloning

ER-FP

| | | |
|---|---|---|
| sfGFP/oxGFP/EBFP2/oxBFP | F5' | GCAATGGGCGGTAGGCG (SEQ ID NO: 16) |
| | R5' | GATCGCGGCCGCGTTACAATTCATCCTTATTAAGTTTGTGCCC (SEQ ID NO: 17) |
| Cerulean/oxCerulean | F5' | GATCACCGGTCGTGAGCAAAGGAGAGGAACTGTTC (SEQ ID NO: 18) |
| | R5' | GATCGCGGCCGCTTACAGCTCGTCCTTCTTATACAGCTCGTCCATCCC (SEQ ID NO: 19) |
| Venus/oxVenus | F5' | GATCACCGGTCGCCACCATGGTGTCTAAAGGCGAG (SEQ ID NO: 20) |
| | R5' | GATCGCGGCCGCTTACAGCTCGTCCTTCTTATACAGCTCATCCATTCC (SEQ ID NO: 21) |

Cyto-FP

| | | |
|---|---|---|
| sfGFP/oxGFP/EBFP2/oxBFP | F5' | GCAATGGGCGGTAGGCG (SEQ ID NO: 22) |
| | R5' | GATCGCGGCCGCTTAATTAAGCTTGTGCCC (SEQ ID NO: 23) |
| Cerulean/oxCerulean | F5' | GATCACCGGTCGCCACCATGGTGAGCAAAGGAGAGGAAC (SEQ ID NO: 24) |
| | R5' | GATCGCGGCCGCTTACTTGTACAGCTC (SEQ ID NO: 25) |
| Venus/oxVenus | F5' | GATCACCGGTCATGGTGTCTAAAGGCGAG (SEQ ID NO: 26) |
| | R5' | GATCGCGGCCGCTCACTTATACAGCTCATC (SEQ ID NO: 27) |

FP-actin/tubulin

| | | |
|---|---|---|
| sfGFP/oxGFP/EBFP2/oxBFP | F5' | ATCCGCTAGCGCTACCGGTCGCCACCATGGTGAGCAAGGGCGAGG (SEQ ID NO: 28) |
| | R5' | CTCGAGATCTGAGTCCGGACTTGTACAGCTCGTCCATGCCG (SEQ ID NO: 29) |
| Cerulean3/oxCerlean3 | F5' | ATCCGCTAGCGCTACCGGTCGCCACCATGGTGTCAAAGGGCGAAGAGC (SEQ ID NO: 30) |
| | R5' | CTCGAGATCTGAGTCCGGACTTATACAGCTCGTCCATCCCCAG (SEQ ID NO: 31) |
| Venus/oxVenus | F5' | ATCCGCTAGCGCTACCGGTCGCCACCATGGTGTCTAAAGGCGAGGAACTG (SEQ ID NO: 32) |
| | R5' | CTCGAGATCTGAGTCCGGACTTATACAGCTCATCCATTCCCAGGG (SEQ ID NO: 33) |

TABLE 1-1-continued

List of primers.

Mammalian cloning

| | |
|---|---|
| mNeonGreen/moxNeonGreen | F5' ATCCGCTAGCGCTACCGGTCGCCACCATGTCCTCAAAGGGAGAAGAAGACAAC (SEQ ID NO: 34) |
| | R5' CTCGAGATCTGAGTCCGGACTTATACAGTTCGTCCATCCCCATCAC (SEQ ID NO: 35) |
| Epitope tag ER-FP | F5' GATCACCGGTCTACCCATACGACGTC (SEQ ID NO: 36) |
| | R5' GATCACCGGTAGCGTAGTCTGGGAC (SEQ ID NO: 37) |
| ER-split GFP | R5' GATCGCGGCCGCTTACAGCTCGTCCTTCTGCTTGTCGGC (SEQ ID NO: 38) |

Site-directed mutagenesis

| | |
|---|---|
| EBFP2 | C70S-5' CGGCGTGCAGTCGTTCGCCCGCTAC (SEQ ID NO: 39) |
| | C70A-5' GAGCCACGGCGTGCAGGCCTTCGCCCGCTACCCC (SEQ ID NO: 40) |
| | C70V-5' GAGCCACGGCGTGCAGGCCTTCGCCCGCTACCCC (SEQ ID NO: 41) |
| | F99S-5' CAGGAGCGCACCATCTCCTTCAAGGACGACGGC (SEQ ID NO: 42) |
| | V163A-5' GAACGGCATCAAGGCCAACTTCAAGATCCGC (SEQ ID NO: 43) |
| sfGFP | C48S-5' CCCTGAAGTTCATCAGTACTACCGGCAAGCTGCCC (SEQ ID NO: 44) |
| | C70S-5' CGGCGTGCAGTCGTTCAGCCGCTAC (SEQ ID NO: 45) |
| moxNeonGreen | C567T-F5' CTTTTGCTAAGCCTATGGCTGCAAAC (SEQ ID NO: 46) |

Monomerizing V206K

| | |
|---|---|
| EBFP2 | 5' GAGCACCCAGTCCAAGCTGAGCAAAGAC (SEQ ID NO: 47) |
| Cerulan3/oxCerulean3 | 5' GTCCTTAGACAGCCTGGACTGATAGCTC (SEQ ID NO: 48) |
| Venus/oxVenus | 5' GAGCTATCAGTCCAAGCTGTCTAAGGAC (SEQ ID NO: 49) |

Bacterial cloning

| | |
|---|---|
| sfGFP/oxGFP/EBFP2/oxBFP | F5' GATCCCATGGGTATGGTGAGCAAGGGCGAGGAG (SEQ ID NO: 50) |
| Cerulean/oxCerulean | F5' GATCCCATGGGTATGGTGAGCAAGG (SEQ ID NO: 51) |
| Venus/oxVenus | F5' GATCCCATGGGTATGGTGTCTAAAGGC (SEQ ID NO: 52) |
| moxNeonGreen | F5' GATCCCATGGGTATGTCCTCAAAGGG (SEQ ID NO: 53) |

Bacterial Cloning, Expression and Protein Purification

FP sequences were amplified using primers listed in Table 1-1. FP fragments were cloned into pEcoli-Cterm 6×HN vector (Life Technologies, Grand Island, N.Y.) at NcoI and PstI restriction sites. Vectors were expressed in CodonPlus competent, BL21 RP host cells (Stratagene, La Jolla Calif.). 5 ml cultures were grown at 37° C., 225 rpm overnight in LB under of chloramphenicol and ampicillin drug selection. 1 ml of overnight cultures were added to 50 ml of drug free LB for 2 h at 37° C., 225 rpm. For induction, 1 mM IPTG was added to cultures, and returned to 37° C., 225 rpm shaker for 4 h. Cultures were pelleted at 3000 rpm for 15 min at 4° C. For protein purification procedure refer to manufactures protocol for His60 Ni Superflow™ Resin & Gravity Column manual (Life Technologies). Peri-oxGFP was generated using the same cloning strategy as previously described peri-sfGFP (Aronson et al. 2011).

Cell Culture and Transfection

U-2 OS (ATCC HTB-96), HeLa (ATCC CCL-2), and MDCK (ATCC CCL-34) cells were routinely cultured in RPMI-1640 medium (Mediatech, Manassas, Va.), supplemented with 5 mM GlutaMAX (Life Technologies), penicillin/streptomycin (Invitrogen, Carlsbad, Calif.), and 10% heat inactivated fetal bovine serum (Hyclone from Thermo Fisher Scientific) at 37° C. in 5% $CO_2$. All constructs were transiently transfected for 16-20 h into cells using Lipofectamine 2000 (Life Technologies) according to the manufacturer's instructions. HeLa cells with stable expression of GalT-FPs were generated and maintained using G418 (Geneticin, Live Technologies) selection.

Live Cell Fluorescence Imaging

For imaging experiments, cells were grown in 8 well LabTek coverglass chambers (Nunc, Rochester, N.Y.). Cells were imaged in phenol red-free RPMI-1640 freshly supplemented with 10 mM Hepes (Thermo Fisher Scientific) and 10% fetal bovine serum. To increase organelle pH, when indicated, cells were incubated in media containing 20 mM $NH_4Cl$ and no Hepes for 3 h at 37° C. before imaging. Live cells were imaged on a 37° C. environmentally controlled chamber of a confocal microscope system (Zeiss LSM-5 LIVE microscope with Duoscan attachment; Carl Zeiss MicroImaging, Inc., Thornwood, N.Y.) with a 63X/1.4 NA oil objective and a 405 nm 50 mW diode laser with a 415-505 nm bandpass or 510 nm longpass filter for EBFP2 and 415-475 nm bandpass or 420 nm longpass filter for Cerulean, or a 489 nm 100 mW diode laser with a 520-555 nm bandpass filter for Venus and 495-555 and 520-555 nm bandpass filter for GFP or 561 nm diode laser with a 565 nm longpass filter for mCherry. Image analysis and composite figures were prepared using ImageJ (National Institutes of Health; Bethesda, Md.), Photoshop CS4 and Illustrator CS4 software (Adobe Systems, San Jose, Calif.). Live cell images were acquired using an Axiovert-200 widefield fluorescence microscope (Carl Zeiss Microimaging Inc.) with a 63X/1.4 NA oil immersion objective lens, a Retiga-2000 camera (QImaging, Surrey, BC Canada), and 470/40 nm excitation, 525/50 nm emission bandpass filter for Alexa Fluor 488, 565/30 nm excitation, or 365 nm excitation, 445/50 nm emission bandpass filter for BFP. Images were acquired with QCapture software.

Immunoblots and Co-Immunoprecipitation

Total cell lysates for immunoblotting were prepared in 1% SDS, 0.1 M Tris, pH 8.0 with 100 mM DTT (reducing conditions) or no DTT (nonreducing conditions) using cells in 24-well plates at 80-90% confluence. For the reducing and nonreducing immunoblots, cells were first treated with 20 mM NEM in phosphate buffered saline (PBS) for 15 min at room temperature. Proteins were separated using either 6 or 12% Tris-tricine gels, transferred to nitrocellulose, probed with the indicated antibodies, and developed using enhanced chemiluminescent reagents (Pierce, Rockford, Ill.), and exposed to X-ray film. Antibodies used included anti-GFP (generous gift from Ramanujan S. Hegde, Laboratory of Molecular Biology, Cambridge, UK), anti-GAPDH (catalogue number SC25778, 1:5,000 Santa Cruz Biotechnology, Dallas, Tex.) and horseradish peroxidase-labeled anti-rabbit secondary antibodies (Jackson Immunoresearch Laboratories, West Grove, Pa.). For co-immunoprecipitation analyses, cells were cultured in six-well plates were washed twice with PBS and lysed with Triton lysing buffer (1% Triton X-100, 50 mM HEPES, pH 7.4, 100 mM NaCl). Lysis buffers contained EDTA-free protease inhibitor cocktail (Roche, Indianapolis, Ind.). Lysates were clarified for 10 min at maximum speed in a microcentrifuge at 4° C. and incubated for at least 2 h at 4° C. with protein A agarose beads (Bio-Rad Laboratories, Hercules, Calif.) plus the indicated primary antibody. Beads were washed four times in IP lysing buffer and once in $dH_2O$, eluted in SDS-PAGE sample buffer, and analyzed on 6% SDS tricine gels, followed by immunoblot.

Immunofluorescence

Cells were fixed with freshly diluted 3.7% formaldehyde in PBS at room temperature for 15 min and permeabilized with 0.1% Triton X-100 in PBS. Blocking was performed with 10% fetal bovine serum in PBS for 30 min. Subsequently, cells were labeled with anti-GFP, anti-GM130 (BD Transduction Laboratories catalogue number 610823, 1:500 BD Biosciences, San Jose, Calif.), anti-β COP (Lippincott-Schwartz et al. 1995) (Affinity Bioreagents catalogue number PA1061, 1:500) or anti-LAMP1 (catalogue number H4A3-c 1:500, DSHB) (Chen et al. 1985) followed by Alexa Fluor 488 or 555 (as appropriate) conjugated anti-rabbit IgG secondary antibody (catalogue numbers A11008 and A21428 respectively, both used at 1:500, Life Technologies).

Relative and Mean Fluorescence Intensity Quantification

The relative fluorescence intensity of ER-EBFP2 and ER-oxBFP (FIG. 6) was measured in transiently expressing U-2 OS cells. Images were acquired using identical imaging parameters. At least five fields of view were captured for each condition on three separate days. Images were analyzed with ImageJ software. To measure a cell mean fluorescent intensity (MFI), first the cell nucleus was excluded and detectable fluorescence signal was selected using ImageJ threshold. The average MFI values were plotted using GraphPad Prism software. To measure and compare GalT-FP levels accumulated in the ER (FIG. 11), cells were fixed and stained, as above with anti-GFP followed by Alexa Fluor 555 conjugated anti-rabbit IgG secondary antibody. Images of the anti-Alexa Fluor 555 distributions were captured using identical imaging conditions and then analyzed using ImageJ. Regions (10×10 pixels) near the GC were measured for MFI and then values were plotted using GraphPad Prism software.

Protein Characterization

Absorbance was measured using a Hitachi U-2000 spectrophotometer (Hitachi High Technologies, Schaumburg, Ill.). Excitation and emission spectra were measured with a FluoroMax-3 spectrofluorometer (Horiba/Jobin Yvon, Edison, N.J.). Purified protein samples were measured in PBS at room temperature. To determine extinction coefficients and quantum yields, absorbance and fluorescence of the new fluorescent variants were compared with that of parental proteins. To assess photobleaching sensitivity under comparable imaging parameters, oxFPs and parental FPs were transiently expressed in U-2 OS cells. Cells were imaged using standard live cell imaging conditions. Images were acquired at 5 frames/s for 400 frames.

Statistical Analysis

Prism software (GraphPad Software, San Jose, Calif.) was used to compare the different conditions using two-tailed Student's t-tests. For higher stringency, differences were not considered significant for p values >0.01.

Results

ER-Localized FPs Form Inappropriate Disulfide Bonds

Figure 2:
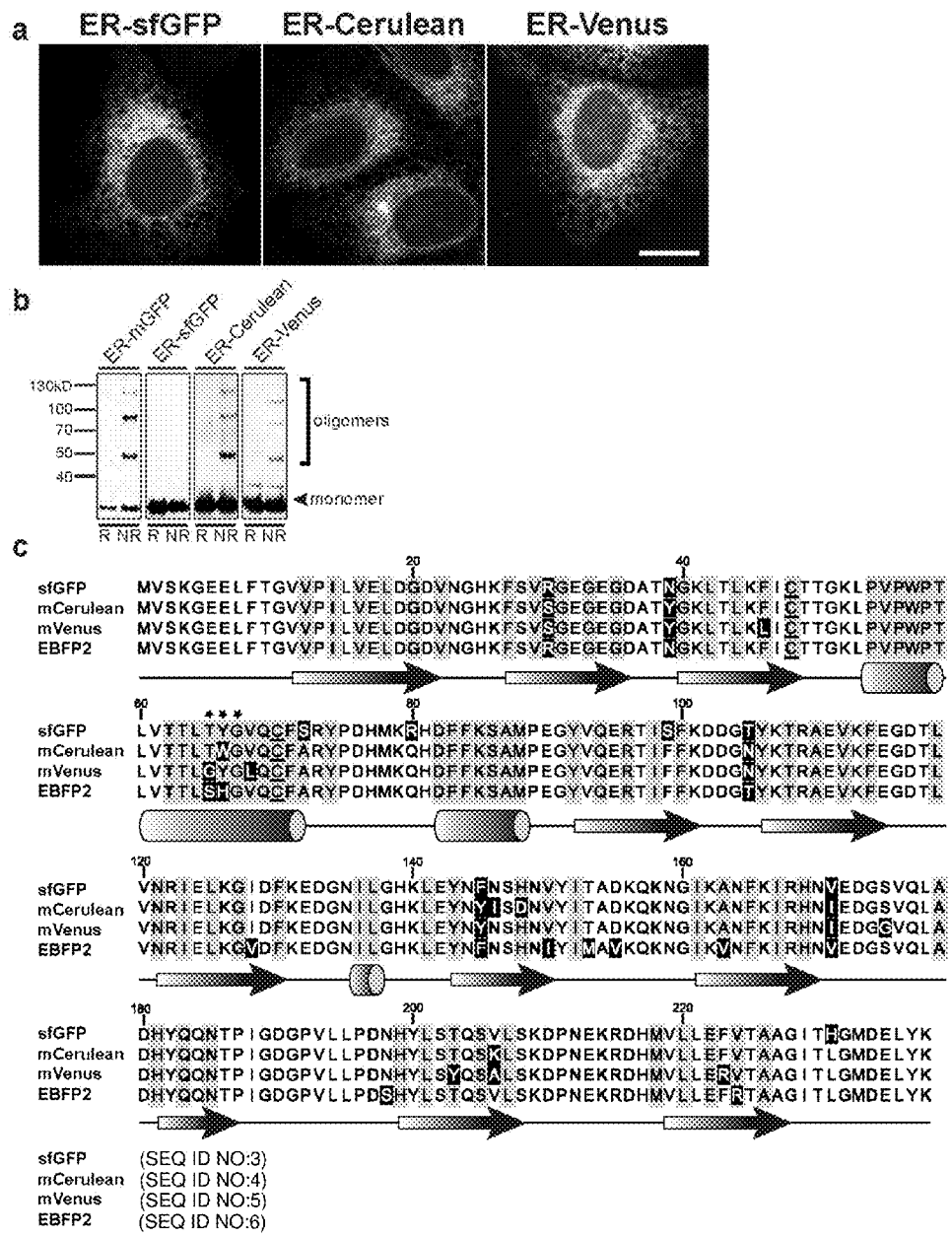
FIG. 2. ER localized-FPs. (a) Representative image of transiently transfected U-2 OS cells expressing ER-sfGFP, -Cerulean, or -Venus, scale bar is 10 µm. (b) Immunoblot illustrates the tendency of ER-Cerulean and -Venus to oligomerize under NR conditions. (c) Amino acid sequence alignment and secondary structure of sfGFP, Cerulean, Venus and EBFP2. FP sequences are shown with the relative location of amino acids with secondary structures. Grey shading specifies inward facing residues within a correctly folded 11-β-strand barrel. Underlined residues denote location of cysteine residues, black highlights/white font denotes location of superfolder and cycle-3 mutations, and asterisk (*) identifies chromophore-forming residues.
Figure 3:
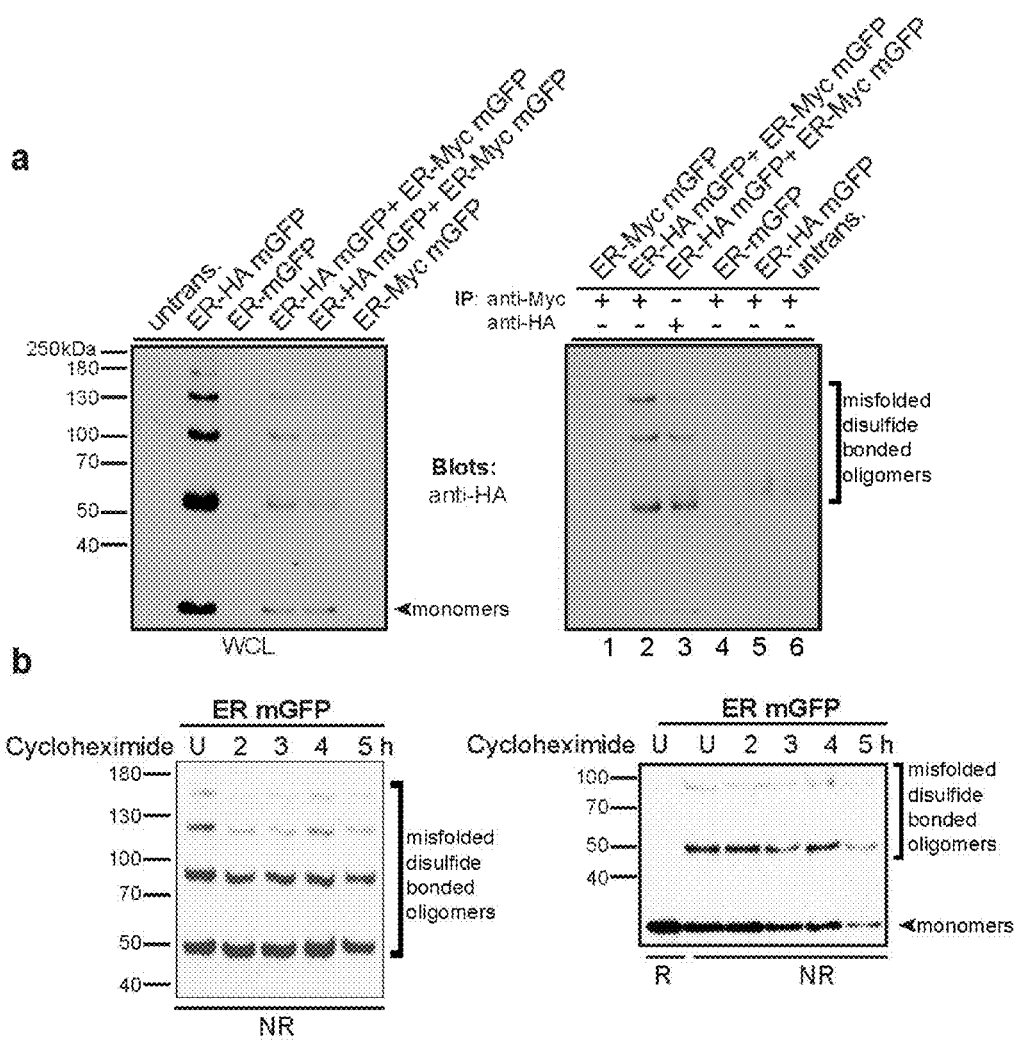
FIG. 3. FP Interchain disulfide bonds. (a) Immunoprecipitation (IP) of U-2 OS cells expressing and co-expressing epitope-tagged (HA or Myc) versions of ER-mGFP. IP with anti-Myc antibody of whole cell lysates (WCL) of cells transiently co-expressing ER-HA-mGFP and -myc-mGFP (Lane 2) with anti-HA immunoblot indicate higher molecular weight bands correspond to the formation interchain disulfide bonds between GFP molecules. (b) U-2 OS cells transiently transfected with ER mGFP overnight and then treated (or untreated (U)) for indicated times with 50 µg/ml cycloheximide, treated with NEM 20 min before lysis, separated by SDS-PAGE, and immunoblotted with anti-GFP. There is no significant decrease or shift in higher molecular weight interchain disulfide bonded species (left) or the ratio of monomeric and dimeric species (right).

Our overarching goal was to identify or develop a palette of FPs suitable for multi-color imaging of fusion proteins in the secretory pathway. Previously, we established that the cysteines in sfGFP (SEQ ID NO:3) are resistant to disulfide bond formation in oxidizing environments (Aronson et al. 2011). To test additional colors of FPs, we began with the blue FP, EBFP2 (Ai et al. 2007) (SEQ ID NO:6). It also contains the superfolder mutations. Therefore, we hypothesized it would also be resistant to disulfide bond formation. We directed EBFP2 to the ER of the mammalian secretory pathway with the prolactin signal sequence fused upstream of the FP and a robust ER-retrieval motif (amino acid residues, -KDEL; SEQ ID NO:54), to the extreme C-terminus (FIG. 1, Panel a). When ER-EBFP2 was expressed in U-2 OS cells, we observed fluorescence in a typical ER tubular network distribution (FIG. 1, Panel b). Similar results were observed for ER-Cerulean and ER-Venus (FIG. 2, Panel a). However, an immunoblot revealed a significant portion of EBFP2, under non-reducing conditions, migrated as multiple higher molecular weight species, in contrast to an expected single monomeric size (FIG. 1, Panel c, oligomers). Non-reducing immunoblot results of lysates of cells expressing ER-mGFP, -Cerulean and -Venus also produced higher molecular weight bands (FIG. 2, Panel b). The molecular weights observed suggest the formation of covalent oligomers corresponding to FP dimers, trimers, and higher oligomers. Immunoprecipitation confirmed that the higher molecular weight species were composed of inter-chain disulfide bonded FP homo-oligomers (FIG. 3, Panel a, Lane 2). Thus, the cysteines of many commonly used GFP-derived FPs contain are susceptible to form non-native covalent oligomers within the secretory pathway (FIG. 2, Panel c). Based on previously published structural data (Ormö et al. 1996, Yang et al. 1996), we hypothesize the inter-chain disulfide bonded FPs are unable to properly fold and consequently remain non-fluorescent. The pool of disulfide bonded FPs does not change to an appreciable degree over time (FIG. 3, Panel b), which suggests that these species are terminal products. More importantly, superfolder mutations are not sufficient insurance against disulfide bond formation by some GFP family members.

Optimization of EBFP2 for Oxidizing Environments

EBFP2 (SEQ ID NO:6) was previously evolved from EBFP (Yang 1998) and contains the sfGFP (SEQ ID NO:3) mutations (S30R, Y39N, N105T, Y145F, I171V and A206V), plus 8 additional amino acid substitutions for a total of 14 amino acid residue changes distinct from EGFP (Heim et al. 1995). We sought to engineer an inert EBFP2 suitable for the ER environment and further compared EBFP2 and sfGFP for differences that might account for resistance or susceptibility to disulfide bond formation. Sequence alignment analyses (FIG. 2, Panel c) revealed that two common GFP mutations (F99S and V163A) that were absent from EBFP2. These missing mutations, are included in the GFP variant termed "cycle-3" GFP (or αGFP (Patterson et al. 1997)) were identified using a DNA shuffling technique to introduce amino acid mutations, F99S, M153T and V163A (Crameri et al. 1996). We incorporated the missing two mutations and evaluated the susceptibility of forming covalent oligomers when localized to the ER. We found these mutations did not prevent oligomer formation (FIG. 1, Panel d), but we observed a significant reduction in the proportion of covalent oligomers compared to monomeric species.

Therefore, it appeared that we would need to mutate the two FP cysteine residues (C48 and 70). However, mutagenesis of the cysteines in the closely related EGFP decreased brightness with single cysteine mutations and rendered the protein dark upon mutating both cysteines (Jain et al. 2001). Similarly, when we mutated cysteines in mTagBFP into secBFP2 (Costantini et al. 2013), the resulting brightness was greatly diminished relative to parental mTagBFP, which was engineered from TagRFP (Subach et al. 2008).

Indeed, cysteine to serine substitutions diminished the fluorescent signal of the cysteine-less EBFP2 (Table 1-2). Reverse mutagenesis revealed that C70 was sensitive to mutagenesis and responsible for the decreased fluorescence. Cysteine is often more hydrophobic than its structure intuitively suggests (Chou et al. 1974). Thus, we considered more hydrophobic mutations. A valine mutation was better tolerated than the amino acid substitutions of serine or alanine. When expressed in the cytoplasm of cells, the C48S/C70V variant had lower relative brightness compared to the parental cysteine-containing EBFP2. In an attempt to restore fluorescence, we turned our attention to the missing F99S and V163A cycle-3 mutations. Additional rounds of mutagenesis revealed that the combination of C48S, C7OS and V163A resulted in a BFP with brightness comparable to parental EBFP2, without the problematic cysteine residues (Table 1-2).

Figure 4:
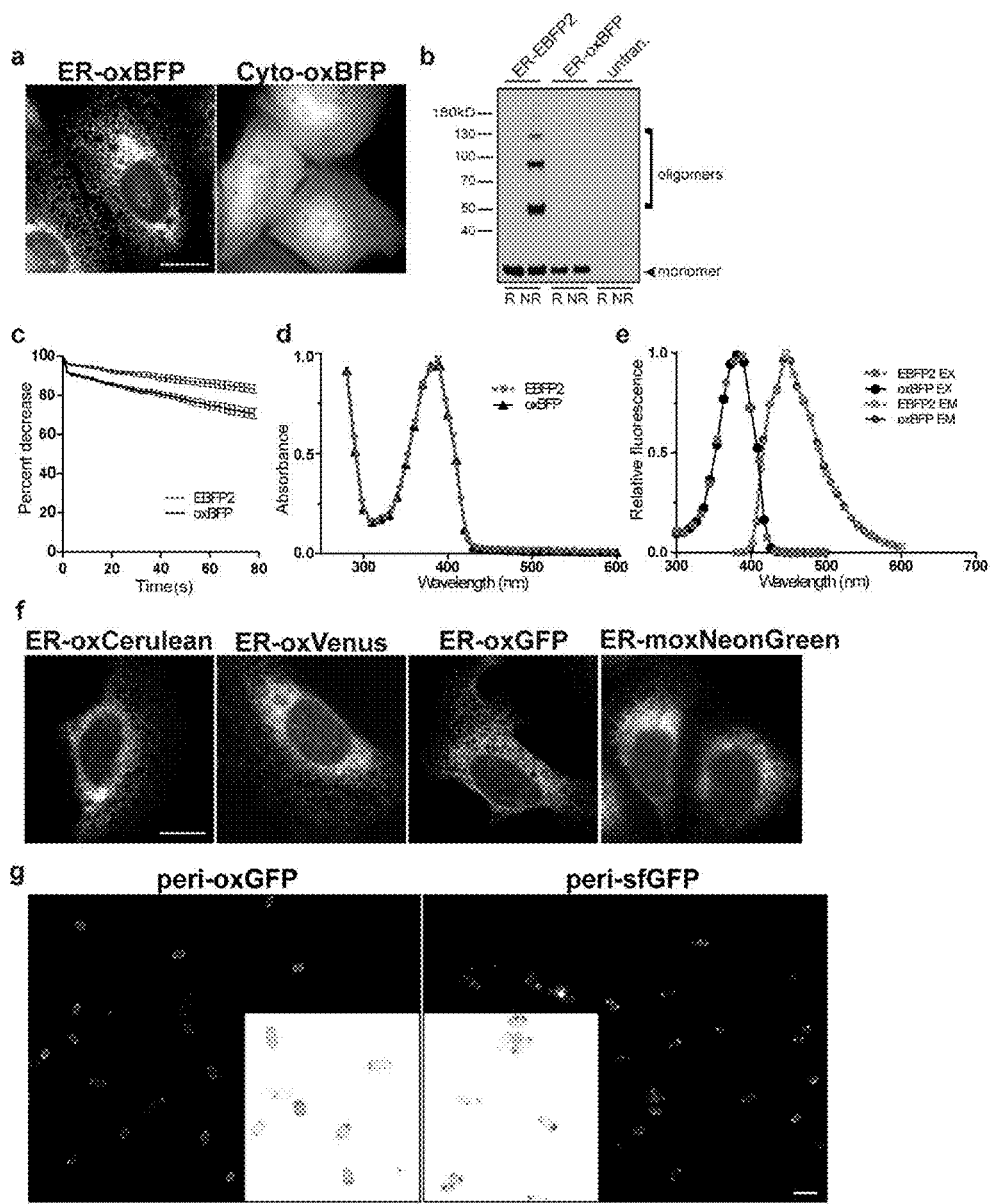
FIG. 4. OxFPs are fluorescent. (a) Representative image of Cyto-oxBFP and ER-oxBFP expressing U-2 OS cell, scale bar=10 µm. (b) Immunoblot of cells transfected with ER-EBFP2 or -oxBFP. Under non-reducing conditions, the optimized, cysteine-less oxEBPF2 does not form inappropriate disulfide bonds. (c) oxBFP (black line) maintains moderately comparable photostability properties under standard imaging conditions compared to EBFP2 (grey line). Optimized oxBFP variant (black data points) has comparable spectral characteristics to parental EBFP2 variant (grey data points). (d) Absorbance measurements and (e) fluorescence excitation (closed data points), emission (open data points). (f) Representative images of ER-oxCerulean, -oxVenus, -oxGFP or moxNeonGreen expressing U-2 OS cells. Scale bar is 10 µm. (g) oxGFP fluoresces homogenously throughout the periplasm of gram-negative bacteria (CodonPlus competent, BL21 RP). Cells were induced for 1 h with IPTG and then imaged. Inset thumbnails are enlarged and inverted for detail. Scale bar=1 um.

Importantly, the new BFP, termed oxBFP, is fluorescent within the cytoplasm and lumen of the ER and does not participate in non-native disulfide bonds (FIG. 4, Panels a and b). Spectral characterization of oxBFP was conducted to confirm that the spectral properties remained unchanged compared to the parental EBFP2. We observed a modest decrease in photostability under comparable imaging parameters (FIG. 4, Panel c). OxBFP maintained the absorbance (FIG. 4, Panel d), excitation, and emission (FIG. 4, Panel e) spectra of EBFP2, confirming the incorporated mutations did not affect the spectral properties of the FP.

TABLE 1-2

Overview of EBFP2 mutants and fluorescence intensities.

| Mutant | Relative mean fluorescence intensity |
| --- | --- |
| EBFP2 | ++++ |
| C48S, C70S | − |
| C48S | ++ |
| C70S | − |
| C70A | − |
| C70V | ++ |
| C48S, C70V | + |
| C48S, C70V, V163A (oxBFP) | ++++ |

A Palette of Oxidizing Environment-Optimized FPs

Figure 5:
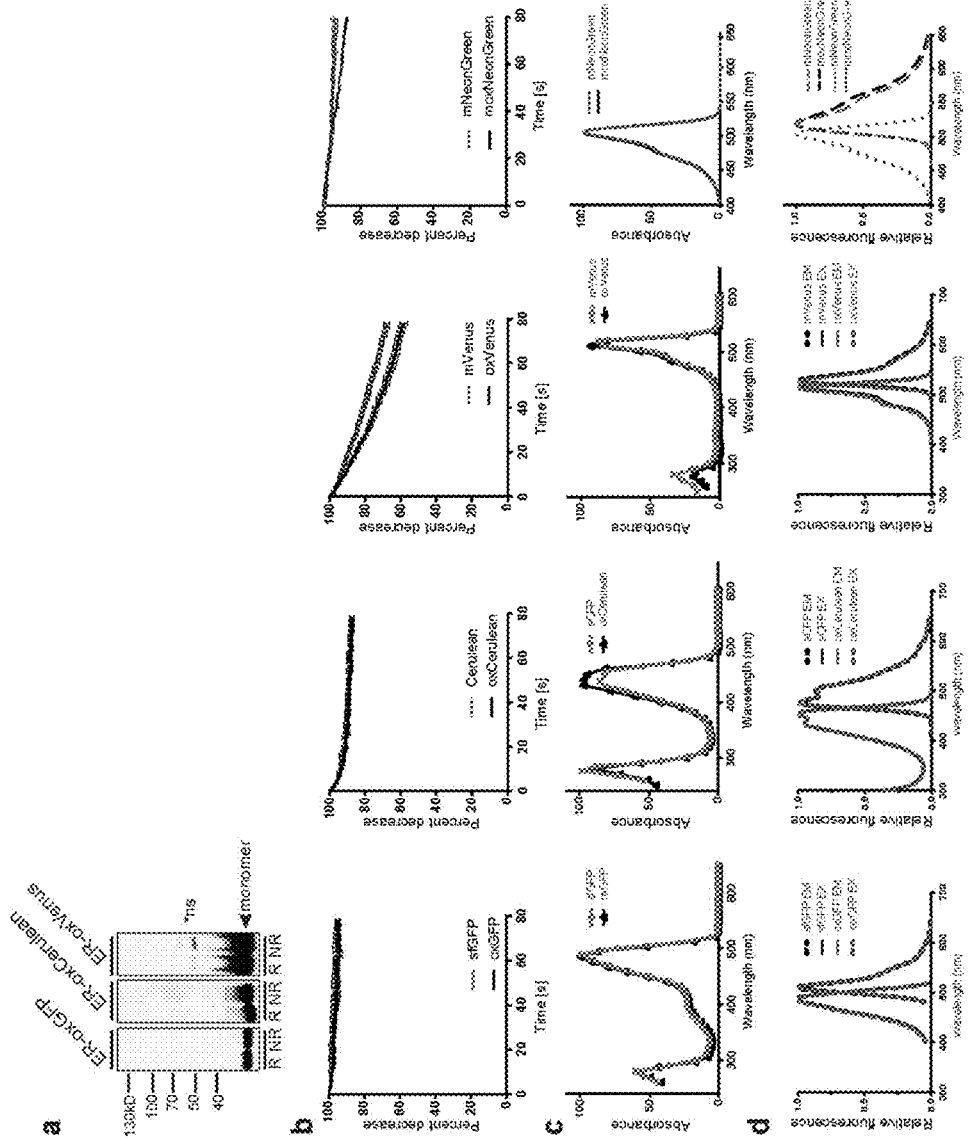
FIG. 5. oxFPs characterization. (a) Immunoblot of U-2 OS cells transfected with ER-oxGFP, -oxCerulean, or -oxVenus, under NR conditions, the optimized, cysteine-less FPs do not form inappropriate disulfide bonds. (b) Optimized, cysteine-less variants, oxFPs (black line) maintain moderately comparable photostability properties under standard imaging conditions compared to parental versions (grey line). OxFPs (black data points) have comparable spectral characteristics to parental variants (grey data points). (c) Absorbance measurements and (d) fluorescence excitation and emission.

To expand the available FP colors for oxidizing environments, we applied the same approach to Cerulean (SEQ ID NO:4) and Venus (SEQ ID NO:5) FPs by synthesizing versions that were human codon optimized and contained the sfGFP and cysteine to serine mutations to create oxCerulean and oxVenus. We also removed the cysteines from sfGFP to create, oxGFP. Although, our previous results established that the cysteines in the sfGFP were protected, we sought to create a GFP insusceptible to disulfide bond formation. In addition, we were able to create a cysteineless green alternative to GFP family members, moxNeonGreen, an oxidizing environment optimized variant of the recently described mNeonGreen (Shaner et al. 2013). We successfully expressed and localized the new FPs to the ER (FIG. 4, Panel f) and determined that the spectral characteristics of the cysteine-less FPs were comparable to the parental FPs (FIG. 5). Table 1-3 summarizes the spectral properties of the new palette of oxidizing-optimized oxFPs: blue oxBFP, green oxGFP, green moxNeonGreen, cyan oxCerulean, and yellow oxVenus.

In addition to the ER, other cellular compartments can be oxidizing, including the periplasm of gram-negative bacteria. We previously found that sfGFP fluoresces robustly in the periplasm of gram negative bacteria (Aronson et al. 2011). We tested the utility of oxGFP in the periplasm of bacteria and we found that oxGFP fluoresces equally well (FIG. 4, Panel g). We predict the other oxFP variants should also be useful for studies in the bacterial periplasm.

TABLE 1-3

Properties of oxidation-resistant optimized fluorescent proteins.

| Parent FP | oxFP | Absorbance Maximum, nm and ($\varepsilon^a$) | Fluorescence Maximum, nm and ($\varphi^b$) | Molecular Brightness$^c$ (Parent) |
|---|---|---|---|---|
| EBFP2 | oxBFP | 385 (31,000) | 448 (0.56) | 17 (18) |
| sfGFP | oxGFP | 486 (87,000) | 510 (0.58) | 50 (54) |
| Cerulean | oxCerulean | 435 (56,000) | 477 (0.41) | 23 (26) |
| Cerulean3 | moxCerulean3 | 434 (41,000) | 474 (0.87) | 36 (36) |
| Venus | oxVenus | 514 (89,000) | 526 (0.49) | 44 (53) |
| mNeonGreen | moxNeonGreen | 505 (111,000) | 520 (0.74) | 82 (93) |

$^a$Extinction coefficient ($M^{-1}$ $cm^{-1}$).
$^b$Quantum yield.
$^c$Brightness was calculated as a product of extinction coefficient and quantum yield and divided by 1,000.

Consequences of Disulfide Bond Formation

Figure 6:
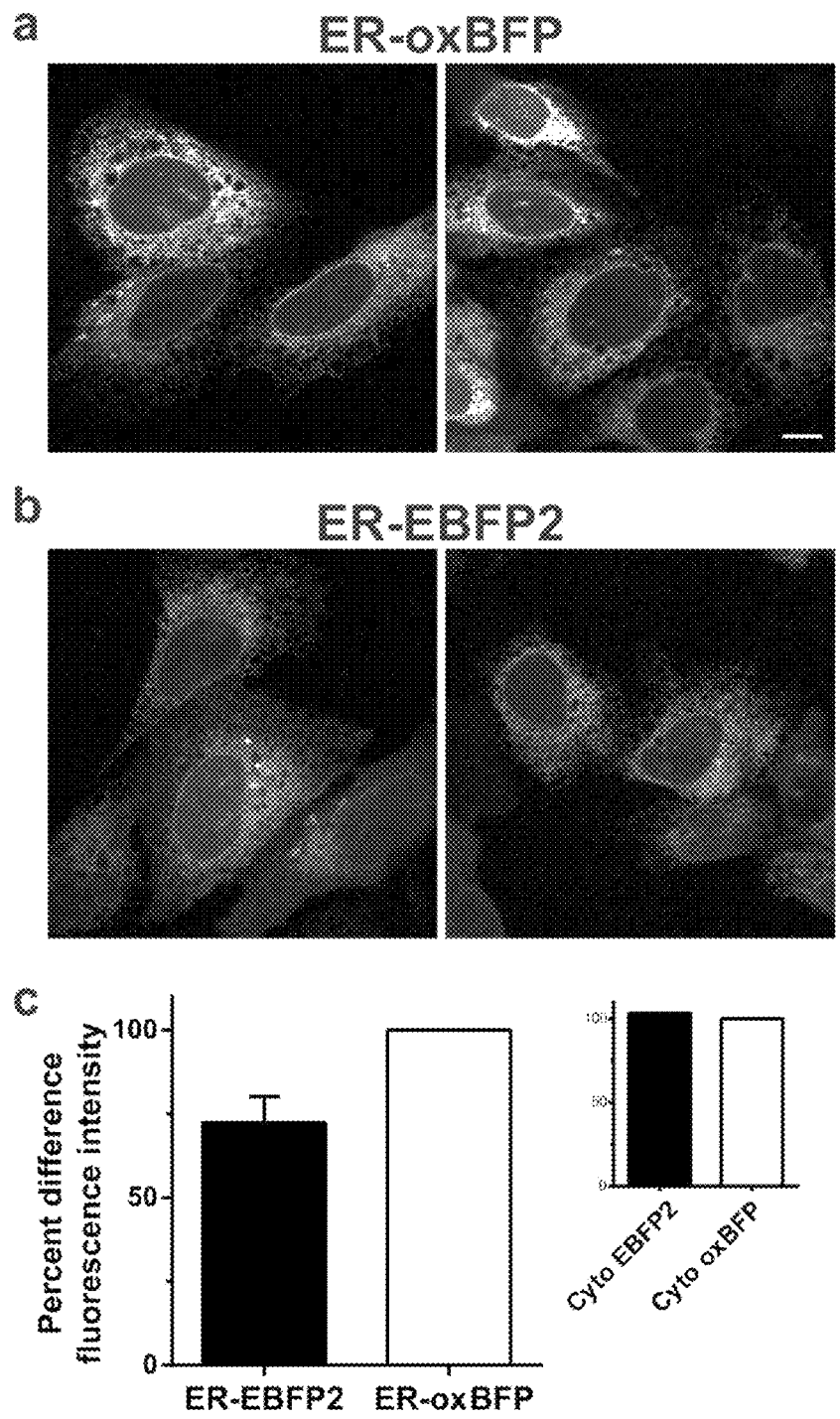
FIG. 6. ER-localized oxBFP has greater fluorescence intensity in oxidizing environments. Representative images taken with identical imaging conditions of live U-2 OS cells transiently transfected (16 h post-transfection) with (a) ER-oxBFP or (b) ER-EBFP2 illustrate the higher fluorescence level of the cysteine-less variant, scale bar is 10 µm. (c) Quantitation of the percent difference of relative mean fluorescent intensity of the ER fluorescence signal ER-EBFP2 has a ~27% decrease in brightness, total n=250 cells, (ER-EBFP2 73 cells, ER-oxBFP 72 cells, Cyto-EBFP2 43 cells and Cyto-oxBFP 62 cells).

The higher molecular weight bands observed by immunoblots (FIGS. 1, 2, and 4) established that significant fractions of non-optimized FPs misfold in oxidizing compartments. Comparisons of fluorescence intensity measurements revealed a decrease of fluorescence signal in cells transiently expressing the non-optimized FP variant. Cells expressing ER-EBFP2, the non-optimized FP, are visibly dimmer compared with ER-oxBFP (FIG. 6, Panels a and b). Evaluation of the relative fluorescence intensity of the optimized oxBFP with EBFP2 revealed a 27% reduction in the detectable fluorescence when EBFP2 was localized to the ER compared to ER-oxBFP (FIG. 6, Panel c). This measureable decrease in fluorescence signal was specifically a consequence of the oxidizing environment of the ER. When the two BFPs were localized to the cytoplasm, in the absence of disulfide formation, the BFPs exhibited nearly identical mean fluorescence intensities (FIG. 6, Panel c inset).

Figure 7:
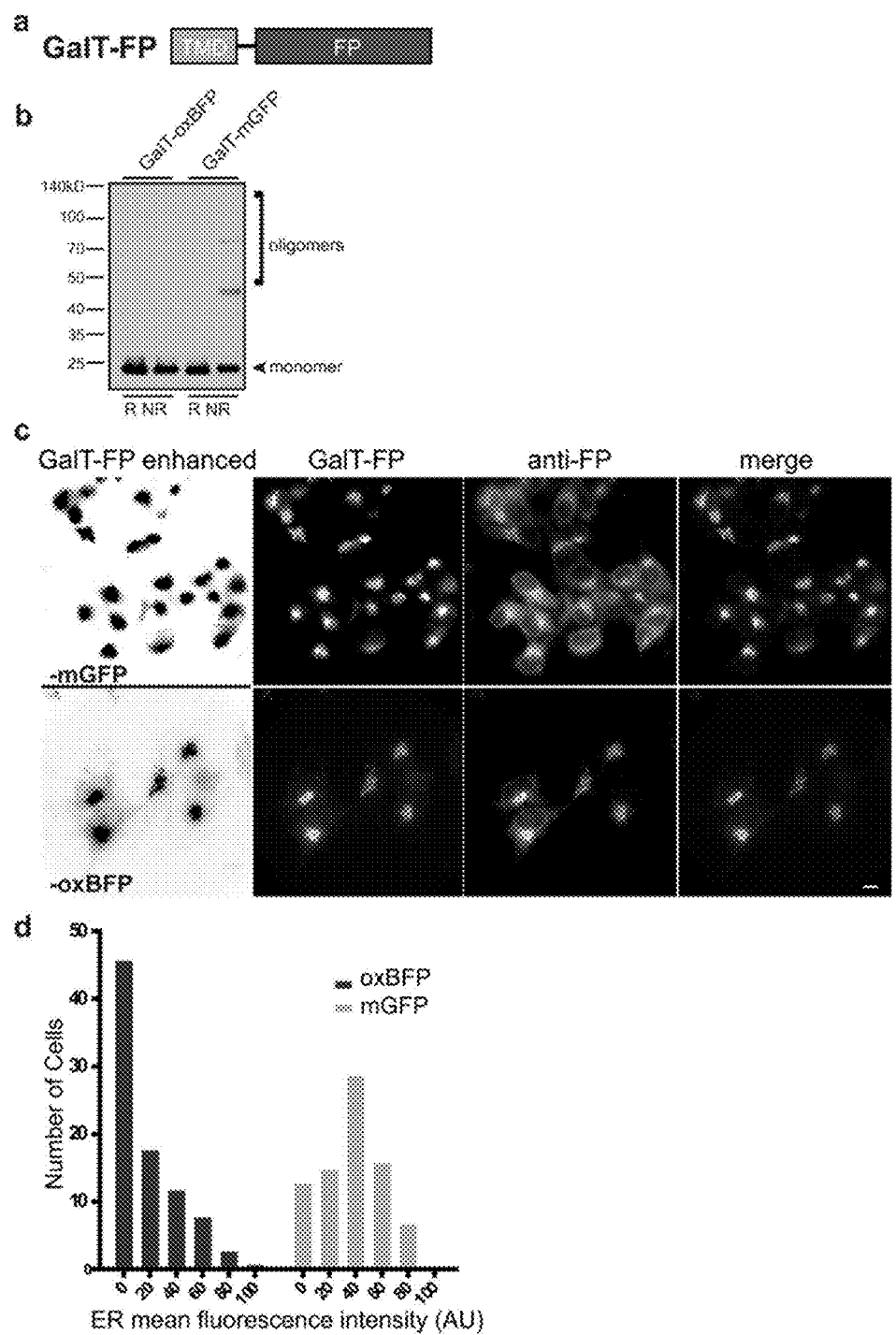
FIG. 7. Golgi complex-membrane localized mGFP forms inappropriate disulfide bonds and is inefficiently trafficked to the Golgi complex (GC). (a) Schematic of GC localized FP (GalT-FP) containing GalT transmembrane domain upstream of FP. (b) Immunoblot revealed the tendency of GalT-mGFP to form oligomers under NR conditions. Optimized, cysteine-less GalT-moxBFP does not form inappropriate disulfide bonds. (c) Representative images of HeLa cells transiently transfected with GalT-mGFP or -oxBFP. Immunofluorescence with anti-GFP revealed a significant fluorescently undetectable pool of GalT-mGFP in the ER. ER labeling by the FP is digitally enhanced with Levels tool in Photoshop in far left Panels. Note that weak ER is apparent in all of the oxBFP expressing cells, but rarely observed in mGFP expressing cells. Scale bar=10 µm. (d) Distribution of the ER fluorescence intensity values (mean fluorescence intensities of regions of anti-GFP staining proximal to the GC). n>80 cells collected from 11-13 fields per construct.

Both freely diffusing luminal and membrane localized nonoptimized FPs within the secretory pathway are prone to inappropriate disulfide bond formation. We localized an optimized and a nonoptimized FP to the GC with the 1,4-galactosyltransferase, GalT, signal anchor transmembrane domain (FIG. 7, Panel a). The tagged proteins are oriented with the FP in the lumen of the ER and GC (Cole et al. 1996). Non-reducing immunoblots revealed that GalT-mGFP forms covalent oligomers (FIG. 7, Panel b).

Figure 8:
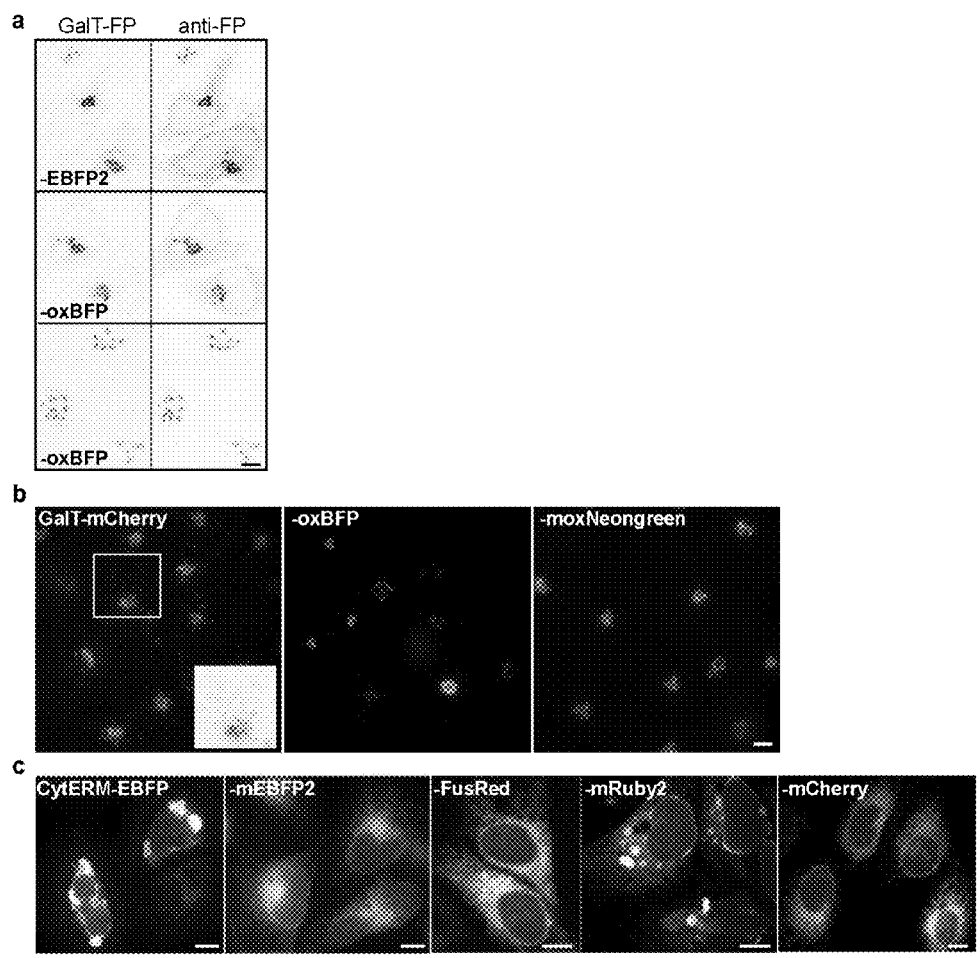
FIG. 8. FP non-covalent oligomers. (a) Transiently transfected HeLa cells expressing indicated GalT-FP constructs. (b) HeLa cells selected for stable expression of GalT-mCherry, -oxBFP, -sfGFP or moxNeonGreen. Inset, inverted image denoted by white box. (c) CytERM reporter reveals extensive organized smooth endoplasmic reticulum (OSER) structures in live cells expressing CytERM-EBFP2 and -mRuby2. The monomerizing A206K mutation prevents OSER formation. FusionRed (FusRed) and mCherry also exhibit normal ER patterns consistent with being monomeric. Scale bars equal 10 µm.

To investigate where the misfolded dark secretory pathway protein fusions localize, we compared where optimized and nonoptimized GalT-FP reporters localize in cells. GalT-mGFP or -oxBFP exhibit predominantly compact perinuclear fluorescence, consistent with GC localization (FIG. 7, Panel c). Yet, immunofluorescence (IF) of the same cells with anti-GFP antibodies revealed that a substantial dark pool of GalT-mGFP resides in the ER (FIG. 7, Panel c) of most expressing cells (FIG. 7, Panel d). Although GalT-oxBFP expressing cells also exhibit some ER fluorescence by IF: i) it is much less common, ii) in those cells, the ER is visible in the FP channel, too, especially when image levels are enhanced, and iii) each GC has a much higher mean fluorescence intensity (MFI) relative to the ER intensity. In contrast, GalT-mGFP-expressing cells have comparatively higher ER fluorescence and more modest GC fluorescence by IF, with little ER fluorescence intensity visible from the FP, even when image contrast levels are enhanced. GalT-EBFP2 expressing cells also frequently exhibit an ER pool visible only in immunofluorescence images (FIG. 8, Panel a).

These data suggest the in GalT-mGFP the inter-chain disulfide bonds that we observed via non-reducing immunoblots (FIG. 7, Panel b, oligomers) likely correspond to the non-fluorescent pool revealed by anti-GFP IF. Together, the representative images and quantitation indicate a substantial proportion of GalT-mGFP remains in the ER as non-fluorescent covalent oligomers, while GalT-oxBFP properly folds, fluoresces, and traffics to the GC. These examples establish the importance of using the inert oxFPs for studies of secretory compartments in cells.

Two-Color FP Pairs for Secretory Protein FP-Fusions

Commonly, dual color FP-fusion labeling approaches employ mCherry or another RFP in combination with a GFP. MCherry does not contain cysteine residues, is reportedly monomeric (Shaner et al. 2004), and it has been successfully expressed in oxidizing environments, including bacterial periplasm (Chen et al. 2005). Therefore, mCherry would be expected to be a suitable FP option for use in secretory protein fusions. However, for GC-localized membrane fusion proteins, we have previously found mCherry to be a potentially problematic choice, as mCherry fusions often localize to numerous punctate structures distinct from GFP family members fused to GalT (Costantini et al. 2013). Others have reported that mCherry protein fusions can aggregate (Landgraf et al. 2012), impair growth in yeast and development of tissues in *Xenopus laevis* (Shemiakina et al. 2012, Snaith et al. 2010). These issues motivated us to test the utility of our oxFPs for dual color labeling schemes, especially for labeling the GC.

Figure 9:
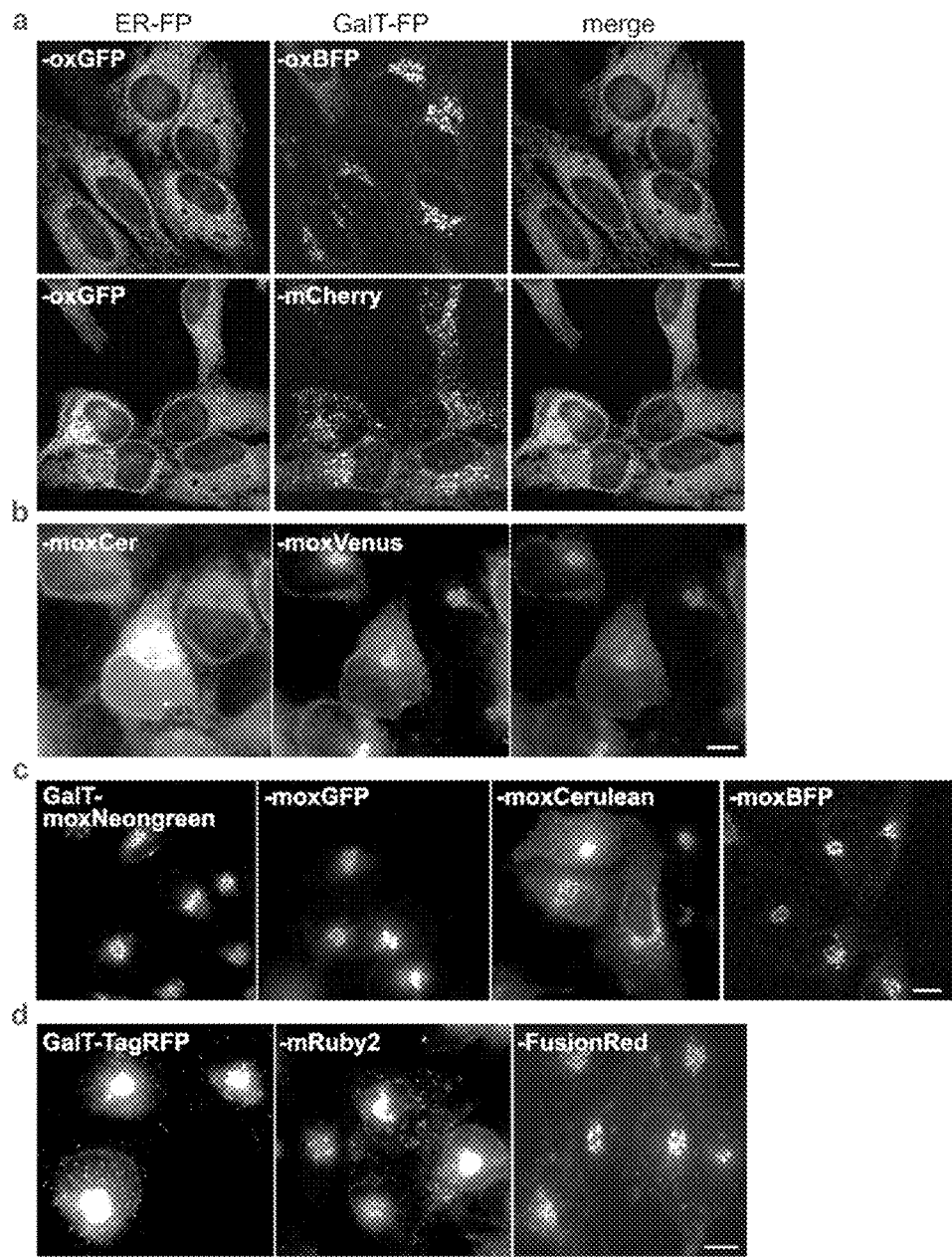
FIG. 9. Golgi complex-localized membrane fusions with oxBFP exhibit important differences relative to red FP fusions. Representative image of (a) HeLa cells transiently co-expressing ER-oxGFP and GalT-moxBFP or -mCherry. (b) Live cells expressing GalT-moxVenus and ER-moxCerulean3 are readily distinguishable and thus represent a useful pair of FPs for two color imaging in the secretory pathway of live cells. (c) Transiently transfected HeLa cells expressing GalT-moxBFP, -moxGFP, -moxNeonGreen or -moxCerulean3. (d) Live cells expressing GalT-TagRFP or GalT-mRuby2 exhibit both the GC and bright puncta throughout the cell, while GalT-FusionRed appears to primarily localize to GC structures. Scale bars=10 µm.

For comparison, we expressed GalT-oxBFP and -mCherry fusions in HeLa cells (FIG. 9, Panel a). Representative images show expected ER-oxGFP labeling of the ER network along with discretely GC-localized GalT-oxBFP. In contrast, GalT-mCherry fusions localized in a dispersed pattern of puncta throughout the cell. However, at lower expression levels, especially in stably transfected cells, a mixed puncta and GC distribution can be observed for GalT-mCherry (FIG. 8, Panel b). Thus, oxBFP appears to be a suitable FP for use in GC reporters.

The Propensity of FPs to Oligomerize

Since mCherry is a popular FP, we sought to carefully test the possibility that GalT-mCherry-might have a tendency to oligomerize and/or aggregate. If so, oligomers or aggregates could disrupt proper localization in the GC. We examined mCherry oligomerization using the live cell assay that we recently developed for assessing FP monomericity in cells. In addition, we also tested whether other FPs were sufficiently monomeric to avoid FP oligomerization artifacts (Zacharias et al. 2002, Snapp et al. 2003). We directly compared oxFPs and oxFPs modified with the A206K GFP monomerizing mutation using an abbreviated version of our CytERM assay (Costantini et al. 2012, Shaner et al. 2013). We found that EBFP2 and mTagBFP possess strong propensities to oligomerize and form organized smooth endoplasmic reticulum (OSER) whorl structures (Table 1-4) (FIG. 8, Panel c). The A206K mutation significantly diminished FP-FP interactions and whorl formation for oxBFP. Therefore, we subsequently monomerized all of our constructs to create monomeric oxidizing environment optimized (mox) FPs. The resulting constructs included moxGFP (SEQ ID NO:8, encoded by SEQ ID NO:7), moxCerulean (SEQ ID NO:10, encoded by SEQ ID NO:9), moxVenus (SEQ ID NO:12, encoded by SEQ ID NO:11), and mox BFP (SEQ ID NO:14, encoded by SEQ ID NO:13).

Based on our results, the tendency of GFP family members to dimerize does not appear to impact GC structure. Furthermore, we rarely observed OSER structures with CytERM-mCherry or for a newer RFP, FusionRed (Shaner et al. 2007) (FIG. 8, Panel c). Therefore, we consider oligomerization unlikely to explain the punctate structures observed in GalT-mCherry expressing cells.

Another RFP, CytERM-mRuby2 (Miyawaki et al. 2012), was highly prone to OSER formation (FIG. 8, Panel c). These data were quantified using the CytERM assay (Table 1-4). We note that the reported monomericity of mRuby2 was assessed for the parent protein, mRuby, by passing a solution of purified protein over a molecular sizing column (Lam et al. 2012, Kredel et al. 2009). As with another RFP, TagRFP, molecular sizing columns do not appear to be a robust method for determining the propensity of FPs to oligomerize in cells (Shcherbakova et al. 2012).

TABLE 1-4

Propensity of BFPs to oligomerize in mammalian cells.

| BFP | % Cells with OSER Structures (n = cells) |
|---|---|
| EBFP2 | 63.7 (138) |
| moxBFP | 0.9 (109) |
| mTagBFP | 43.5 (69) |

Monomeric oxFP Two-Color Pairs for Oxidizing Environments

Using our new moxFPs, we tested their suitability for use in GalT reporters and for dual color imaging pairs. GalT-moxVenus and ER-moxCer constructs, localized in patterns similar to that observed with oxGFP and oxBFP (FIG. 9, Panel b). Thus, the ox- and monomerized ox-FPs can be exploited for at least two different two color pairs for multi-color imaging. In addition, when expressed stably and transiently in cells, GalT-moxBFP, moxCerulean, moxGFP, and moxNeonGreen localized predominantly to compact perinuclear GC structures (FIG. 8, Panel b; FIG. 9, Panel c). We asked whether RFPs could be used for GC localization reporters by fusing the GalT domain to TagRFP, mRuby2 (Lam et al. 2012), and FusionRed (Shemiakina et al. 2012). The first two red FP fusions strongly resembled the mCherry GalT distribution while FusionRed predominantly localized in a GC pattern (FIG. 9, Panel d). Of these red FPs, only mCherry is cysteine-free. Thus, many RFPs appear to be suboptimal for use in the secretory pathway and even mCherry appears to be problematic when used with a GC-localized membrane protein. However, given the need for red FPs in multi-color imaging, the punctate distribution of GalT-mCherry merited further investigation before rejecting use of mCherry in the secretory pathway.

Figure 10:
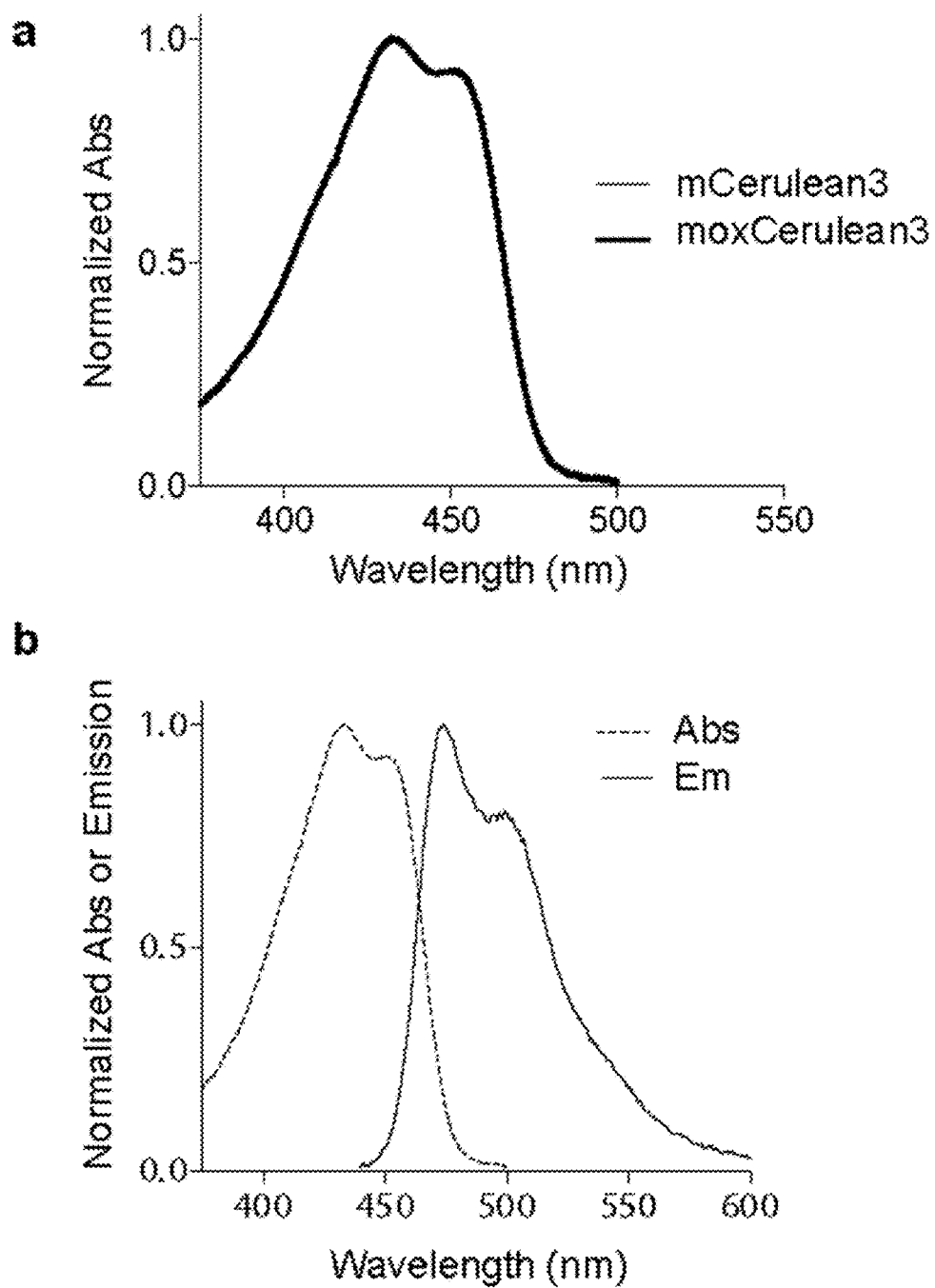
FIG. 10. Absorbance and emission spectra of purified moxCerulean3. (a) Normalized absorbance spectra of purified Cerulean3 and moxCerulean3. (b) Excitation and emissions spectra of moxCerulean3.

Importantly, upon closer examination of the GC distribution of the other GalT-moxFP fusions, we encountered a surprising result. GalT-moxCerulean and GalT-moxCerulean3 (an improved Cerulean variant) (Markwardt et al. 2011) also localized to both GC and punctate structures (FIG. 9, Panel c). As moxCerulean3 (Table 1-3 and FIG. 10) is closely related to other GFP family members, this result suggested a potential explanation for the punctate pattern of GalT-mCherry that we investigate in the next section.

GalT-mCherry Accumulates in Lysosomes

RFPs are essential reagents for cell biologists and they have many desirable properties, including brightness and illumination with longer less phototoxic wavelengths that are less prone to exciting autofluorescent substrates in cells. Several of the red FPs were evolved from inherently dimeric or tetrameric proteins. For fusion proteins, it is critical that the FP of choice not oligomerize. We (FIG. 8, Panel c) (Costantini et al. 2012) and others (Siegel et al. 2013, Wang et al. 2014) find that not all RFPs reported as monomeric perform as monomers in cells. We observed that mCherry only weakly oligomerizes (FIG. 8, Panel c and Table 1-4). Against this background, we sought to understand the behavior of GalT-mCherry.

Figure 11:
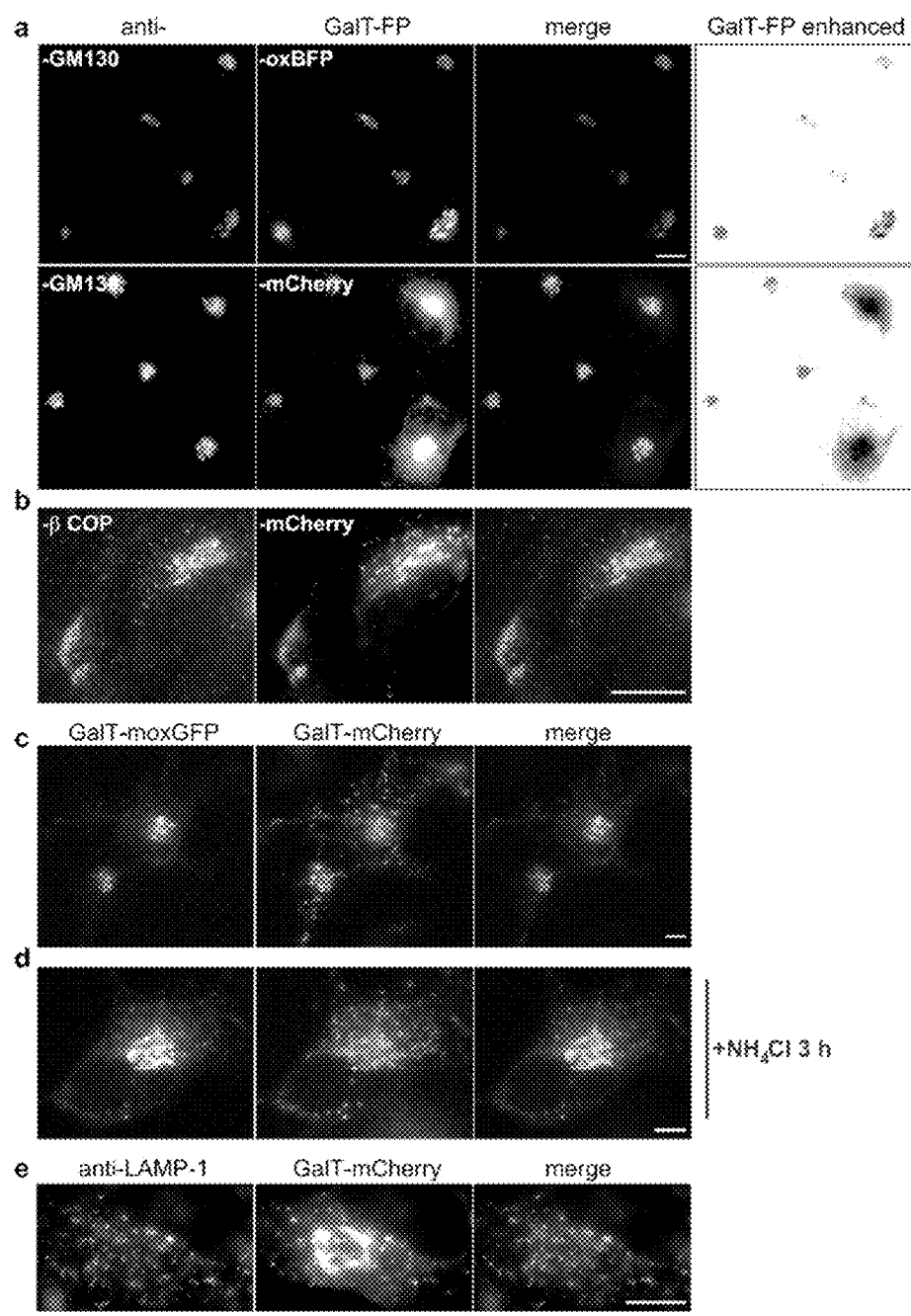
FIG. 11. GalT-mCherry puncta localize to lysosomes. (a) Fixed cells expressing GalT-oxBFP (upper Panels) or GalT-mCherry (lower Panels) and stained with the GC marker anti-GM130. Colocalization was observed for GalT-oxBFP, but cells expressing moderate levels of GalT-mCherry exhibit both GC colocalization, and bright puncta throughout the cell. (b) GalT-mCherry expressing HeLa cells fixed and stained for the GC and intermediate compartment marker β COP. The red puncta do not colocalize with the green β COP puncta. (c and d) HeLa cells co-expressing GalT-moxGFP and GalT-mCherry show colocalization in the GC structure, but GalT-moxGFP does not localizes to red puncta. (d) Pretreatment with NH$_4$Cl for 3 h leads to substantial colocalization of GalT-moxGFP with red puncta. (e) GalT-mcherry expressing HeLa cells were fixed and stained for the lysosomal marker anti-LAMP1. Several red puncta colocalize with the LAMP1 positive structures. Scale bars=10 µm.

First, we tested whether the GalT-mCherry puncta are disrupted GC membranes by staining for GC and GC/intermediate compartment markers GM130 and β-COP, respectively. Both markers robustly colocalize with the compact perinuclear GC structures labeled by the GalT fusions, but neither labels the mCherry puncta throughout the cell (FIG. 11, Panels a and b). These results also reveal that GalT-mCherry does not necessarily disrupt the GC. We further tested this idea by co-expressing GalT-mCherry with GalT-moxGFP. Both reporters localize to GC structures and only GalT-mCherry localizes to puncta, as well (FIG. 11, Panel c). Therefore, the GC remains intact and GalT-mCherry does not appear to drag other GalT reporters into puncta structures.

Next, we revisited our data with the GalT-moxCer3 reporter, which also localized in a punctate distribution (FIG. 9, Panel c). Aside from spectra, a major difference between Cerulean3 (moxCer3) and other GFP family members is the exceptionally low pKa (3.2) (Markwardt et al. 2011) relative to the pKa of GFPs (5.5-6). The pKa is the pH at which a fluorophore will be quenched in brightness by one half. FPs often fully quench at only slightly lower pH values. Like Cer3, mCherry has a low pKa <4.5 (Shaner et al. 2004). In addition, mCherry is resistant to proteolysis in lysosomes, while GFP family members are highly susceptible (Kimura et al. 2007). Katayama et al. reported that cytoplasmic mCherry can accumulate in lysosomes, possibly through an autophagy mechanism (Katayama et al. 2008) and that the resistance of mCherry to pH and degradation leads to an aggregate-like pattern. We considered the possibility that a similar phenomenon occurs for mCherry fused to membrane proteins in the secretory pathway.

We hypothesized that GalT-FP fusions are not statically localized to the GC and could traffic to the endosomal/lysosomal system for turnover. The pH of late GC compartments and the endosomal lysosomal system decreases from 6.5 down to 4 (Paroutis et al. 2004), which should quench the fluorescence of most GFP family members. To test whether GalT-moxGFP traffics similarly could accumulate in puncta, the pH gradient of the secretory pathway was disrupted. Treatment with $NH_4Cl$ for three hours dramatically redistributed GalT-moxGFP, which now colocalized with GalT-mCherry puncta (FIG. 11, Panel d). Finally, we directly tested whether GalT-mCherry puncta localize in lysosomes by colocalizing with the marker anti-LAMP1 (FIG. 11, Panel e). Together, these observations have important implications for imaging studies in the secretory pathway.

The choice of FP clearly influences the localization pattern. Our data suggest that GalT eventually traffics to the lysosome; though we cannot currently rule out the possibility that mCherry contains a cryptic lysosome targeting sequence. GFP family members, including the new ox and mox variants, robustly label the GC with high signal/noise probably because the FPs are destroyed in lysosomes. In addition, mCherry reportedly matures more slowly than GFP family member (Couturier et al. 2014) and this property could decrease the visible pool of GalT-mCherry in the GC at steady state. Huang et al. cautioned that even the FP linker can impact FP fusion stability and steady state distribution (Huang et al. 2014). Whether the properties of a GFP family member or mCherry are advantageous or disadvantageous will depend on the goal of the experiment, though awareness of these issues will enable investigators to exploit these different properties. Therefore, when employing FP fusions in experiments, it is vital to validate the behavior of the fusion protein relative to the native protein.

Figure 12:
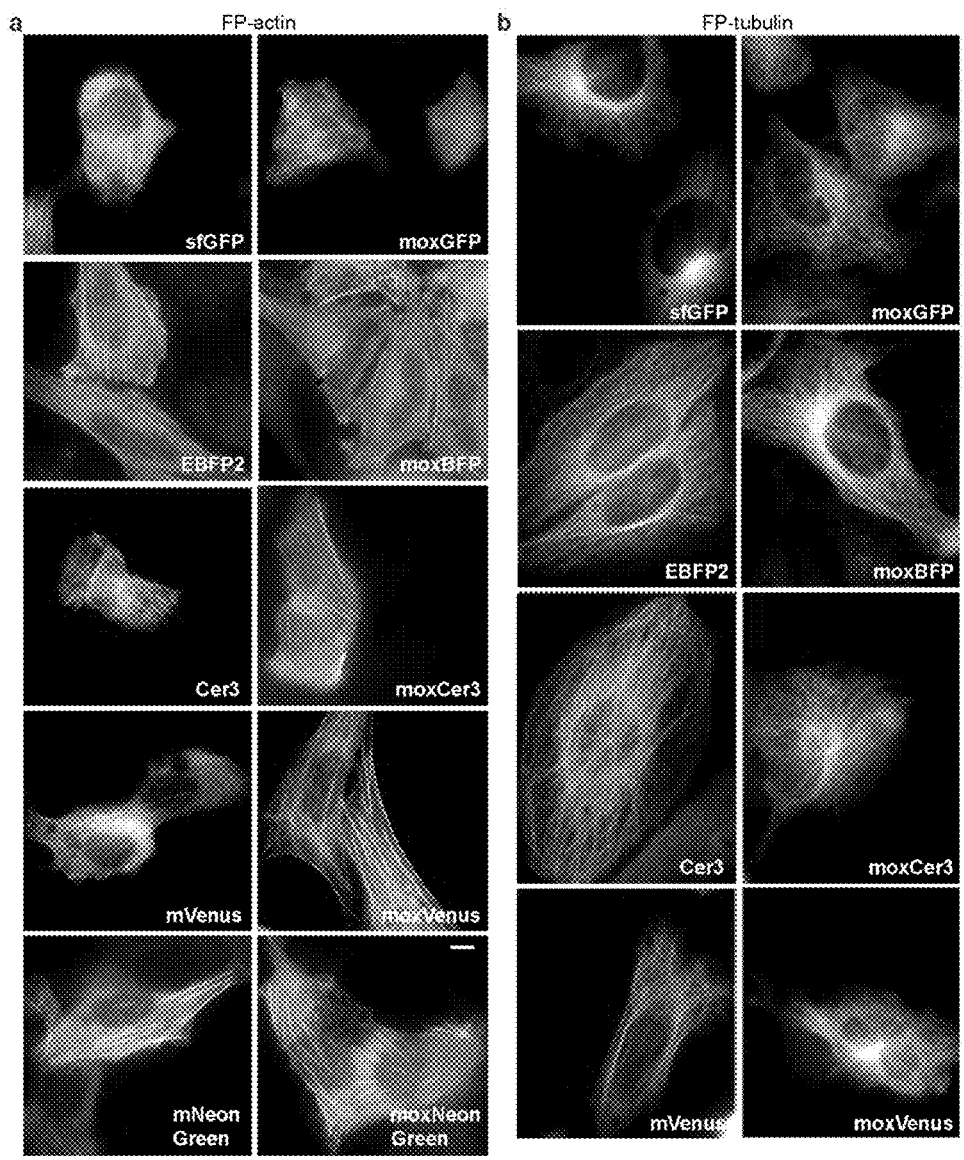
FIG. 12. Cytoplasmic ox-FP fusions. (a) Representative images of transiently transfected HeLa cells expressing parental FP- and paired oxFP-actin or (b) FP-tubulin fusions. Scale bars equal 10 µm.
Figure 13:
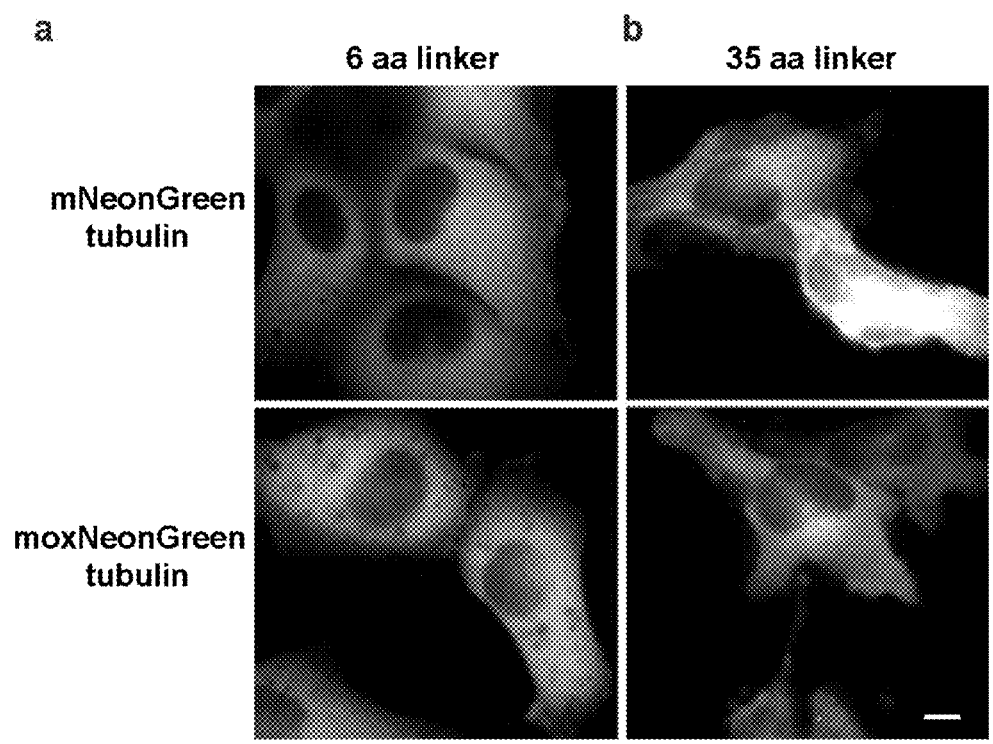
FIG. 13. Representative images of transiently transfected HeLa cells expressing mNeonGreen or moxNeonGreen with (a) 6 amino acid linker or (b) 35 amino acid linker. Scale bars equal 10 µm.

Finally, to confirm the utility of the moxFPs, we sought to confirm the functionality of the FPs in the cytoplasm. We found that all of the GFP family member moxFPs functioned comparably with the parental proteins when fused into standard actin and tubulin constructs and gave expected distributions of actin stress fibers and microtubules (FIG. 12, Panels a and b). We had different results with mNeonGreen and moxNeonGreen. Both versions formed actin stress fibers (FIG. 12, Panel a). However, neither version was significantly incorporated into microtubules (FIG. 12, Panel b). In the original report (Shaner et al. 2013), it was unclear how long the linker was, but we tried both lengths and had the same result (FIG. 13, Panels a and b). We recommend caution when making fusions with mNeonGreen and its variants. The new toolbox of the moxFPs, which includes moxBFP, moxCerulean3, moxVenus, and moxNeonGreen, provides a powerful variety of inert options for multiple FP expression combinations for soluble and membrane FP-fusions.

Discussion

The majority of reported FPs contain at least one cysteine residue (with the notable exception of the DsRed/mFruit family). Despite the resulting undesirable disulfide bonded misfolded oligomers, the higher molecular weight oligomers represent a curious protein folding phenomenon that suggests potentially important insights into the process of FP folding in cells. A completely and correctly folded FP β-barrel structure should shield cysteines away from potential interactions. Therefore, disulfides must form between FPs before they have folded into β-barrels.

The ER lumen is a highly crowded environment (100 mg/ml protein (Schroder et al. 2005)). As nascent FPs enter the crowded ER lumen, they will transiently contact numerous diffusing secretory proteins. We have no evidence that FPs form inappropriate disulfide bonds arbitrarily with random luminal ER proteins. We would have expected to see smears on non-reducing immunoblots, instead of discrete bands at specific molecular weights that correspond to FP interchain disulfide-bonded FP species. Disulfide bonded FP oligomers suggest FPs do not immediately fold into their protected native β-barrel structure. Instead, FPs likely form persistent (at least for seconds and maybe longer) one or more intermediate species ($FP_{int}$) that can oligomerize via an interface distinct from the hydrophobic dimerizing interface on the outer surface of GFP. These species are probably also recognized by resident ER chaperones. Incompletely folded GFP molecules likely interact with the complementary domains of other GFP molecules in trans. It is unclear whether the quasi-species are reversible and can eventually form two separately folded and fluorescent FPs in the cytoplasm or ER. Within the ER, cysteine residues in the $FP_{int}$ are exposed and could preferentially form a disulfide bond with an interacting $FP_{int}$ species. This scenario is especially plausible if the $FP_{int}$ has a high affinity for homo-oligomerization, increasing the likelihood of disulfide bonds forming between FPs, probably in cooperation with a PDI family member.

To circumvent the challenges subcellular organelles pose to FPs, we sought to optimize FP technologies. We have created a set of bright oxFPs (Table 1-3) that can be used for quantitative multicolor labeling strategies. In the cytoplasm and non-cytoplasmic compartments, oxGFP, oxBFP, oxCerulean, moxCerulean3, and oxVenus can be reliably and robustly expressed.

Furthermore, the moxFPs versions are monomeric and encode no apparent sequence specific sites accessible for N-linked glycosylation or disulfide bond formation. The moxFPs are currently the most practical solution to reliably engineer FP fusions with soluble and membrane cellular proteins of interest. Our results emphasize the urgent need to develop better cysteineless and robustly monomeric red FPs for use in the secretory pathway.

We have extensively studied the impact of the chemically distinct and reactive environments of the eukaryotic secretory compartments on the functionality of FPs. As we explored popular FP applications, it became apparent that moxFP modifications are essential. For example, we measured a significant decrease in maximum fluorescence of non-optimized ER-EBFP2 (FIG. 6, Panel c). Findings with GalT-mGFP further confirm significant loss and mislocalization of functional fluorescent molecules due to the formation of non-native disulfide bonds (FIG. 7). We predict the accumulation of misfolded non-fluorescent FPs molecules within the ER could lead to underappreciated off target effects, including changes to the ER environment through titration of ER chaperones and crowding effects of aggregated misfolded proteins leading to unintended side effects on secretory resident proteins and protein trafficking.

Equally importantly, the non-FP component of a dark pool of fusion proteins may remain functional and could lead to gross underestimations of the location and activity levels of fusion proteins. In such cases, the concentration of oxFP fusions expressed in cells will be most accurately defined by biochemical analysis instead of imaging analysis. For example, the observed FP-fusion fluorescence would correlate with the levels of the correctly folded monomeric species detected by immunoblot. As the optimized oxFPs do not accumulate misfolded, non-fluorescent species, total levels of fluorescence will quantitatively reflect FP-fusion levels.

This last point is especially pertinent to the current thrust towards quantitative single cell imaging for modern cell biologists. CMV promoter driven transiently transfected plasmids have been useful for studying proteins in cells, but it remains unclear how much the behavior of grossly overexpressed proteins accurately reflects physiologic cell and protein behaviors. New engineering technologies, especially CRISPR, have made it possible to chromosomally tag endogenous genes with FPs to enable truly physiologic expression and regulation of levels of FP-fusion proteins (Yang et al. 2013). In the absence of CMV promoter driven expression levels, it will be vital for each FP fusion to correctly fold and fluoresce to quantitatively visualize FP-fusions using fluorescence microscopy. Quantitative experiments to investigate cell-to-cell variation, proteomics, and to help develop quantitative cellular models will require accurate censuses of cellular protein populations. FP fusions absolutely must not distort or perturb cellular compartments. The bright multicolor moxFPs developed here were motivated by these needs and represent essential tools for cell biologists studying diverse intracellular environments.

EXAMPLE 2

Tools for Exceptional Overexpression and Structural Stabilization of Proteins Summary This example presents protein fusion tags for increasing the expression of properly folded proteins using mammalian cell culture. The fusion tags are particularly useful for proteins passing through the endoplasmic reticulum (ER), such as secretory proteins and recombinant membrane proteins, especially G Protein Coupled Receptors (GPCRs). Bacterial, insect, or yeast systems currently are preferred over mammalian culture for integral membrane protein production due to their high protein yield and low cost. However, many mammalian membrane proteins are difficult to express in bacterial systems or require mammalian-specific post-translational modifications for function. Expression of functional membrane proteins thus remains a major bottleneck for structural studies and for subsequent development of therapeutics. Mammalian cell culture has been harnessed for expression of challenging cytoplasmic and secreted targets, but protein yields typically lag far behind those of bacterial, yeast, and insect systems.

The fusion tags described in this example exhibit an ability to enhance transient expression of soluble functional proteins in mammalian cell culture, improve the expression of correctly folded and trafficked integral membrane protein yields by 2-10-fold over existing mammalian cell culture systems, and simplify the process of constructing and screening structurally stabilized membrane proteins for crystallization trials.

Background

Basic research of protein structure and function, screening and development of small molecule drugs that target specific proteins, and development of protein therapeutics all depend on having large quantities of protein retaining native structure and function. Membrane proteins are among the most important therapeutic targets and also the most challenging to produce in heterologous systems. Bacterial expression can yield large amounts of recombinant proteins at low cost, but many proteins require expression in a mammalian host to ensure proper folding and post-translational modification. Yeast and baculovirus/insect cell systems have significant differences in glycosylation modifications and lack mammalian processing, co-factors, and chaperones. Insect cells also frequently express these GPCRs as a mixture of folded and misfolded proteins, in contrast to the correct folding obtained in mammalian cell lines (Thomas 2014).

However, current mammalian cell culture systems have significant shortcomings (McCusker et al. 2007, Almo et al. 2014, Young et al. 2012). Although transient transfection is simple to perform, protein yields are limited by the short term of expression and by the difficulty in scaling-up the transfection. For long-term and large-scale expression, stable cell lines are created by genomic integration of the gene of interest. However, this time-consuming and laborious process is not well suited for pre-screening of many variants of each membrane protein, which is often required to identify candidates for crystallization trials. Thus, there is a demand for technologies that can dramatically improve membrane protein yield in transient mammalian cell culture expression.

Figure 14:
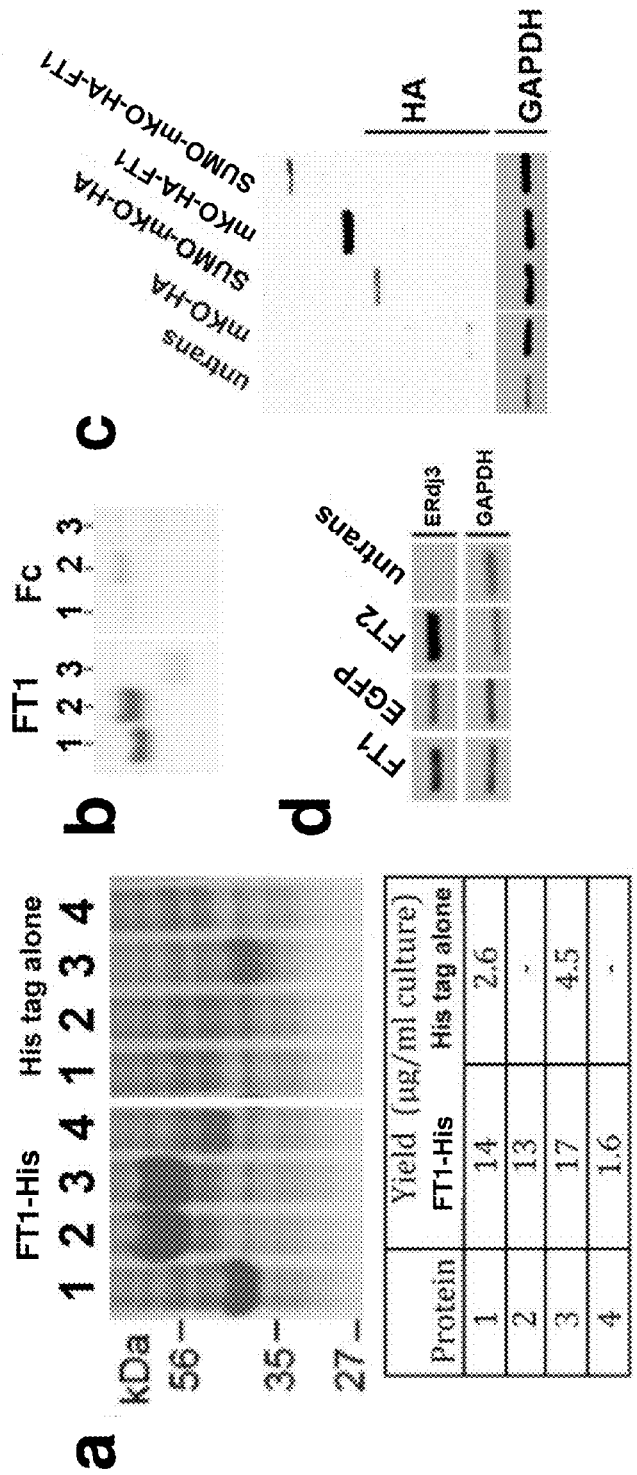
FIG. 14. (a) Increased expression of fusions of (1) Semaphorin 3C (*Homo sapiens*), (2) VISTA (*Bos taurus*), (3) VISTA (*Rattus norvegicus*), and (4) Polymeric Ig receptor (*Mus musculus*) to His-tagged Fusion Tag 1 (FT1) relative to fusion of His tag alone. Coomassie stained gel. (b, c, d) Expression enhancement due to FT1 compared to Fc or SUMO or Fusion Tag 2 (FT2). (b) Significant expression of (1) VISTA, platelet receptor Gi24 (*Rattus norvegicus*), (2) VISTA, platelet receptor Gi24 (*Bos taurus*), and (3) Polymeric Ig receptor (*Mus musculus*) with fusion to FT1, but not with fusion to Fc. Coomassie stained gel. (c) Expression of mKO (Kusabira Orange) fused to SUMO and FT1. Fusion to FT1 increases expression, but SUMO negates FT1 enhancement. Immunoblotted with anti-HA and anti-GAPDH loading control. (d) Expression of fusions of ERdj3 to FT1, EGFP, and FT2 in transfected cell lysates.

The present example discusses expression-enhancing fusion tags that can be used in mammalian cells. One of these fusion tags, referred to herein as "Fusion Tag 2" (FT2) (SEQ ID NO:2), can enhance secretory protein yield in mammalian cell culture by 5-20 fold (FIG. 14).

Fusion Tag 2 (FT2)

FT2 represents one of a new class of expression-enhancing fusion proteins. The parent protein, Fusion Tag 1 (FT1) (SEQ ID NO:2 with S49C, T67Y, S71C, and K207V), was derived from a fluorescent protein, EGFP. FT1 unexpectedly expressed at significantly higher levels than EGFP (data not shown). Importantly, fusion of protein partners to FT1 likewise resulted in dramatically higher expression in multiple human tissue culture cells. The expression of four secretory proteins that contain N-glycosylation sites and/or form disulfide bonds increased to 2-17 μg/ml of cell culture for FT1 fusions, compared to barely detectable levels without the tag (FIG. 14, Panel a). FT1 was superior to both Fc and to SUMO for enhancing protein expression (FIG. 14, Panels b and c).

Modifications of FT1 were carried out to remove all cysteines, make the protein highly monomeric ($K_d$>20 mM), and further enhance expression of fusion protein. The resulting fusion tag, FT2 (SEQ ID NO:2, encoded by SEQ ID NO:1), included the following mutations with respect to FT1: C49S, Y67T, C71S, and V207K. The Y67T mutation renders FT2 non-fluorescent. FT2 increased fusion protein expression over FT1 by at least 2-fold further, using the target protein ERdj3, an ER chaperone (FIG. 14, Panel d). We expect FT2 will likewise increase expression of secretory proteins and membrane proteins. Placement of a stop codon between the protein of interest and FT2 coding sequence prevented increased expression (not shown). Thus, FT2 must be translated for function.

FT2 as a Fusion Tag for Expression of Membrane Proteins

The following experiments will demonstrate functionality of FT2 for fusions with integral membrane proteins in mammalian cells and will demonstrate 2-10× increased expression mediated by FT2 for select membrane proteins.

The data provided above show the ability of the FT1 and particularly FT2 to dramatically enhance expression of soluble proteins in mammalian cells (see FIG. 14). The present experiments will focus on two different classes of integral membrane proteins: single membrane spanners and polyspanners, the latter of which have 2-12 transmembrane domains.

To demonstrate the utility of FT2 and variants thereof, we will fuse FT2 to the N- or C-terminus of a Panel of medically important integral membrane proteins (Table 2-1, FIG. 15, panel a) using Expresso® cloning plasmids (Lucigen Corporation, Madison, Wis.) for FT2-His, His-tag alone, His-Sumo, and Fc-His. Target proteins were selected for their significant folding requirements, which include disulfide bonds, N-glycosylation, trafficking and/or oligomerization. Robust functional assays are available for each target protein.

TABLE 2-1

Integral membrane reporters and test proteins.

| Protein | Size (Amino Acids) | Di-sulfides | N-linked Glyco-sylation | Number of Transmembrane Domains |
|---|---|---|---|---|
| 1. CytERM | 29 | 0 | 0 | 1 |
| 2. b5ext | 562 | 0 | 0 | 1 |
| 3. gp160 HIV1 Env | 856 | 10 | 30 | 1 (trimer) |

TABLE 2-1-continued

Integral membrane reporters and test proteins.

| Protein | Size (Amino Acids) | Di-sulfides | N-linked Glyco-sylation | Number of Transmembrane Domains |
|---|---|---|---|---|
| 4. CFTR | 1480 | 0 | 2 | 12 (oligomer) |
| 5. Beta 2 Adrenergic Receptor (β2AR) | 413 | 2 | 2 | 7 |

CytERM, gp160 HIV1 Env, CFTR, and B2AR (Table 2-1) will also be expressed with Fc and a His-tag at the C-terminus, and b5ext (Table 2-1) will be fused with a His-tag and SUMO at the N-terminus (in separate constructs). We will assess yields of purified FT2 fusion protein relative to controls. We will quantitate levels secreted into media and levels remaining in cells to determine whether fusions fold sufficiently well to pass endoplasmic reticulum quality control surveillance. The yield upon cleavage of fusions from FT2 with TEV protease, followed by centrifugation to pellet insoluble material, will indicate the solubility of overexpressed proteins. Purification and quantitation will be performed as described with respect to FIG. 14, Panel a.

We will employ JCIMPT protocols (http://jcimpt.usc.edu/) for polyspanner membrane proteins to assess levels on the cell surface (using quantitative FACS of live cells). In addition, we can surface-biotinylate cells expressing FT2-fusions, purify samples with His-tag/TALON resin, and measure the ratio of biotinylated protein vs. whole cell lysate by immunoblotting. We will perform immunofluorescence confocal microscopy of cells expressing FT2-fusions and co-stain for endoplasmic reticulum, Golgi complex, and endocytic markers, which will confirm correct targeting and protein expression, folding, and trafficking. Additional assays are available for HIV-1 Env and β2AR.

We will use several additional assays to show that the overexpressed target proteins retain function. For HIV-1 Env, we will demonstrate the ability of cells expressing the reporter to fuse and form syncytia with TZM-bl HeLa cells expressing the target receptors CD4 and CCR5 (Julien et al. 2013). Cells expressing Env-fusions will be mixed with TZM-bl cells and assayed for fusion events as described (Young et al. 2012). For β2AR, we will use immunofluorescence to detect responsiveness to ligand (which causes β2AR to be endocytosed into intracellular compartments from the cell surface). We will also visualize binding of fluorescent ligand to the cell surface and phosphorylation (after isoproterenol stimulation) assessed by anti-phosphoserine immunoblots (Barak et al. 1997, Moyer et al. 1998).

Figure 15:
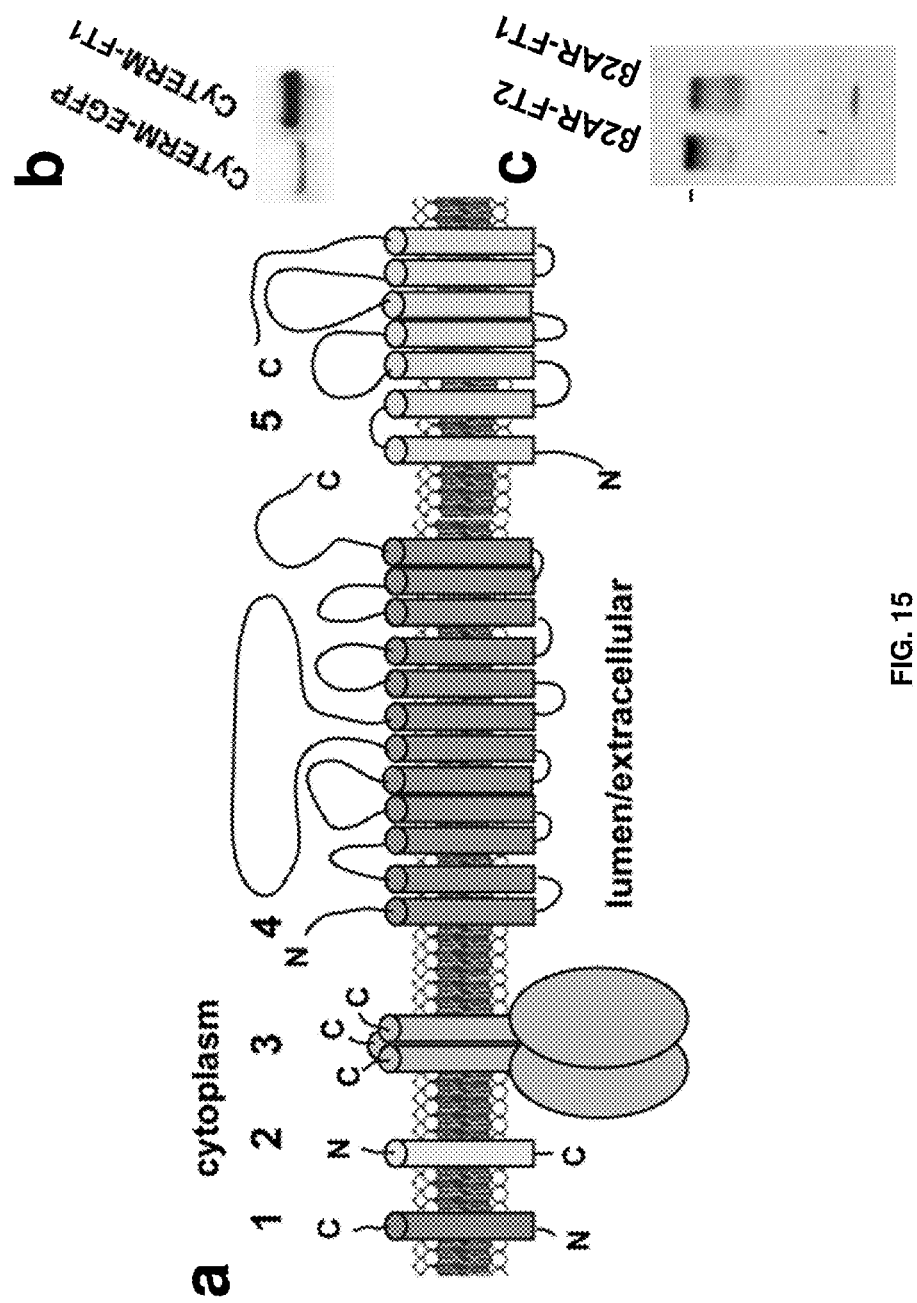
FIG. 15. (a) The topologies of the five test membrane proteins listed in Table 2-1: (1) CytERM, (2) b5ext, (3) gp160 HIV1 Env, (4) cystic fibrosis transmembrane conductance regulator (CFTR), and (5) beta 2 adrenergic receptor (β2AR). N- and C-termini are indicated. (b) Immunoblot of whole cell lysates of cells expressing CytERM fused to EGFP or FT1, which dramatically increases CytERM expression. (c) Immunoblot of whole cell lysates of cells expressing the beta 2 adrenergic receptor (β2AR) fused to FT2 or FT1.

An initial experiment with CytERM fused to either EGFP or FT1 was conducted. As shown in FIG. 15, Panel b, a blot of whole-cell lysates of cells transfected with equal amounts of plasmid for an equal period of time shows drastically enhanced expression of CytERM fused to FT1 with respect to CytERM fused to EGFP.

Another experiment with β2AR fused to either FT1 or FT2 was conducted. As shown in FIG. 15, Panel c, a blot of whole-cell lysates of cells (U-2 OS cells) transfected with equal amounts of plasmid for an equal period of time (24 hours) and stained with antibody that recognizes both FT1 and FT2 shows drastically enhanced expression of β2AR fused to FT2 with respect to β2AR fused to FT1. ImageJ quantitation suggests a nearly 50% difference in levels. A lower molecular weight smear and a more intense lower band with the β2AR-FT1 fusion are consistent with cleavage of the β2AR-FT1 fusion.

FT2 Fusion Parameters

We will demonstrate the effects of fusion position (N- or C-terminal), linker length, and how close FT2 can be to the membrane without affecting localization or folding. For these assays, we have compared and will compare levels of cytoplasmic FT2 fusions for two distinct reporters (see FIG. 15): (1) An ER-retained type I single transmembrane protein CytERM (Costantini et al. 2012), which illustrates that FT1 can enhance levels of a simple transmembrane protein; and (2) A cytoplasmic N-terminal fusion to b5ext (Pedrazzini et al. 1996, Bulbarelli et al. 2002), a modified tail-anchored transmembrane domain that constitutively traffics to the plasma membrane. These short reporter proteins will show FT2 functionality for proteins that are co- and post-translationally inserted into the ER membrane, respectively. Levels of protein in whole cell lysates will be compared on Coomassie SDS-PAGE and immunoblots.

Protease Cleavage Sites

FT2 will be configured to be cleaved from the fusion protein and purified from the target protein. We will include TEV protease cleavage sites between FT2 and the target protein. We will also include a His-tag upstream of N-terminal FT2 fusions (after the signal peptide) and downstream of C-terminal FT2 fusions. We will assess both total protein and amount of protein recovered by affinity purification using Coomassie stained gels of whole cell lysates and affinity-purified material released from the column by cleavage of the affinity tag.

Mechanism of Enhanced Expression

Fusion tags can improve yields of target proteins in a number of ways. Some tags such as MBP and the His-tag aid purification, and others such as the Fc chain (Bell et al. 2013) and superfolder GFP (Pedelacq et al. 2006) improve protein solubility. In contrast, SUMO and FT2 physically increase total protein expression (FIG. 14). Understanding the mechanism(s) of enhanced expression will aid in further optimization of FT2. We hypothesize that FT2 (a) enhances mRNA levels, (b) enhances translation rates, and/or (c) protects fusions from degradation, a mechanism hypothesized for SUMO fusions (Marblestone et al. 2006). We will assay each of these aspects for a reporter protein fused or not fused to FT2. Depending on the outcome, we will identify and/or improve the mRNA stabilizing or translation enhancing element or define an optimal configuration to maximize folding enhancement.

We first will perform RT-PCR to quantitate and compare mRNA levels in transiently transfected tissue culture to determine if FT2 increases message levels. We subsequently will examine translation rates by measuring the time course of protein expression following induction in a tet-inducible system to measure rates of protein production for an FT2 fusion relative to an untagged reporter. Even though FT2 typically generates more total protein, the relative rate of translation is not known. Because our assays show an increase in total protein in whole cell lysates, our data argue that FT2 is not simply preventing aggregation. Instead, FT2 may improve folding and prevent degradation. We will test this possibility by measuring reporter and fused reporter accumulation rates in the presence of the proteasome inhibitor MG132 or lysosomal protease inhibitors. We will measure protein production plus and minus degradation inhibitors to distinguish between folding and translation. A key prediction of enhanced folding is that FT2 must be attached to the reporter to have an effect. To test this hypothesis, we will fuse the reporter to FT2 with a functional or a mutated P2A site (Donnelly et al. 2001), to produce either two separate proteins or a single fused protein, respectively.

Enhancement of folding should be evident only with the inactive P2A. The results of these experiments should help us further optimize FT2.

SELECT CITED REFERENCES

Ai, H., Shaner, N. C., Cheng, Z., Tsien, R. Y. & Campbell, R. E. Exploration of new chromophore structures leads to the identification of improved blue fluorescent proteins. *Biochemistry* 46, 5904-10 (2007).

Almo S C, Love J D. (2014) Better and faster: improvements and optimization for mammalian recombinant protein production. *Current opinion in structural biology* 26: 39-43.

Aronson, D. E., Costantini, L. M. & Snapp, E. L. Superfolder GFP is fluorescent in oxidizing environments when targeted via the Sec translocon. *Traffic Copenhagen Denmark* 12, 543-548 (2011).

Auldridge M E, Cao H, Sen S, Franz L P, Bingham C A, Yennamalli R M, Phillips G N, Mead D, Steinmetz E J. (2015) LucY: a versatile new fluorescent reporter protein. *PLOS One* 10(4):e0124272.

Barak L S, Ferguson S S, Zhang J, Martenson C, Meyer T, Caron M G. (1997) Internal trafficking and surface mobility of a functionally intact beta2-adrenergic receptor-green fluorescent protein conjugate. *Molecular pharmacology* 51: 177-84.

Bell M R, Engleka M J, Malik A, Strickler J E. (2013) To fuse or not to fuse: what is your purpose? *Protein science: a publication of the Protein Society* 22: 1466-77.

Benali-Furet N L, Chami M, Houel L, De Giorgi F, Vernejoul F, Lagorce D, Buscail L, Bartenschlager R, Ichas F, Rizzuto R, Paterlini-Brechot P. (2005) Hepatitis C virus core triggers apoptosis in liver cells by inducing ER stress and ER calcium depletion. *Oncogene* 24: 4921-33.

Bevis, B. J. & Glick, B. S. Rapidly maturing variants of the Discosoma red fluorescent protein (DsRed). *Nat. Biotechnol.* 20, 83-7 (2002).

Brandizzi F, Fricker M, Hawes C. A greener world: the revolution in plant bioimaging. *Nat Rev Mol Cell Biol.* 2002 July; 3(7):520-30.

Breitling, J. & Aebi, M. N-linked protein glycosylation in the endoplasmic reticulum. *Cold Spring Harb. Perspect. Biol.* 5, a013359 (2013).

Bulbarelli A, Sprocati T, Barberi M, Pedrazzini E, Borgese N. (2002) Trafficking of tail-anchored proteins: transport from the endoplasmic reticulum to the plasma membrane and sorting between surface domains in polarised epithelial cells. *Journal of cell science* 115: 1689-702.

Butt T R, Edavettal S C, Hall J P, Mattern M R. (2005) SUMO fusion technology for difficult-to-express proteins. *Protein expression and purification* 43: 1-9.

Caffrey M. (2009) Crystallizing membrane proteins for structure determination: use of lipidic mesophases. *Annual review of biophysics* 38: 29-51.

Chen, J. W., Murphy, T. L., Willingham, M. C., Pastan, I. & August, J. T. Identification of two lysosomal membrane glycoproteins. *J. Cell Biol.* 101, 85-95 (1985).

Chen, J. C., Viollier, P. H. & Shapiro, L. A membrane metalloprotease participates in the sequential degradation of a *Caulobacter* polarity determinant. *Mol. Microbiol.* 55, 1085-103 (2005).

Cherezov V, Rosenbaum D M, Hanson M A, Rasmussen S G, Thian F S, Kobilka T S, Choi H J, Kuhn P, Weis W I, Kobilka B K, Stevens R C. (2007) High-resolution crystal structure of an engineered human beta2-adrenergic G protein-coupled receptor. *Science* 318: 1258-65. 2583103

Chou, P. Y. & Fasman, G. D. Prediction of protein conformation. *Biochemistry* 13, 222-45 (1974).

Chun E, Thompson A A, Liu W, Roth C B, Griffith M T, Katritch V, Kunken J, Xu F, Cherezov V, Hanson M A, Stevens R C. (2012) Fusion partner toolchest for the stabilization and crystallization of G protein-coupled receptors. *Structure* 20: 967-76. 3375611

Coffman, V. C. & Wu, J.-Q. Every laboratory with a fluorescence microscope should consider counting molecules. *Mol. Biol. Cell* 25, 1545-8 (2014).

Cole, N. B. et al. Diffusional mobility of Golgi proteins in membranes of living cells. *Science* 273, 797-801 (1996).

Costantini L M, Baloban M, Markwardt M L, Rizzo M, Guo F, Verkhusha V V, Snapp E L. A palette of fluorescent proteins optimized for diverse cellular environments. *Nat Commun.* 2015 Jul. 9; 6:7670.

Costantini L M, Fossati M, Francolini M, Snapp E L. (2012) Assessing the tendency of fluorescent proteins to oligomerize under physiologic conditions. *Traffic* 13: 643-9.

Costantini L M, Irvin S C, Kennedy S C, Guo F, Goldstein H, Herold B C, Snapp E L. Engineering and exploitation of a fluorescent HIV-1 gp120 for live cell CD4 binding assays. *Virology.* 2015 February; 476:240-8.

Costantini, L. M. & Snapp, E. L. Fluorescent proteins in cellular organelles: serious pitfalls and some solutions. *DNA Cell Biol.* 32, 622-7 (2013).

Costantini, L. M., Subach, 0. M., Jaureguiberry-bravo, M., Verkhusha, V. V & Snapp, E. L. Cysteineless non-glycosylated monomeric blue fluorescent protein, secBFP2, for studies in the eukaryotic secretory pathway. *Biochem. Biophys. Res. Commun.* 430, 1114-9 (2013).

Couturier, L., Trylinski, M., Mazouni, K., Darnet, L. & Schweisguth, F. A fluorescent tagging approach in *Drosophila* reveals late endosomal trafficking of Notch and Sanpodo. *J. Cell Biol.* 207, 351-63 (2014).

Crameri, A., Whitehorn, E. A., Tate, E. & Stemmer, W. P. C. Improved green fluorescent protein by molecular evolution using DNA shuffling. *Nat. Biotechnol.* 14, 315-319 (1996).

Donnelly M L, Luke G, Mehrotra A, Li X, Hughes L E, Gani D, Ryan M D. (2001) Analysis of the aphthovirus 2A/2B polyprotein 'cleavage' mechanism indicates not a proteolytic reaction, but a novel translational effect: a putative ribosomal 'skip'. *J Gen Virol* 82: 1013-25.

Grotzke, J. E., Lu, Q. & Cresswell, P. Deglycosylation-dependent fluorescent proteins provide unique tools for the study of ER-associated degradation. *Proc. Natl. Acad. Sci. U.S.A* 110, 3393-8 (2013).

Haseloff, J. (1999) GFP variants for multispectral imaging of living cells. *Methods Cell Biol.* 58, 139-151.

Hattori M, Hibbs R E, Gouaux E. (2012) A fluorescence-detection size-exclusion chromatography-based thermostability assay for membrane protein precrystallization screening. *Structure* 20: 1293-9. 3441139

Hegde R S, Bernstein H D. The surprising complexity of signal sequences. *Trends Biochem Sci.* 2006 October; 31(10):563-71.

Heim, R. et al. (1994) Wavelength mutations and posttranslational autoxidation of green fluorescent protein. *Proc. Natl Acad. Sci. USA* 91, 12501-12504.

Heim, R., Cubitt, A. B. & Tsien, R. Y. Improved green fluorescence. *Nature* 373, 663-4 (1995).

Huang, L., Pike, D., Sleat, D. E., Nanda, V. & Lobel, P. Potential pitfalls and solutions for use of fluorescent fusion proteins to study the lysosome. *PLoS One* 9, e88893 (2014).

Ishihara G, Goto M, Saeki M, Ito K, Hori T, Kigawa T, Shirouzu M, Yokoyama S. (2005) Expression of G protein coupled receptors in a cell-free translational system using detergents and thioredoxin-fusion vectors. *Protein expression and purification* 41: 27-37.

Jain, R. K., Joyce, P. B., Molinete, M., Halban, P. A. & Gorr, S. U. Oligomerization of green fluorescent protein in the secretory pathway of endocrine cells. *Biochem. J.* 360, 645-9 (2001).

Julien J P, Sok D, Khayat R, Lee J H, Doores K J, Walker L M, Ramos A, Diwanji D C, Pejchal R, Cupo A, Katpally U, Depetris R S, Stanfield R L, McBride R, Marozsan A J, Paulson J C, Sanders R W, Moore J P, Burton D R, Poignard P, Ward A B, Wilson I A. (2013) Broadly neutralizing antibody PGT121 allosterically modulates CD4 binding via recognition of the HIV-1 gp120 V3 base and multiple surrounding glycans. *PLoS pathogens* 9: e1003342.

Katayama, H., Yamamoto, A., Mizushima, N., Yoshimori, T. & Miyawaki, A. GFP-like proteins stably accumulate in lysosomes. *Cell Struct. Funct.* 33, 1-12 (2008).

Kawate T, Gouaux E. (2006) Fluorescence-detection size-exclusion chromatography for precrystallization screening of integral membrane proteins. *Structure* 14: 673-81.

Kimura, S., Noda, T. & Yoshimori, T. Dissection of the autophagosome maturation process by a novel reporter protein, tandem fluorescent-tagged LC3. *Autophagy* 3, 452-60 (2007).

Kredel, S. et al. mRuby, a bright monomeric red fluorescent protein for labeling of subcellular structures. *PLoS One* 4, e4391 (2009).

Kremers G J, Goedhart J, van den Heuvel D J, Gerritsen H C, Gadella T W Jr. Improved green and blue fluorescent proteins for expression in bacteria and mammalian cells. *Biochemistry*. 2007 Mar. 27; 46(12):3775-83.

Lam, A. J. et al. Improving FRET dynamic range with bright green and red fluorescent proteins. *Nat. Methods* 9, 1005-12 (2012).

Landgraf, D., Okumus, B., Chien, P., Baker, T. A. & Paulsson, J. Segregation of molecules at cell division reveals native protein localization. *Nat. Methods* 9, 480-2 (2012).

Larkin M A, Blackshields G, Brown N P, Chenna R, McGettigan P A, McWilliam H, Valentin F, Wallace I M, Wilm A, Lopez R, Thompson J D, Gibson T J, Higgins D G. (2007). Clustal W and Clustal X version 2.0. Bioinformatics, 23, 2947-2948.

Lippincott-Schwartz, J., Cole, N. B., Marotta, A., Conrad, P. A. & Bloom, G. S. Kinesin is the motor for microtubule-mediated Golgi-to-ER membrane traffic. *J. Cell Biol.* 128, 293-306 (1995).

Marblestone J G, Edavettal S C, Lim Y, Lim P, Zuo X, Butt T R. (2006) Comparison of SUMO fusion technology with traditional gene fusion systems: enhanced expression and solubility with SUMO. *Protein science: a publication of the Protein Society* 15: 182-9. 2242369.

Markwardt, M. L. et al. *An Improved Cerulean Fluorescent Protein with Enhanced* Brightness and Reduced Reversible Photoswitching. *PLoS One* 6, e17896 (2011).

Matz, M. V et al. Fluorescent proteins from nonbioluminescent Anthozoa species. *Nat. Biotechnol.* 17, 969-73 (1999).

McCusker E C, Bane S E, O'Malley M A, Robinson A S. (2007) Heterologous GPCR expression: a bottleneck to obtaining crystal structures. *Biotechnology progress* 23: 540-7.

Merzlyak, E. M. et al. Bright monomeric red fluorescent protein with an extended fluorescence lifetime. *Nat. Methods* 4, 555-557 (2007).

Miyawaki, A. et al. (1997) Fluorescent indicators for $Ca^{2+}$ based on green fluorescent proteins and calmodulin. *Nature* 388, 882-887.

Miyawaki, A., Shcherbakova, D. M. & Verkhusha, V. V. Red fluorescent proteins: chromophore formation and cellular applications. *Curr. Opin. Struct. Biol.* 22, 679-88 (2012).

Morozova, K. S. et al. Far-red fluorescent protein excitable with red lasers for flow cytometry and superresolution STED nanoscopy. *Biophys. J.* 99, L13-5 (2010).

Moyer B D, Loffing J, Schwiebert E M, Loffing-Cueni D, Halpin P A, Karlson K H, Ismailov, I I, Guggino W B, Langford G M, Stanton B A. (1998) Membrane trafficking of the cystic fibrosis gene product, cystic fibrosis transmembrane conductance regulator, tagged with green fluorescent protein in madin-darby canine kidney cells. *The Journal of biological chemistry* 273: 21759-68.

Nagai, T. et al. A variant of yellow fluorescent protein with fast and efficient maturation for cell-biological applications. *Nat. Biotechnol.* 20, 87-90 (2002).

Ormö, M. et al. Crystal structure of the Aequorea victoria green fluorescent protein. *Science* (80-.). 273, 1392-5 (1996).

Paroutis, P., Touret, N. & Grinstein, S. The pH of the secretory pathway: measurement, determinants, and regulation. *Physiology (Bethesda)*. 19, 207-15 (2004).

Patterson, G. H., Knobel, S. M., Sharif, W. D., Kain, S. R. & Piston, D. W. Use of the green fluorescent protein and its mutants in quantitative fluorescence microscopy. *Biophys. J.* 73, 2782-90 (1997).

Pedelacq J D, Cabantous S, Tran T, Terwilliger T C, Waldo G S. (2006) Engineering and characterization of a superfolder green fluorescent protein. *Nature Biotechnology* 24: 79-88.

Pedrazzini E, Villa A, Borgese N. (1996) A mutant cytochrome b5 with a lengthened membrane anchor escapes from the endoplasmic reticulum and reaches the plasma membrane. *Proceedings of the National Academy of Sciences of the United States of America* 93: 4207-12.

Prasher, D. C., Eckenrode, V. K., Ward, W. W., Prendergast, F. G. & Cormier, M. J. Primary structure of the Aequorea victoria green-fluorescent protein. *Gene* 111, 229-233 (1992).

Reed, M. L. et al. (2001) High-level expression of a synthetic red-shifted GFP coding region incorporated into transgenic chloroplasts. *Plant J.* 27, 257-265.

Rizzo, M. A., Davidson, M. W. & Piston, D. W. Fluorescent protein tracking and detection: fluorescent protein structure and color variants. *Cold Spring Harb. Protoc.* 2009, pdb.top63 (2009).

Rizzo, M. A., Springer, G. H., Granada, B. & Piston, D. W. An improved cyan fluorescent protein variant useful for FRET. *Nat. Biotechnol.* 22, 445-9 (2004).

Rosenbaum D M, Cherezov V, Hanson M A, Rasmussen S G, Thian F S, Kobilka T S, Choi H J, Yao X J, Weis W I, Stevens R C, Kobilka B K. (2007) GPCR engineering yields high-resolution structural insights into beta2-adrenergic receptor function. *Science* 318: 1266-73.

Schröder, M. & Kaufman, R. J. ER stress and the unfolded protein response. *Mutat. Res.* 569, 29-63 (2005).

Serrano-Vega M J, Magnani F, Shibata Y, Tate C G. (2008) Conformational thermostabilization of the beta1-adrenergic receptor in a detergent-resistant form. *Proceedings of the National Academy of Sciences of the United States of America* 105: 877-82. 2242685

Shaner N C, Patterson G H, Davidson M W. Advances in fluorescent protein technology. *J Cell Sci.* 2007 Dec. 15; 120(Pt 24):4247-60.

Shaner, N. C. et al. Improved monomeric red, orange and yellow fluorescent proteins derived from *Discosoma* sp. red fluorescent protein. *Nature Biotechnology* 22, 1567-1572 (2004).

Shaner, N. C. et al. A bright monomeric green fluorescent protein derived from *Branchiostoma lanceolatum*. *Nat. Methods* 10, 407-9 (2013).

Shcherbakova, D. M., Subach, O. M. & Verkhusha, V. V. Red fluorescent proteins: advanced imaging applications and future design. *Angew. Chem. Int. Ed. Engl.* 51, 10724-38 (2012).

Shemiakina, I. I. et al. A monomeric red fluorescent protein with low cytotoxicity. *Nat. Commun.* 3, 1204 (2012).

Siegel, A. P., Baird, M. A., Davidson, M. W. & Day, R. N. Strengths and weaknesses of recently engineered red fluorescent proteins evaluated in live cells using fluorescence correlation spectroscopy. *Int. J. Mol. Sci.* 14, 20340-58 (2013).

Siemering, K. R. et al. (1996) Mutations that suppress the thermosensitivity of green fluorescent protein. *Curr. Biol.* 6, 1653-1663.

Snaith, H. A., Anders, A., Samejima, I. & Sawin, K. E. New and old reagents for fluorescent protein tagging of microtubules in fission yeast; experimental and critical evaluation. *Methods Cell Biol.* 97, 147-72 (2010).

Snapp E L, Hegde R S, Francolini M, Lombardo F, Colombo S, Pedrazzini E, Borgese N, Lippincott-Schwartz J. (2003) Formation of stacked ER cisternae by low affinity protein interactions. *The Journal of cell biology* 163: 257-69.

Snapp, E. L., Sharma, A., Lippincott-Schwartz, J. & Hegde, R. S. Monitoring chaperone engagement of substrates in the endoplasmic reticulum of live cells. *Proc. Natl. Acad. Sci.* 103, 6536-41 (2006).

Snapp, E. L. Design and use of fluorescent fusion proteins in cell biology. *Curr. Protoc. Cell Biol.* Chapter 21, Unit 21.4 (2005).

Su H L, Liao C L, Lin Y L. (2002) Japanese encephalitis virus infection initiates endoplasmic reticulum stress and an unfolded protein response. *Journal of virology* 76: 4162-71.

Subach, O. M. et al. Conversion of red fluorescent protein into a bright blue probe. *Chem. Biol.* 15, 1116-24 (2008).

Suzuki, T. et al. Development of Cysteine-Free Fluorescent Proteins for the Oxidative Environment. *PLoS One* 7, e37551 (2012).

Thomas J, Tate C G. (2014) Quality control in eukaryotic membrane protein overproduction. *Journal of molecular biology* 426: 4139-54.

Tsien R Y. (1998) The green fluorescent protein. *Annu Rev Biochem.* 67:509-44.

Wang, S., Moffitt, J. R., Dempsey, G. T., Xie, X. S. & Zhuang, X. Characterization and development of photoactivatable fluorescent proteins for single-molecule-based superresolution imaging. *Proc. Natl. Acad. Sci. U.S.A* 111, 8452-7 (2014).

Warne T, Serrano-Vega M J, Baker J G, Moukhametzianov R, Edwards P C, Henderson R, Leslie A G, Tate C G, Schertler G F. (2008) Structure of a beta1-adrenergic G-protein-coupled receptor. *Nature* 454: 486-91. 2923055.

Xu F, Liu W, Hanson M A, Stevens R C, Cherezov V. (2011) Development of an Automated High Throughput LCP-FRAP Assay to Guide Membrane Protein Crystallization in Lipid Mesophases. *Crystal growth & design* 11: 1193-201.

Yang, T. T. et al. (1998) Improved fluorescence and dual color detection with enhanced blue and green variants of the green fluorescent protein. *J. Biol. Chem.* 273, 8212-8216.

Yang, H. et al. One-step generation of mice carrying reporter and conditional alleles by CRISPR/Cas-mediated genome engineering. *Cell* 154, 1370-9 (2013).

Yang, F., Moss, L. G. & Phillips Jr, G. N. The molecular structure of green fluorescent protein. *Nat. Biotechnol.* 14, 1246-1251 (1996).

Yanushevich, Y. G. et al. A strategy for the generation of non-aggregating mutants of Anthozoa fluorescent proteins. *FEBS Lett.* 511, 11-4 (2002).

Young C L, Britton Z T, Robinson A S. (2012) Recombinant protein expression and purification: a comprehensive review of affinity tags and microbial applications. *Biotechnology journal* 7: 620-34.

Yin J, Mobarec J C, Kolb P, Rosenbaum D M. (2015) Crystal structure of the human OX2 orexin receptor bound to the insomnia drug suvorexant. *Nature* 519: 247-50.

Zacharias, D. A., Violin, J. D., Newton, A. C. & Tsien, R. Y. Partitioning of lipid-modified monomeric GFPs into membrane microdomains of live cells. *Science* (80-.). 296, 913-6 (2002).

Zhang D, Gao Z G, Zhang K, Kiselev E, Crane S, Wang J, Paoletta S, Yi C, Ma L, Zhang W, Han G W, Liu H, Cherezov V, Katritch V, Jiang H, Stevens R C, Jacobson K A, Zhao Q, Wu B. (2015) Two disparate ligand-binding sites in the human P2Y receptor. *Nature*

Zhong, Y. & Fang, S. Live cell imaging of protein dislocation from the endoplasmic reticulum. *J. Biol. Chem.* 287, 28057-66 (2012).

What is claimed is:

1. A polynucleotide comprising a fusion tag-encoding sequence, the fusion tag-encoding sequence encoding a polypeptide sequence having at least 80% sequence identity to SEQ ID NO: 2, wherein the fusion tag-encoding sequence encodes a residue other than cysteine at a position corresponding to position 49 of SEQ ID NO: 2 and a residue other than cysteine at a position corresponding to position 71 of SEQ ID NO: 2, and wherein the fusion tag-encoding sequence encodes one or more residues selected from the group consisting of a residue other than serine and threonine at a position corresponding to position 66 of SEQ ID NO: 2 and a residue other than tyrosine, tryptophan, histidine, and phenylalanine at a position corresponding to position 67 of SEQ ID NO: 2.

2. The polynucleotide of claim 1, wherein the fusion tag-encoding sequence encodes a residue other than cysteine and methionine at a position corresponding to position 71 of SEQ ID NO: 2.

3. The polynucleotide of claim 1, wherein the fusion tag-encoding sequence encodes a serine at a position corresponding to position 49 of SEQ ID NO: 2 and a serine at a position corresponding to position 71 of SEQ ID NO: 2.

4. The polynucleotide of claim 1, wherein the fusion tag-encoding sequence encodes one or more residues selected from the group consisting of a residue other than serine, threonine, and glycine at a position corresponding to position 66 of SEQ ID NO: 2 and a residue other than tyrosine, tryptophan, histidine, and phenylalanine at a position corresponding to position 67 of SEQ ID NO: 2, wherein the position corresponding to position 66 of SEQ ID NO: 2 is a residue other than glycine when the position corresponding to position 67 of SEQ ID NO: 2 is serine or threonine.

5. The polynucleotide of claim 1, wherein the fusion tag-encoding sequence encodes a threonine at a position corresponding to position 67 of SEQ ID NO: 2.

6. The polynucleotide of claim 5, wherein the fusion tag-encoding sequence encodes a residue other than glycine at a position corresponding to position 66 of SEQ ID NO: 2.

7. The polynucleotide of claim 5, wherein the fusion tag-encoding sequence encodes a threonine at a position corresponding to position 66 of SEQ ID NO: 2.

8. The polynucleotide of claim 1, wherein the fusion tag-encoding sequence encodes at least one, at least two, at least three, at least four, at least five, at least six, at least seven, at least eight, at least nine, at least ten, or all of:
   a residue other than serine at a position corresponding to position 31 of SEQ ID NO: 2;
   a residue other than tyrosine at a position corresponding to position 40 of SEQ ID NO: 2;

a residue other than phenylalanine at a position corresponding to position 65 of SEQ ID NO: 2;
a residue other than serine at a position corresponding to position 66 of SEQ ID NO: 2;
a residue other than phenylalanine at a position corresponding to position 100 of SEQ ID NO: 2;
a residue other than asparagine at a position corresponding to position 106 of SEQ ID NO: 2;
a residue other than tyrosine at a position corresponding to position 146 of SEQ ID NO: 2;
a residue other than methionine at a position corresponding to position 154 of SEQ ID NO: 2;
a residue other than valine at a position corresponding to position 164 of SEQ ID NO: 2;
a residue other than isoleucine at a position corresponding to position 172 of SEQ ID NO: 2; and
a residue other than alanine and valine at a position corresponding to position 207 of SEQ ID NO: 2.

9. The polynucleotide of claim 1, wherein the fusion tag-encoding sequence encodes at least one, at least two, at least three, at least four, or all of:
arginine at a position corresponding to position 31 of SEQ ID NO: 2;
asparagine at a position corresponding to position 40 of SEQ ID NO: 2;
threonine at a position corresponding to position 106 of SEQ ID NO: 2;
valine at a position corresponding to position 172 of SEQ ID NO: 2; and
lysine at a position corresponding to position 207 of SEQ ID NO: 2.

10. The polynucleotide of claim 1, wherein the fusion tag-encoding sequence encodes at least one, at least two, at least three, at least four, at least five, or all of:
leucine at a position corresponding to position 65 of SEQ ID NO: 2;
threonine at a position corresponding to position 66 of SEQ ID NO: 2;
serine at a position corresponding to position 100 of SEQ ID NO: 2;
phenylalanine at a position corresponding to position 146 of SEQ ID NO: 2;
threonine at a position corresponding to position 154 of SEQ ID NO: 2; and
alanine at a position corresponding to position 164 of SEQ ID NO: 2.

11. The polynucleotide of claim 1, further comprising one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence.

12. The polynucleotide of claim 1, further comprising one or more cloning sites upstream, downstream, or both upstream and downstream of the fusion tag-encoding sequence.

13. The polynucleotide of claim 12, further comprising one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence, wherein at least one of the one or more peptide cleavage-encoding sequences is disposed between at least one of the one or more cloning sites and the fusion tag-encoding sequence.

14. The polynucleotide of claim 12, wherein the fusion tag-encoding sequence does not comprise a subsequence identical to at least one of the one or more cloning sites.

15. The polynucleotide of claim 1, further comprising one or more affinity tag-encoding sequences upstream, downstream, or both upstream and downstream of the fusion tag-encoding sequence, each affinity tag-encoding sequence encoding an affinity tag in frame with the fusion tag-encoding sequence.

16. The polynucleotide of claim 15, further comprising one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence, wherein at least one of the one or more peptide cleavage-encoding sequences is disposed upstream or downstream of both the fusion tag-encoding sequence and at least one of the one or more affinity tag-encoding sequences.

17. The polynucleotide of claim 1, further comprising one or more target protein-encoding sequences upstream, downstream, or both upstream and downstream of the fusion tag-encoding sequence, each target protein-encoding sequence encoding a target protein in frame with the fusion tag-encoding sequence.

18. The polynucleotide of claim 17, wherein the one or more target protein-encoding sequences encodes at least one secretory protein.

19. The polynucleotide of claim 17, further comprising one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence, wherein the one or more target protein-encoding sequences is further in frame with at least one of the one or more peptide cleavage-encoding sequences.

20. The polynucleotide of claim 19, wherein the one or more target protein-encoding sequences does not comprise a subsequence identical or substantially identical to at least one of the one or more peptide cleavage-encoding sequences.

21. The polynucleotide of claim 19, wherein at least one of the one or more peptide cleavage-encoding sequences is disposed between at least one of the one or more target protein-encoding sequences and the fusion tag-encoding sequence.

22. The polynucleotide of claim 1, further comprising:
one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence;
one or more cloning sites upstream, downstream, or both upstream and downstream of the fusion tag-encoding sequence, wherein the fusion tag-encoding sequence does not comprise a subsequence identical to at least one of the one or more cloning sites, and wherein at least one of the one or more peptide cleavage-encoding sequences is disposed between the one or more cloning sites and the fusion tag-encoding sequence; and
one or more affinity tag-encoding sequences upstream, downstream, or both upstream and downstream of the fusion tag-encoding sequence, each affinity tag-encoding sequence encoding an affinity tag in frame with the fusion tag-encoding sequence, wherein the at least one of the one or more peptide cleavage-encoding sequences is disposed between the at least one of the one or more cloning sites and at least one of the one or more affinity tag-encoding sequences.

23. The polynucleotide of claim 1, further comprising:
one or more peptide cleavage-encoding sequences upstream, downstream, or both upstream and downstream of the fusion tag-encoding sequence, each peptide cleavage-encoding sequence encoding a peptide cleavage sequence in frame with the fusion tag-encoding sequence;
one or more target protein-encoding sequences upstream, downstream, or both upstream and downstream of the fusion tag-encoding sequence, each target protein-encoding sequence encoding a target protein in frame with the fusion tag-encoding sequence and further in frame with at least one of the one or more peptide cleavage-encoding sequences, wherein the at least one of the one or more peptide cleavage-encoding sequences is disposed between at least one of the one or more target protein-encoding sequences and the fusion tag-encoding sequence, and wherein the at least one or more target protein-encoding sequences does not comprise a subsequence identical with the at least one of the one or more peptide cleavage-encoding sequences; and
one or more affinity tag-encoding sequences upstream, downstream, or both upstream and downstream of the fusion tag-encoding sequence, each affinity tag-encoding sequence encoding an affinity tag in frame with the fusion tag-encoding sequence, wherein the at least one of the one or more peptide cleavage-encoding sequences is disposed between the at least one of the one or more target protein-encoding sequences and at least one of the one or more affinity tag-encoding sequences.

24. A polynucleotide comprising a fusion tag-encoding sequence, the fusion tag-encoding sequence encoding a polypeptide sequence having at least 80% sequence identity to SEQ ID NO: 2, wherein the fusion tag-encoding sequence encodes a residue other than cysteine at a position corresponding to position 49 of SEQ ID NO: 2 and a residue other than cysteine at a position corresponding to position 71 of SEQ ID NO: 2, wherein:
the fusion tag-encoding sequence encodes a serine at a position corresponding to position 49 of SEQ ID NO: 2 and a serine at a position corresponding to position 71 of SEQ ID NO: 2; or
the fusion tag-encoding sequence encodes a serine at a position corresponding to position 49 of SEQ ID NO: 2, a valine at a position corresponding to position 71 of SEQ ID NO:2, and a histidine at a position corresponding to position 67 of SEQ ID NO: 2.

25. The polynucleotide of claim 24, wherein the fusion tag-encoding sequence encodes:
at least three, at least four, or all of:
arginine at a position corresponding to position 31 of SEQ ID NO: 2;
asparagine at a position corresponding to position 40 of SEQ ID NO: 2;
threonine at a position corresponding to position 106 of SEQ ID NO: 2;
valine at a position corresponding to position 172 of SEQ ID NO: 2; and
lysine at a position corresponding to position 207 of SEQ ID NO: 2; and
at least four, at least five, or all of:
leucine at a position corresponding to position 65 of SEQ ID NO: 2;
threonine at a position corresponding to position 66 of SEQ ID NO: 2;
serine at a position corresponding to position 100 of SEQ ID NO: 2;
phenylalanine at a position corresponding to position 146 of SEQ ID NO: 2;
threonine at a position corresponding to position 154 of SEQ ID NO: 2; and
alanine at a position corresponding to position 164 of SEQ ID NO: 2.

26. A polypeptide encoded by a polynucleotide as recited in claim 1.

27. A method of tagging a target protein, comprising generating a polynucleotide as recited in claim 17 and expressing a polypeptide from the polynucleotide.

28. The method of 27, wherein the tagging enhances expression, solubility, or expression and solubility of the target protein.

* * * * *

UNITED STATES PATENT AND TRADEMARK OFFICE
CERTIFICATE OF CORRECTION

PATENT NO. : 9,920,102 B2
APPLICATION NO. : 15/152908
DATED : March 20, 2018
INVENTOR(S) : Erik Lee Snapp et al.

It is certified that error appears in the above-identified patent and that said Letters Patent is hereby corrected as shown below:

In the Specification

Column 1, Line 2 (between "FUSION TAGS FOR PROTEIN EXPRESSION" and "FIELD OF THE INVENTION"), should read --This invention was made with government support under grant numbers DK041296 and GM007491 awarded by the National Institutes of Health. The government has certain rights in the invention.--

Signed and Sealed this
Nineteenth Day of February, 2019

Andrei Iancu
*Director of the United States Patent and Trademark Office*